United States Patent
Ondrus et al.

(10) Patent No.: US 9,840,448 B2
(45) Date of Patent: Dec. 12, 2017

(54) PROCESSES FOR PRODUCING VERY HIGH PURITY 1,1,1,2,3-PENTACHLOROPROPANE

(71) Applicant: SPOLEK PRO CHEMICKOU A HUTNI VYROBU A.S., Usti nad Labem (CZ)

(72) Inventors: Zdenek Ondrus, Vrbice (CZ); Pavel Kubicek, Decin (CZ); Karel Filas, Usti nad Labem (CZ); Petr Sladek, Usti nad Labem-Strekov (CZ)

(73) Assignee: SPOLEK PRO CHEMICKOU A HUTNI VYROBU A.S., Usti nad Labem (CZ)

( * ) Notice: Subject to any disclaimer, the term of this patent is extended or adjusted under 35 U.S.C. 154(b) by 0 days.

(21) Appl. No.: 14/883,648

(22) Filed: Oct. 15, 2015

(65) Prior Publication Data
US 2016/0107956 A1    Apr. 21, 2016

(30) Foreign Application Priority Data

Oct. 16, 2014 (CZ) .................... 2014-705
Oct. 16, 2014 (CZ) .................... 2014-706
Oct. 16, 2014 (CZ) .................... 2014-707

(51) Int. Cl.
*C07C 17/275* (2006.01)
*C07C 17/25* (2006.01)
(Continued)

(52) U.S. Cl.
CPC ............ *C07C 17/087* (2013.01); *C07C 17/04* (2013.01); *C07C 17/25* (2013.01); *C07C 17/266* (2013.01);
(Continued)

(58) Field of Classification Search
CPC ........ C07C 17/25; C07C 17/02; C07C 17/269
See application file for complete search history.

(56) References Cited

U.S. PATENT DOCUMENTS 3,624,169 A    11/1971    Fruhwirth et al.
3,927,131 A    12/1975    Ward
(Continued)

FOREIGN PATENT DOCUMENTS

EP    0094527    11/1983
EP    0131561    1/1985
(Continued)

OTHER PUBLICATIONS

Search Report for Czech Republic App. No. PV 2014-707 dated Aug. 24, 2015.
(Continued)

*Primary Examiner* — Medhanit Bahta
(74) *Attorney, Agent, or Firm* — Pearl Cohen Zedek Latzer Baratz LLP

(57) ABSTRACT

Disclosed is a process for preparing a highly pure 1,1,1,2,3-pentachloropropane product, comprising
1-*a*) providing a reaction mixture comprising ethylene, carbon tetrachloride and a catalyst in a principal alkylation zone to produce 1,1,1,3-tetrachloropropane in the reaction mixture, and
1-*b* treating the reaction mixture obtained in step 1-*a*) to obtain a 1,1,1,3-tetrachloropropane feedstock;
2-*a*) contacting the 1,1,1,3-tetrachloropropane feedstock with a catalyst in a dehydrochlorination zone to produce a reaction mixture comprising 1,1,1,3-tetrachloropropane and 1,1,3-trichloropropene, and
2-*b*) treating the reaction mixture obtained in step 2-*a*) to obtain a 1,1,3-trichloropropene feedstock;
3-*a*) contacting the 1,1,3-trichloropropene feedstock with chlorine in a reaction zone to produce a reaction mixture containing 1,1,1,2,3-pentachloropropane and 1,1,3-trichloropropene, the reaction zone being different from the dehydrochlorination zone, and
(Continued)

3-*b*) treating the reaction mixture obtained in step 3-*a*) to obtain the highly pure 1,1,1,2,3-pentachloropropane product.

30 Claims, 10 Drawing Sheets

(51) Int. Cl.
| | |
|---|---|
| *C07C 17/04* | (2006.01) |
| *C07C 17/38* | (2006.01) |
| *C07C 17/383* | (2006.01) |
| *C07C 17/087* | (2006.01) |
| *C07C 17/266* | (2006.01) |
| *C07C 19/01* | (2006.01) |

(52) U.S. Cl.
CPC ............ *C07C 17/275* (2013.01); *C07C 17/38* (2013.01); *C07C 17/383* (2013.01); *C07C 19/01* (2013.01)

(56) References Cited

U.S. PATENT DOCUMENTS

| | | | | |
|---|---|---|---|---|
| 4,535,194 | A * | 8/1985 | Woodard | ................ C07C 17/04 570/220 |
| 6,187,978 | B1 | 2/2001 | Rygas et al. | |
| 2004/0225166 | A1 | 11/2004 | Wilson et al. | |
| 2005/0049443 | A1 | 3/2005 | Wilson | |
| 2010/0331583 | A1 | 12/2010 | Johnson et al. | |
| 2012/0142980 | A1 | 6/2012 | Nappa et al. | |
| 2012/0157723 | A1 | 6/2012 | Fukuju et al. | |
| 2014/0171698 | A1 | 6/2014 | Elsheikh et al. | |
| 2014/0221705 | A1 | 8/2014 | Wang | |
| 2014/0228601 | A1 * | 8/2014 | Dawkins | ................ C07C 17/38 570/230 |
| 2014/0235903 | A1 | 8/2014 | Wang et al. | |
| 2014/0235906 | A1 | 8/2014 | Yang et al. | |
| 2014/0235907 | A1 | 8/2014 | Yang et al. | |

FOREIGN PATENT DOCUMENTS

| | | | |
|---|---|---|---|
| EP | 0162457 | 11/1985 | |
| EP | 0247215 | 12/1987 | |
| GB | 920855 | 3/1963 | |
| JP | 2010/248104 | 11/2004 | |
| JP | 2012/056920 | 3/2012 | |
| JP | WO 2013015068 A1 * | 1/2013 | .......... C07C 17/206 |
| WO | WO-2008/045910 | 4/2008 | |
| WO | WO-2009/085862 | 7/2009 | |
| WO | WO-2010/131766 | 11/2010 | |
| WO | WO-2012/098420 | 7/2012 | |
| WO | WO-2013/015068 | 1/2013 | |
| WO | WO-2013/074324 | 5/2013 | |
| WO | WO-2013/086262 | 6/2013 | |
| WO | WO-2013/055894 | 8/2013 | |
| WO | WO-2013/119919 | 8/2013 | |
| WO | WO-2014/130445 | 8/2014 | |

OTHER PUBLICATIONS

Search Report for GB App. No. GB1418346.1 dated Dec. 16, 2014.
Search Report for Czech Republic App. No. PV 2014-706 dated Aug. 28, 2015.
Search Report for GB App. No. GB1418345.3 dated Dec. 9, 2014.
Search Report for Czech Republic App. No. PV 2014-705 dated Aug. 28, 2015.
Search Report for GB App. No. GB1418347.9 dated Dec. 3, 2014.
Dil Prvni, Chemie organických sloučenin (1), 1985, Červinka, p. 687.
Dědek, Ferles, Organická chemie, 1991, Červinka p. 282.

* cited by examiner

PROCESSES FOR PRODUCING VERY HIGH PURITY 1,1,1,2,3-PENTACHLOROPROPANE

CROSS-REFERENCE TO RELATED APPLICATIONS

This application claims priority of Czech Patent Applications Nos. PV 2014-705, PV 2014-706, PV 2014-707 all filed Oct. 16, 2014, which are hereby incorporated by reference.

The present invention relates to processes for producing very high purity 1,1,1,2,3-pentachloropropane and also to compositions comprising such compounds.

Haloalkanes find utility in a range of applications. For example, halocarbons are used extensively as refrigerants, blowing agents and foaming agents. Throughout the second half of the twentieth century, the use of chlorofluoroalkanes increased exponentially until the 1980's, when concerns were raised about their environmental impact, specifically regarding depletion of the ozone layer.

Subsequently, fluorinated hydrocarbons such as perfluorocarbons and hydrofluorocarbons have been used in place of chlorofluoroalkanes, although more recently, environmental concerns about the use of that class of compounds have been raised and legislation has been enacted in the EU and elsewhere to reduce their use.

New classes of environmentally friendly halocarbons are emerging and have been investigated, and in some cases, embraced in a number of applications, especially as refrigerants in the automotive and domestic fields. Examples of such compounds include 1,1,1,2-tetrafluoroethane (R-134a), 2-chloro-3,3,3-trifluoropropene (HFO-1233xf), 1,3,3,3-tetrafluoropropene (HFO-1234ze), 3,3,3-trifluoropropene (HFO-1243zf), and 2,3,3,3-tetrafluoropropene (HFO-1234yf), 1,2,3,3,3-pentafluoropropene (HFO-1225ye), 1-chloro-3,3,3-trifluoropropene (HFO-1233zd), 3,3,4,4,4-pentafluorobutene (HFO-1345zf), 1,1,1,4,4,4-hexafluorobutene (HFO-1336mzz), 3,3,4,4,5,5,5-heptafluoropentene (HFO1447fz), 2,4,4,4-tetrafluorobut-1-ene (HFO1354mfy) and 1,1,1,4,4,5,5,5-octafluoropentene (HFO-1438mzz)

While these compounds are, relatively speaking, chemically non-complex, their synthesis on an industrial scale to the required levels of purity is challenging. Many synthetic routes proposed for such compounds increasingly use, as starting materials or intermediates, chlorinated alkanes or alkenes. Examples of such processes are disclosed in WO2012/098420, WO2013/015068 and US2014/171698. The conversion of the chlorinated alkane or alkene starting materials to the fluorinated target compounds is usually achieved using hydrogen fluoride and optionally transition metal catalysts, for example chromium-based catalysts.

An example of an optionally non-catalytic process for preparing fluoroalkenes is disclosed in WO2013/074324.

The issue of the formation of impurities during hydrofluorination reactions is considered in US2010/331583 and WO2013/119919, where thus the need for part fluorinated feedstock purity is described, and also in US2014/235903 regarding reactor impurities.

It has been recognised that when the chlorinated feedstock is obtained from a multi-step process, especially if such steps are linked and run continuously to achieve industrially acceptable product volumes, then the need to prevent cumulative side reactions from generating unacceptable impurities at each process step is very important.

The purity of the chlorinated starting materials will have a substantial effect on the success and viability of the processes (especially continuous processes) for preparing the desirable fluorinated products. The presence of certain impurities will result in side reactions, minimising the yield of the target compound. Removal of these impurities through the use of distillation steps is also challenging. Additionally, the presence of certain impurities will compromise catalyst life, by, for example, acting as catalyst poisons.

Accordingly, there is a need for high purity chlorinated alkanes for use in the synthesis of the fluorinated compounds mentioned above. Several processes for producing purified chlorinated compounds have been proposed in the art.

For example, WO2013/086262 discloses a process for preparing 1,1,2,2,3-pentachloropropane from methylacetylene gas. As can be seen from the examples in that application, the bench scale syntheses disclosed therein resulted in a product having around 98.5% purity, despite being subjected to post-synthetic purification process steps, specifically distillation.

In WO2014/130445, a conventional process is discussed on page 2 of that publication, the first step of which involves the formation of 1,1,1,2,3-pentachloropropane from 1,1,3-trichloropropene. However, the purity profile of that intermediate product is not outlined, nor is any importance attached to the purity profile of that product. In Example 2 of WO2014/130445, a 240db (1,1,1,2,3-pentachloropropane) rich material having a purity level of 96.5 to 98.5% is used.

WO2013/055894 discloses a process for producing tetrachloropropenes, particularly 1,1,2,3-tetrachloropropene and reports that the product obtained from the processes disclosed in that document have advantageously low levels of impurities which can be problematic in downstream processes for producing fluorocarbons. A discussion of the different types of impurities considered to be problematic by the authors of WO2013/055894 is set out in paragraphs [0016] and [0017] of that document US2012/157723 discloses a process in for preparing chlorinated alkanes via a three step process. Seemingly high purity chloroalkanes appear to have been prepared according to the process disclosed in that document. However, the purity data presented in the examples of that application are only given to one decimal place.

From the provision of data presented in this way, it is apparent that the analytical equipment used to measure the impurity profile of the products obtained in the examples of US2012/157723 was insensitive; conventional analytical apparatus enables hydrocarbon levels to 1 ppm (i.e. to four decimal places). Given that one skilled in the art would need to know the impurity profile of chloroalkane feedstocks to be used in industrial scale down to a ppm level, the data presented in US2012/157723 would not be of assistance.

The skilled person would also recognise that the process disclosed in US2012/157723 provides 1,1,1,2,3-pentachloropropane which has relatively low selectivity; as can be seen, from paragraph [0146] of that document, selectivity towards the compound of interest was 95%.

Additional processes in which processes are streamlined by using crude intermediates in downstream stages are disclosed in WO2009/085862.

Despite these advances, problems can still arise through the use of chlorinated compounds obtained from the processes discussed above. Particularly, the presence of impurities especially those which are not easily separable from the compounds of interest (e.g. as a result of similar or higher boiling points) or which reduce the effectiveness or operating life of catalysts used in downstream processes can be problematic.

To minimise such drawbacks, a demand remains for very high purity chlorinated alkane compounds, and also for efficient, selective and reliable processes for preparing such compounds, especially enabling continuous industrial manufacture.

Thus, according to the present invention, there is provided a process for preparing a highly pure 1,1,1,2,3-pentachloropropane product comprising:

1-a) providing a reaction mixture comprising ethylene, carbon tetrachloride and a catalyst in a principal alkylation zone to produce 1,1,1,3-tetrachloropropane in the reaction mixture, and 1-b) treating the reaction mixture obtained in step 1-a) to obtain a 1,1,1,3-tetrachloropropane feedstock;

2-a) contacting the 1,1,1,3-tetrachloropropane feedstock with a catalyst in a dehydrochlorination zone to produce a reaction mixture comprising 1,1,1,3-tetrachloropropane and 1,1,3-trichloropropene, and 2-b) treating the reaction mixture obtained in step 2-a) to obtain a 1,1,3-trichloropropene feedstock;

3-a) contacting the 1,1,3-trichloropropene feedstock with chlorine in a reaction zone to produce a reaction mixture containing 1,1,1,2,3-pentachloropropane and 1,1,3-trichloropropene, the reaction zone being different from the dehydrochlorination zone, and 3-b) treating the reaction mixture obtained in step 3-a) to obtain the highly pure 1,1,1,2,3-pentachloropropane product.

As is apparent, the process of the present invention comprises three main steps, namely step 1), a telomerisation reaction in which carbon tetrachloride is reacted with ethylene to produce 1,1,1,3-tetrachloropropane; step 2), a dehydrochlorination reaction, in which 1,1,1,3-tetrachloropropane is converted to 1,1,3-trichloropropene; and step 3) in which 1,1,3-trichloropropene is chlorinated to yield 1,1,1,2,3-pentachloropropane.

In the process of the present invention, the reaction mixture obtained from each of the three steps outlined above is controlled by degree of conversion and subjected to various treatment steps that will be discussed below in more detail. Global impurity profiles in the intermediates and final product are thus managed to produce high grade product 1,1,1,2,3-pentachloropropane. In embodiments of the invention, treatment steps 1-b), 2-b) and/or 3-b) may comprise one or more distillation steps. Additionally or alternatively, treatment steps 1-b), 2-b) and/or 3-b) may comprise contacting compositions comprising 1,1,1,3-tetrachloropropane (in the case of step 1-b), 1,1,3-trichloropropene (in the case of step 2-b), and/or 1,1,1,2,3-pentachloropropane (in the case of step 3-b) with an aqueous medium.

These and other process steps will now be discussed in more detail in the context of each of steps 1) to 3) specifically:

Step 1—Telomerisation to Produce 1,1,1,3-Tetrachloropropane Feedstock

This step of the invention involves a selective telomerisation reaction which takes place partially or completely in the principal alkylation zone. In that reaction, carbon tetrachloride is reacted with ethylene to produce a 1,1,1,3-tetrachloropropane. While such reactions are known in the art, one issue with such processes is the production of unwanted impurities.

It has been found that by controlling the degree of completion of the reaction, the production of unwanted impurities can be achieved. Thus, in embodiments of the invention, in step 1-a) the concentration of 1,1,1,3-tetrachloropropane in the reaction mixture in the principal alkylation zone is maintained at a level such that the molar ratio of 1,1,1,3-tetrachloropropane:carbon tetrachloride in the reaction mixture extracted from the principal alkylation zone does not exceed 95:5 where the principal alkylation zone is in continuous operation, or 99:1 where the principal alkylation zone is in batchwise operation.

In embodiments of the invention, the molar ratio of 1,1,1,3-tetrachloropropane:carbon tetrachloride in the reaction mixture is controlled in step 1-a) within certain numerically defined limits. As those skilled in the art will appreciate, in such embodiments, while control over the process is characterised herein in terms of the molar ratio between the carbon tetrachloride starting material and 1,1,1,3-tetrachloropropane, it can also considered as control over the conversion of starting material to product—thus a molar ratio of starting material:product of 95:5 equates to a conversion of 5%. The inventors have found that limiting the conversion of the starting material as outlined above minimises the formation of undesirable impurities. Additionally, where reference is made to a molar ratio of the starting material:product being greater than a given value, this means a greater degree of conversion of the starting material to product, i.e. such that the proportion of the product is increased while the proportion of the starting material is decreased.

In step 1-a) of the process of the present invention, the reaction mixture is formed by contacting the alkene and carbon tetrachloride. This may occur in the principal alkylation zone, e.g. by both the alkene and carbon tetrachloride being fed into that zone. Additionally or alternatively, the alkene may be contacted with carbon tetrachloride in a zone upstream of the principal alkylation zone and then fed into the principal alkylation zone.

In embodiments of the invention, in step 1-a), a primary alkylation zone may be employed, upstream of the principal alkylation zone. The reaction mixture may be formed by feeding carbon tetrachloride and ethylene into the primary alkylation zone to form the reaction mixture which is then fed into the principal alkylation zone. In such an embodiment, the partial conversion of carbon tetrachloride to 1,1,1,3-tetrachloropropane may occur in the primary alkylation zone such that that alkane is formed and comprised in the reaction mixture fed into the principal alkylation zone, along with carbon tetrachloride. In additional or alternative embodiments, the amount of ethylene fed into the primary alkylation zone may be limited to retard the conversion of carbon tetrachloride to 1,1,1,3-tetrachloropropane in the primary alkylation zone such that the reaction mixture fed into the principal alkylation zone therefrom comprises carbon tetrachloride and 1,1,1,3-tetrachloropropane, but low levels or substantially no ethylene.

The ethylene and carbon tetrachloride employed in step 1-a) of the present invention may be contacted in a zone (for example, a primary alkylation zone or the principal alkylation zone) by being fed into that zone using any technique or equipment known to those skilled in the art, for example via dispersion devices such as dip tube/s, nozzle/s, ejectors, static mixing devices and/or sparger/s. In such embodiments, the feed of ethylene and/or carbon tetrachloride may be continuous or intermittent. The ethylene supplied as a feed into the zone in which the reaction mixture is formed may be in liquid and/or gaseous form. Likewise, the carbon tetrachloride may be in liquid and/or gaseous form.

In embodiments of the present invention, the reaction mixture (comprising carbon tetrachloride, 1,1,1,3-tetrachloropropane, catalyst and optionally unreacted ethylene) present in the principal alkylation zone (and/or any other alkylation zone that may be employed) may be homogenous, i.e. in a single phase, for example a liquid, or gaseous phase. This can be achieved even where one of the components of the reaction mixture is introduced into the system in a different phase to the other components. For example, in embodiments, gaseous ethylene may be contacted with liquid carbon tetrachloride, causing the ethylene to be dissolved, thus forming a liquid phase homogenous reaction mixture. Alternatively, the reaction mixture may be heterogeneous.

The carbon tetrachloride and ethylene starting materials employed in step 1-a) of the present invention may have a high degree of purity, for example, either or both of those materials may be at least about 95% pure, at least about 97% pure, at least about 99% pure, at least about 99.5% pure, at least about 99.7% pure, or at least about 99.9% pure.

In embodiments of the present invention, the carbon tetrachloride starting material comprises less than less than about 2000 ppm, less than about 1000 ppm, less than about 500 ppm, less than about 200 ppm, less than about 100 ppm, less than about 50 ppm or less than about 20 ppm bromides or brominated organic compounds.

Additionally or alternatively, the carbon tetrachloride starting material may have a moisture content of about 200 ppm or less, about 100 ppm or less, about 50 ppm or less or about 35 ppm or less.

The source of carbon tetrachloride may be located on the same site as the apparatus for operating the processes of the present invention. In embodiments, the source of the carbon tetrachloride may be adjacent to a chlor alkali facility with, for example, a membrane electrolysis plant, from which high purity chlorine will be available to use in the production of the carbon tetrachloride. The site may also comprise plants for producing epichlorohydrin (for example from glycerol feedstock), glycidol, and/or epoxy resin, or oxychlorination plant (e.g. vinyl chloride monomer VCM plant, Perchloroethylene plant etc) or a site with HCl electrolysis plant, such that the hydrogen chloride gas, produced as a byproduct in any associated steps or processes, is effectively also utilised. Thus for best economic use of a chlor alkali facility, an integrated facility with plants for chlorine reactions and capture/re-use of hydrogen chloride is envisioned.

The reaction mixture formed in step 1-a) of the invention may be extracted from the principal alkylation zone (and/or, if employed, the primary alkylation zone). This may be conducted on a continuous or intermittent basis. For the avoidance of doubt, where reference is made in the context of step 1-a) of the process of the present invention to the continuous extraction of material from the zones employed in the process of the present invention, this should not be assigned a purely literal meaning. One skilled in the art would recognise that, in such embodiments, material may be removed on a substantially continuous basis while the zone in question is at operating conditions and, if its purpose is to set up a steady state reaction (e.g. an alkylation), once the reaction mixture therein has attained the required steady state.

One of the advantages of the present invention is that the presence of certain impurities typically observed in commercially supplied ethylene (such as certain organic impurities, e.g. as alcohols, ethers, esters, and aldehydes) can be tolerated and/or removed using process steps outlined herein. The ethylene starting material may be derived from bioethanol, from ethanol or from crude oil.

An additional advantage of the processes of the present invention is that i) the continuous production of chlorinated alkane and ii) substantially full utilisation of the ethylene starting material can be achieved with no escape of the ethylene into the off-gas system.

The amount of unreacted ethylene in the reaction mixture leaving the principal alkylation zone is less than 0.6%, less than 0.3%, less than 0.2%, or less than 0.1%. Any unreacted gaseous ethylene is directly recycled back to the reaction zone/s operating at elevated pressure. Alternatively, the unreacted gaseous ethylene is recycled back to the reaction zone/s operating at elevated pressure by absorbing ethylene into the cold liquid carbon tetrachloride feedstock. Advantageously, the gaseous reagent/s, if needed to be recycled, may be handled without using expensive compressor systems.

One of the advantages of the process of step 1-a) of the present invention is that it permits the production of 1,1,1,3-tetrachloropropane with high isomeric selectivity. Thus, in embodiments of the invention, 1,1,1,3-tetrachloropropane is produced in step 1-a) with isomeric selectivity of at least about 95%, at least about 97%, at least about 98%, at least about 99%, at least about 99.5%, at least about 99.7%, at least about 99.8% or at least about 99.9%

The alkylation reaction conducted in step 1-a) of the process of the present invention, to produce 1,1,1,3-tetrachloropropane is accelerated through the use of a catalyst. As used herein, the term catalyst is used to encompass not only the use of a single compound or material having catalytic effect, e.g. a solid metal or a metal salt, but a catalyst system which may additionally comprise a catalytic material and a co-catalyst or promoter such as a ligand.

Any catalyst known by those skilled in the art to find utility in the formation of 1,1,1,3-tetrachloropropane from carbon tetrachloride and ethylene may be employed.

In embodiments of the invention, the catalyst is metallic. Any metal which can function as a catalyst in the alkylation reaction of the present invention may be employed, including, but not limited to copper and/or iron. The metallic catalyst may be present in its solid form (e.g., in the case of copper or iron, in particulate form (e.g. powder or filings), wire and/or mesh or the like) and/or as a salt in which the metal may be in any oxidation state (e.g. cuprous salts such as cuprous chloride, cuprous bromide, cuprous cyanide, cuprous sulphate, cuprous phenyl and/or ferrous and/or ferric salts such as ferrous chloride and ferric chloride).

Where metallic salts are employed as catalysts in the processes of the present invention, these may be added to the alkylation zone/s and/or form in situ therein. In the latter case, solid metal may be added into the alkylation zone/s and, owing to the conditions therein, the salt may be formed. For example, if solid iron is added into a chlorination reaction mixture, the chlorine present may combine with the elemental iron to form ferric or ferrous chloride in situ. Where metallic salts are formed in situ, it may nevertheless be desirable to maintain a predetermined level of elemental metal catalyst in the reaction mixture (for example, an excess of elemental metal as compared to the level of metallic salt/s and/or ligand) and thus, additional elemental metal catalyst may be added as the reaction proceeds, either continuously or intermittently.

As mentioned above, in embodiments of the present invention, the catalyst may also comprise a ligand, preferably an organic ligand, which may form a complex with the metallic catalyst. Suitable ligands include amines, nitrites, amides, phosphates and phosphites. In embodiments of the invention, the ligand employed is an alkylphosphate, such as trimethylphosphate, triethylphosphate, tributylphosphate, and triphenylphosphate.

Additional metallic catalysts and ligands are known to those skilled in the art and are disclosed in the prior art, for example, U.S. Pat. No. 6,187,978, the contents of which are incorporated by reference. Such catalysts may be employed in step 1-a) of the present invention.

The components of the catalyst system, where used, may be fed into the alkylation zone/s (e.g. the principal alkylation zone, and/or, if used, the primary alkylation zone) continuously or intermittently. Additionally or alternatively, they may be introduced into the alkylation zone/s (e.g. the principal alkylation zone, and/or, if used, the primary alkylation zone) prior to and/or during commencement of the alkylation reaction of step 1-a).

Additionally or alternatively, the catalyst (or components of the catalyst, for example the ligand) may be fed into the alkylation zone/s (e.g. the principal alkylation zone, or, if used, the primary alkylation zone) together with other components of the reaction mixture, for example in a feed of carbon tetrachloride and/or ethylene.

In embodiments of the invention in which the catalyst comprises a metallic catalyst and a promoter such as a ligand, the molar ratio of the promoter:metallic catalyst in the reaction mixture present in the principal alkylation zone, and/or, if used, the primary alkylation zone is maintained at a ratio of greater than 1:1, more preferably at a ratio of greater than 2:1, 5:1 or 10:1.

Where solid metal catalyst is added to the reaction mixture, this may be added into the primary alkylation zone, if used, and/or into the principal alkylation zone. In embodiments of the invention, solid metal catalyst is added into the primary alkylation zone, if used, and/or into the principal alkylation zone in amounts to maintain a level of about 0.1 to 4%, about 0.5 to 3% or about 1 to 2% by weight of the reaction mixture.

Additionally or alternatively, where metallic catalysts are employed, these are added to establish a dissolved metal content of about 0.1%, about 0.15% or about 0.2% to about 1.0, about 0.5 or about 0.3% by weight of the reaction mixture.

In embodiments of the invention in which the catalyst system employed comprises a metallic catalyst and promoter, the metallic catalyst and promoter can be added to the reaction mixture simultaneously and/or in the same part of the apparatus, for example in the primary alkylation zone (if used) and or the principal alkylation zone.

Alternatively, the metallic catalyst and promoter can be added at different locations in the apparatus, or sequentially or separately. For example, solid metal catalyst can be added to the primary alkylation zone with promoter being fed into that zone from a recycle loop to which additional, fresh promoter may also be added.

In embodiments of the invention, the primary and/or principal alkylation zones employed in step 1-a) are operated under atmospheric or superatmospheric pressure, i.e. at a pressure greater than about 100 kPa, greater than about 200 kPa, greater than about 300 kPa, greater than about 400 kPa, greater than about 500 kPa, greater than about 600 kPa, greater than about 700 kPa, or greater than about 800 kPa. Typically, the pressure in the primary and/or principal alkylation zones will be equal to or lower than about 2000 kPa, about 1700 kPa, about 1500 kPa, about 1300 kPa, about 1200 kPa or about 1000 kPa.

Additionally or alternatively, in embodiments of the invention, the primary and/or principal alkylation zones employed in step 1-a) are operated at elevated temperatures, i.e. temperatures equal to or greater than about 30° C., about 40° C., about 50° C., about 60° C., about 70° C., about 80° C., about 90° C. or about 100° C. Typically, the primary and/or principal alkylation zones will be operated at temperatures equal to or lower than about 200° C., about 180° C., about 160° C., about 140° C., about 130° C., about 120° C., or about 115° C.

The use of temperatures and pressures within these ranges combined with the other features of step 1-a) of the present invention have been advantageously found to maximise yields and/or selectivity of 1,1,1,3-tetrachloropropane, while minimising the formation of problematic byproducts.

In processes of the invention, a plurality of alkylation zones may be employed in step 1-a). Any number of alkylation zones may be employed, for example 1, 2, 3, 4, 5, 6, 7, 8, 9 or 10 or more. In embodiments in which a plurality of primary and/or principal alkylation zones are employed, there may be any number (for example 1, 2, 3, 4, 5, 6, 7, 8, 9, or 10 or more) primary and/or principal alkylation zones present.

For the avoidance of doubt, where reference is made to the properties of an alkylation zone (primary and/or principal), e.g. its operating conditions, its method of operation, its properties, etc., insofar as embodiments of the present invention are concerned which comprise a plurality of primary and/or principal alkylation zones, one, some or all of those zones may exhibit the property/ies in question. For example, if, for brevity, reference is made to a principal alkylation zone having a specified operating temperature, then, insofar as embodiments including a plurality of principal alkylation zones are concerned, this should be taken as a reference that one, some or all of those principal alkylation zones are operated at the specified temperature.

In arrangements where a plurality of primary and/or principal alkylation zones are employed, those alkylation zones may be operated in parallel and/or in series.

In arrangements in which primary and principal alkylation zones are employed in step 1-a) of the present invention, the reaction between ethylene and carbon tetrachloride may be controlled to prevent it proceeding beyond a certain degree of completion in the primary alkylation zone, for example such that the molar ratio of 1,1,1,3-tetrachloropropane:carbon tetrachloride in the reaction mixture extracted from the primary alkylation zone and/or fed into the principal alkylation zone does not exceed 85:15, 90:10, 93:7 or 95:5 although this is not essential. Additionally or alternatively, the reaction may be permitted to run to a relatively advanced stage of completion, such that the molar ratio of 1,1,1,3-tetrachloropropane:carbon tetrachloride in the reaction mixture extracted from the primary alkylation zone and/or fed into the principal alkylation zone is greater than 50:50, 60:40, 70:30, 75:25 or 80:20.

Control of the progress of the step 1-a) reaction in the primary alkylation zone may be achieved through the use of reaction conditions which do not favour the total conversion of carbon tetrachloride to 1,1,1,3-Tetrachloropropane. Additionally, or alternatively, control of the progress of the alkylation reaction in the primary alkylation zones may be achieved through careful selection of the residence time of the reaction mixture in the primary alkylation zones, for example about 20 to 300 minutes, about 40 to 250 minutes, about 60 to about 200 minutes or about 90 to about 180 minutes. In embodiments of the invention, the molar ratio may be controlled by limiting the amount of ethylene fed into the primary and/or principal alkylation zones employed in step 1-a) of the invention. For example, the molar ratio of carbon tetrachloride:ethylene fed into the primary and/or principal alkylation zones may range from about 50:50 to about 55:45, about 60:40, about 65:35, about 70:30, about 75:25, about 80:20 about 85:15 or about 90:10.

In embodiments where primary and principal alkylation zones are employed in step 1-a), the bulk of 1,1,1,3-tetrachloropropane may be produced in the primary alkylation zone. In such embodiments, the proportion of 1,1,1,3-tetrachloropropane produced in the principal reaction zone may be significantly lower e.g. such that the molar ratio of 1,1,1,3-tetrachloropropane:carbon tetrachloride in the reaction mixture is increased by 1 to 10, 2 to 8 or 3 to 5.

For example, if the molar ratio of 1,1,1,3-tetrachloropropane:carbon tetrachloride in the reaction mixture extracted from the primary alkylation zone and fed into the principal alkylation zone is 90:10, that molar ratio may be increased by 2, 3 or 5 in the principal alkylation zone so that the molar ratio of 1,1,1,3-tetrachloropropane:carbon tetrachloride present in the mixture extracted from the principal alkylation zone may be 92:8, 93:7 or 95:5.

However, the viability of the processes of step 1-a) of the present invention is not dependent on the major part of the conversion of carbon tetrachloride to 1,1,1,3-tetrachloropropane occurring in the primary reaction zone. Thus, in alternative embodiments, the degree of conversion of carbon tetrachloride to 1,1,1,3-tetrachloropropane may be balanced between the primary and principal alkylation zones, or may be greater in the principal alkylation zone than in the primary alkylation zone.

The reaction mixture may then be taken from the primary alkylation zone (continuously or intermittently) and fed into the principal alkylation zone in which a proportion of the remaining carbon tetrachloride present in the reaction mixture is converted to 1,1,1,3-tetrachloropropane. In such embodiments, any unreacted ethylene starting material present in the reaction mixture may advantageously be fully (or at least nearly fully) utilised.

In process step 1-a) of the process of the present invention, where employed, the primary and principal alkylation zones may be operated under different conditions. The principal alkylation zone may be operated under a greater pressure than the primary alkylation zone/s, for example at a pressure which is at least about 10 kPa higher, about 20 kPa higher, about 50 kPa higher, about 100 kPa higher, about 150 kPa higher, about 200 kPa higher about 300 kPa or about 500 kPa higher.

In embodiments of the invention, ethylene may not be fed into the principal alkylation zone; the only source of ethylene to those zone/s may be in the reaction mixture fed into the principal alkylation zone.

Additionally, in embodiments in which the alkylation reaction between carbon tetrachloride and ethylene is catalysed by a metallic catalyst (optionally including a ligand), metallic catalyst and/or ligand may not be fed in to the principal alkylation zone. In such embodiments, the sole source of catalyst may be the reaction mixture fed into the principal alkylation zone. Additionally or alternatively, the principal alkylation zone may be provided with a catalyst bed.

In step 1-a) of the process of the present invention, where primary and principal alkylation zones are employed and solid metal catalyst is present in the reaction mixture in the primary alkylation zone (e.g. by being added directly thereto), when the reaction mixture is extracted from the primary alkylation zone in order to be fed into the principal alkylation zone, the extraction of the reaction mixture from the primary alkylation zone may be carried out such that very little, if any, solid metal catalyst is present in the reaction mixture, for example less than about 5 mg, about 2 mg, about 1 mg, about 0.5 mg, about 0.2 mg, about 0.1 mg of solid metal catalyst per litre of reaction mixture.

This may be achieved through the use of any technique and/or equipment known to those skilled in the art, for example a tube extending into the primary alkylation zone/s at an appropriate location, being provided with a filtering mesh and/or having an appropriate diameter.

Where employed, the primary and principal alkylation zones may be in the same or different reactors, which may be the same or different types of reactors. Further, in embodiments where a plurality of primary alkylation zones are employed, these may be in the same or different reactors. Likewise, in embodiments where a plurality of principal alkylation zones are employed, these may be in the same or different reactors.

Any type of reactor or reactors known to those skilled in the art may be employed in step 1-a of the process of the present invention. Specific examples of reactors that may be used to provide alkylation zones are column reactors (e.g. column gas-liquid reactors), tubular reactors, bubble column reactions, plug/flow reactors (e.g. tubular plug/flow reactors) and stirred tank reactors (e.g. continuously stirred tank reactors).

Arrangements in which the primary alkylation zone is present in a continuously stirred tank reactor (CSTR) and the principal alkylation zone is present in a plug/flow reactor have provided advantageous results.

One advantage of step 1-a) of the process of the present invention is that desirous results are obtained whether the alkylation zones (e.g. the primary alkylation zone and/or the principal alkylation zone) are operated in a continuous (steady state) or batchwise process. The terms 'continuous process' and 'batchwise process' will be understood by those skilled in the art.

In embodiments, the primary alkylation zone, where employed, is operated in a continuous or batchwise process. Additionally or alternatively, the second alkylation zone/s, where employed, are operated in a continuous or batchwise process.

In embodiments of step 1-a) of the invention, where the principal alkylation zone is in continuous operation, the content of 1,1,1,3-tetrachloropropane may be controlled such that the ratio of that compound:carbon tetrachloride in the reaction mixture extracted from the principal alkylation zone does not exceed about 94:6, about 92:8, or about 90:10.

In alternative embodiments of step 1-a) of the process of the present invention where the principal alkylation zone is in batchwise operation, the content of 1,1,1,3-tetrachloropropane may be controlled such that the ratio of that compound:carbon tetrachloride in the reaction mixture extracted from the principal alkylation zone does not exceed about 97:3, about 95:5, or about 90:10.

Regardless of whether the principal alkylation zone is in continuous or batchwise process, the content of 1,1,1,3-tetrachloropropane may be controlled such that the ratio of that compound:carbon tetrachloride in the reaction mixture extracted from the principal alkylation zone is equal to or greater than about 70:30, about 80:20, about 85:15, or about 90:10.

It has surprisingly been found that by controlling the degree of conversion of carbon tetrachloride to 1,1,1,3-tetrachloropropane, and preventing the reaction from proceeding to completion, the formation of impurities is advantageously reduced. For example, in embodiments in which the ethylene feedstock employed in the processes of the present invention is ethylene, the production of undesired byproducts such as pentanes (which would otherwise be formed) is minimized.

Thus, in embodiments of the invention, reaction mixture formed in step 1-a) and extracted from the principal reaction zone comprises serial reaction products, i.e. compounds comprising a greater number of carbon atoms than 1,1,1,3-tetrachloropropane, of less than about 5%, less than about 2%, less than about 1%, less than about 0.5%, less than about 0.2%, less than about 0.1%, less than about 0.05% or less than about 0.02%.

Control of the content of 1,1,1,3-tetrachloropropane may be achieved by retarding the progress of the alkylation process and/or by introducing additional carbon tetrachloride into the principal alkylation zone.

In embodiments of step 1-a) in which the content of 1,1,1,3-tetrachloropropane is controlled by retarding the alkylation process, this can be achieved through the use of reaction conditions which do not favour the total conversion of carbon tetrachloride to 1,1,1,3-Tetrachloropropane. For example, this can be achieved through exposing the reaction mixture, or at least a portion thereof, to conditions which decelerate or halt the progress of the alkylation reaction. In such embodiments, the pressure that the reaction mixture is exposed to in the alkylation zone/s (for example, the principal alkylation zone/s, where employed) could be reduced significantly, e.g. by at least about 500 kPA, by at least about 700 kPa, by at least about 1000 kPa.

Additionally or alternatively, the pressure to which the reaction mixture is exposed can be reduced to atmospheric or subatmospheric pressure. The reduction in pressure can occur in one or more alkylation zone (for example, one, some or all of the principal alkylation zones, if used). Additionally or alternatively, the reduction in pressure can occur following extraction of the reaction mixture from the alkylation zone/s.

Additionally or alternatively, in embodiments in which the content of 1,1,1,3-tetrachloropropane is controlled by retarding the alkylation process, this can be achieved through limiting the ethylene level present in the reaction mixture formed in step 1-a of the process of the present invention.

In embodiments of the invention, control of the progress of the alkylation reaction in the alkylation zone/s may be achieved through careful selection of the residence time of the reaction mixture in the alkylation zone/s. For example, in embodiments in which one or more principal alkylation zones are employed, the residence time of the reaction mixture in those zone/s may be, for example about 1 to 120 minutes, about 5 to 100 minutes, about 15 to about 60 minutes or about 20 to about 40 minutes.

In embodiments in which the content of 1,1,1,3-tetrachloropropane is controlled by retarding the alkylation process, this can additionally or alternatively be achieved by reducing the operating temperature of the principal alkylation zone, for example by about 5° C. or more, about 10° C. or more, about 20° C. or more, about 50° C. or more or by about 100° C. or more. Additionally or alternatively, the operating temperature of the principal conversion zone can be reduced to about 20° C., about 10° C. or about 0° C.

Additionally or alternatively, the alkylation process can be retarded by limiting the amount of catalyst present in the reaction mixture, or removing the catalyst bed (if present) from the principal alkylation zone.

The rate of agitation or stirring of the principal alkylation zone can also be reduced to retard the alkylation process.

As mentioned above, the reaction mixture extracted from the principal alkylation zone comprises carbon tetrachloride, catalyst and 1,1,1,3-tetrachloropropane. However, in embodiments of the invention, depending on the conditions and equipment employed, the reaction mixture extracted from the principal alkylation zone may additionally comprise unreacted ethylene starting material and/or impurities (e.g. chlorinated alkane impurities, chlorinated alkene impurities and/or oxygenated organic compounds).

Given that the presence of unreacted ethylene alongside 1,1,1,3-tetrachloropropane can be problematic in step 2) of the present invention, in embodiments, the reaction mixture extracted from the principal alkylation zone may be subjected to a dealkenation step (as part of step 1-b)) in which at least about 50% or more by weight of the ethylene present in the reaction mixture is extracted therefrom and at least about 50% of the extracted ethylene is fed back into the reaction mixture provided in the principal alkylation zone.

Such embodiments are particularly advantageous as they enable substantial if not total utilisation of the ethylene feed employed in the processes of the present invention.

In embodiments of the invention, at least about 60%, at least about 70%, at least about 80%, at least about 90%, at least about 95%, at least about 97% or at least about 99% of the ethylene present in the reaction mixture extracted from the principal alkylation zone is removed during the dealkenation step.

The removal of unreacted ethylene from the reaction mixture can be achieved using any technique known to those skilled in the art. In embodiments of the invention, extraction of the ethylene from the reaction mixture can be achieved using distillation techniques which result in a stream rich in ethylene being obtained, for example flash evaporation, which may conveniently be deployed in embodiments where the boiling point of the ethylene is substantially lower than the boiling point of the other compounds present in the reaction mixture, as is the case with ethylene (−103.7° C.) vs carbon tetrachloride (76.6° C.) and 1,1,1,3-Tetrachloropropane (159° C.).

Dealkenation of the reaction mixture in step 1-b) of the process of the present invention may be selective. In other words, the ethylene is selectively extracted, without the substantial removal of other compounds from the reaction mixture. In such embodiments, the ethylene extracted from the reaction mixture may comprise less than about 10%, less than about 5%, less than about 2% or less than about 1% of compounds other than the ethylene starting material.

In step 1-b) of the process of the present invention, distillation of the reaction mixture can be achieved, using any techniques or equipment known to those skilled in the art. For example, conventional distillation apparatus (e.g. a distillation column) may be employed. Additionally or alternatively, in embodiments of the invention, where pressure in the principal alkylation zone from which the reaction mixture is extracted is superatmospheric, evaporation of ethylene from the reaction mixture may be achieved by maintaining the reaction mixture at a superatmospheric pressure following extraction from the principal alkylation zone and feeding it into an evaporation zone in which evaporation of the ethylene from the reaction mixture occurs.

In embodiments of the invention, evaporation of ethylene from the reaction mixture in the evaporation zone in step 1-b) can be achieved by depressurisation, for example, by significantly reducing the pressure that the reaction mixture is under, e.g. by at least about 500 kPA, by at least about 700 kPa, by at least about 1000 kPa, and/or to atmospheric or subatmospheric pressure. Conveniently, in embodiments in which depressurisation is used either partly or totally to decelerate or halt the conversion of carbon tetrachloride to 1,1,1,3-tetrachloropropane, and also to separate ethylene from the reaction mixture, these aims can be simultaneously achieved in a single depressurisation step.

The evaporation zone may be in any apparatus in which evaporation of the ethylene present in the reaction mixture can be achieved, for example, flash evaporation apparatus such as a flash drum.

The ethylene distilled off from the reaction mixture in step 1-b), for example by flash evaporation, is preferably extracted from the distillation apparatus in liquid or gaseous form.

In processes of the present invention, at least about 50%, at least about 70%, at least about 80%, at least about 90%, at least about 95%, at least about 97% or at least about 99% by weight of the of the ethylene extracted from the evaporation zone is fed back (i.e. recycled) to the primary and/or principal alkylation zone.

For the avoidance of doubt, in embodiments of the invention, the distilled ethylene obtained in step 1-b) of the process, if in gaseous form, may or may not be converted back to a liquid, prior to being fed in to the reaction mixture provided in the principal alkylation zone. For example, conversion of the gaseous ethylene to liquid ethylene may be achieved by being passed through a condenser and/or being trapped in a stream of liquid (preferably cooled) carbon tetrachloride, which can then be fed into the alkylation zone/s. Gaseous ethylene may be trapped in a liquid stream of carbon tetrachloride using any techniques or equipment known to those skilled in the art, for example an absorption column. This arrangement is advantageous as it aids the full industrial utilisation of the compounds employed in the alkylation process.

As mentioned above, reaction mixture formed in step 1-a) of the process of the present invention, and extracted from the alkylation zone/s comprises catalyst. Given that the presence of catalyst may be problematic in step 2), it may be preferable to remove the catalyst from the reaction mixture. Step 1-b) may comprise such a removal step.

Additionally, for catalyst systems in which costly catalysts and/or promoters such as the alkylphosphate and alkylphosphite ligands mentioned above are employed, the recovery of reusable catalyst systems and/or components thereof is also preferable to minimise the quantities of fresh catalyst that must be used, thus reducing operational cost.

While the challenge of removing catalysts of the type employed in the processes of the present invention from reaction mixtures has been addressed in the past, the techniques and conditions employed to do so (typically involving distillation using aggressive conditions) can be damaging to the catalyst systems and can reduce their catalytic ability. This is especially the case where the catalyst system is temperature sensitive as is the case for systems including certain organic ligands as promoters, such as alkylphosphates and alkylphosphites.

Thus, in embodiments of the present invention, step 1-b) may comprise the step of subjecting reaction mixture extracted from the alkylation zone/s to an aqueous treatment step in which the reaction mixture is contacted with an aqueous medium in an aqueous treatment zone, a biphasic mixture is formed and an organic phase comprising catalyst is extracted from the biphasic mixture.

In embodiments of the invention in which reaction mixture formed in step 1-a) is subjected to an aqueous treatment step in step 1-b), the reaction mixture may comprise unreacted carbon tetrachloride and 1,1,1,3-tetrachloropropane. Additionally, the reaction mixture comprises catalyst (for example a complex of the metallic catalyst and catalyst ligand, or the free catalyst ligand) and/or unreacted ethylene starting material.

Through the use of the aqueous treatment step in step 1-b of the process of the present invention, the damaging conditions described in the prior art (for example, high temperature, high catalyst concentration and/or the presence of iron compounds in anhydrous form) can be avoided, meaning that the recovered catalyst and/or components thereof (e.g. the ligand or promoter) can be re-used (for example, it can be recycled back to the reaction mixture provided in the alkylation zone/s) without any substantial loss in catalytic ability. In embodiments of the invention, the steam stripping of the biphasic aqueous treated mixture is preferred as the boiler temperatures in excess of 100° C. can be avoided and atmospheric pressure can be employed.

A further advantage of the aqueous treatment step in step 1-b) of the process of the present invention is that it results in the removal of impurities from the reaction mixture, for example, oxygenated organic products, if present. Advantageously, the levels of such materials in the reaction mixture are significantly reduced to acceptable levels, if not eliminated, by the aqueous treatment step.

In embodiments of the invention in a which an aqueous treatment step is performed in step 1-b), the reaction mixture provided in the aqueous treatment zone may comprise 1,1,1,3-tetrachloropropane (for example in amounts of about 50% or greater), catalyst, and optionally carbon tetrachloride and/or impurities, for example organic oxygenated compounds, chlorinated alkane compounds (other than 1,1,1,3-tetrachloropropane) and or chlorinated alkene compounds.

This catalytic recovery process in step 1-b) involves the reaction mixture being subjected to an aqueous treatment step in which the reaction mixture is contacted with an aqueous medium in an aqueous treatment zone. In embodiments, the aqueous medium is water (as a liquid and/or vapour). Additionally, the aqueous medium may additionally comprise other compounds, such as acids. Inorganic acids, such as hydrochloric acid, sulfuric acid and/or phosphoric acid may be employed.

Where the aqueous medium fed into the aqueous treatment zone is partially or totally in liquid form, a biphasic mixture will be formed upon the liquid aqueous medium contacting the reaction mixture.

Alternatively, where the aqueous medium is in gaseous form, e.g. steam, a biphasic mixture may not be formed immediately, but only once the gaseous aqueous medium condenses. The apparatus employed in aqueous treatment step may be configured such that condensation of the aqueous medium to form the biphasic mixture occurs within and/or remote from the aqueous treatment zone.

In embodiments of the invention, 1,1,1,3-tetrachloropropane may be extracted from the mixture formed in the aqueous treatment zone. The majority (e.g. at least about 50%, at least about 60%, at least about 70%, at least about 80% or at least about 90%) of 1,1,1,3-tetrachloropropane present in the reaction mixture fed into the aqueous treatment zone may be extracted from the mixture formed in the aqueous treatment zone using any techniques or equipment known to those skilled in the art.

In embodiments of the invention, distillation is used to extract 1,1,1,3-tetrachloropropane from the mixture formed in the aqueous treatment zone. The distillation may result in a stream rich in 1,1,1,3-tetrachloropropane being obtained.

As used throughout this specification, the term 'a stream rich in' a specific compound (or corresponding language) is used to mean that the stream comprises at least about 90%, about 95%, about 97%, about 98% or about 99% of the specific compound. Further, the term 'stream' should not be interpreted narrowly, but encompasses compositions (including fractions) extracted from a mixture via any means.

For example, 1,1,1,3-tetrachloropropane may be distilled off, for example, from a gaseous mixture comprising that alkane and water vapour. 1,1,1,3-tetrachloropropane may be distilled off in a stream rich in 1,1,1,3-tetrachloropropane. This may be used as the feedstock for step 2-a). In embodiments of the invention in which the aqueous medium is partly or totally in liquid form, distillation of 1,1,1,3-tetrachloropropane may be achieved by boiling the mixture present to evaporate the 1,1,1,3-tetrachloropropane and produce the gaseous 1,1,1,3-tetrachloropropane/water vapour mixture from which 1,1,1,3-tetrachloropropane can be distilled, for example using steam distillation techniques.

Additionally or alternatively, where the aqueous medium is provided partly or totally in gaseous form, this evaporates 1,1,1,3-tetrachloropropane to form the gaseous mixture comprising that alkane and water vapour which can then optionally be subjected to distillation to remove 1,1,1,3-tetrachloropropane, for example steam distillation. 1,1,1,3-Tetrachloropropane may be obtained in a stream rich in that compound.

In embodiments in which 1,1,1,3-tetrachloropropane is distilled from a gaseous mixture of 1,1,1,3-tetrachloropropane and water vapour, the distillation apparatus may be coupled to the aqueous treatment zone so that the gaseous chlorinated alkane/water vapour mixture can pass directly from the aqueous treatment zone to that apparatus. Alternatively, the distillation apparatus may be located remotely from the aqueous treatment zone such that the gaseous mixture is firstly extracted from the aqueous treatment zone and then conveyed to the distillation apparatus. In either arrangement, 1,1,1,3-tetrachloropropane may be obtained in a stream rich in that compound.

In alternative embodiments, where the aqueous medium and reaction mixture are in liquid form, 1,1,1,3-tetrachloropropane may be extracted from that liquid mixture using conventional distillation techniques known to those skilled in the art. 1,1,1,3-Tetrachloropropane may be obtained in a stream rich in that compound. This stream may be used as the feedstock in step 2-a) of the process of the present invention.

The biphasic mixture may be formed in step 1-b) within the aqueous treatment zone or remotely therefrom. The biphasic mixture comprises an aqueous phase (as a result of the aqueous medium added to the aqueous treatment zone) and an organic phase (comprising 1,1,1,3-tetrachloropropane, optionally unreacted carbon tetrachloride, and importantly catalyst).

To maximise the volume of the organic phase and thus facilitate extraction of that phase from the biphasic mixture, a haloalkane extraction agent (e.g. carbon tetrachloride and/or 1,1,1,3-tetrachloropropane) may be added to the biphasic mixture (e.g. by being continuously or intermittently fed into the aqueous treatment zone) using techniques and equipment known to those skilled in the art.

The organic phase can be extracted from the biphasic residue using any technique known to those skilled in the art, e.g. decantation. For example, extraction of the organic phase can be performed by the sequential phase extraction from the aqueous treatment zone or the vessel in which it is contained. Alternatively, the biphasic mixture can be extracted from the aqueous treatment zone and subjected to a phase separation step remote from the aqueous treatment zone.

In embodiments of the invention, the biphasic mixture and/or the extracted organic phase can be filtered. In embodiments, this will result in a filter cake being obtained which can optionally be totally or partially employed as a source of iron.

Extraction of 1,1,1,3-tetrachloropropane from the mixture formed during the aqueous treatment step may be performed prior to extraction of the organic phase therefrom, and/or after the organic phase is extracted from that mixture. Some exemplary embodiments in which 1,1,1,3-tetrachloropropane is extracted from the mixture formed during the aqueous treatment step are outlined above.

As a further example, the biphasic mixture may be heated to form a gaseous mixture from which 1,1,1,3-tetrachloropropane can be extracted (optionally as a stream rich in 1,1,1,3-tetrachloropropane—which may be used as the feedstock in step 2-a)), e.g. via distillation. The organic phase, having a reduced proportion of 1,1,1,3-tetrachloropropane, may then be extracted from the biphasic mixture.

Additionally or alternatively, the organic phase may be extracted from the biphasic mixture as discussed above. 1,1,1,3-tetrachloropropane may then be extracted (optionally as a stream rich in 1,1,1,3-tetrachloropropane—which may be used as the feedstock in step 2-a)) from that phase, e.g. via distillation. In such embodiments, where the organic phase comprises catalyst, the distillation conditions selected to extract 1,1,1,3-tetrachloropropane are mild so as to minimise deactivation of the catalyst system, for example at a temperature of about 100° C. or lower, about 95° C. or lower, about 90° C. or lower, about 85° C. or lower or about 80° C. or lower, and/or at a pressure of about 1 to 10 kPa. Lower pressures can additionally or alternatively be used.

The extracted organic phase may comprise carbon tetrachloride and/or 1,1,1,3-tetrachloropropane. Additionally, the organic phase may comprise catalyst (for example the complex of a metallic catalyst and catalyst ligand or free ligand) and/or unreacted ethylene starting material. Once a stream rich in 1,1,1,3-tetrachloropropane (which may be used as the feedstock in step 2-a) of the process of the present invention) has been extracted from the mixture formed in the aqueous treatment step (either directly, or following extraction of the organic phase therefrom), the content of 1,1,1,3-tetrachloropropane of that phase will be lower than in the reaction mixture.

In arrangements of the invention, especially those in which the organic phase comprises carbon tetrachloride and/or catalyst, the organic phase may be fed back to the alkylation zone/s, for example in liquid form. In such arrangements, ethylene starting material (e.g. in gaseous form) may be trapped in the organic phase stream being fed into the alkylation zone/s.

In embodiments of the invention, one or more distillation steps in addition to those discussed above may be performed in step 1-b), optionally to obtain stream/s rich in specific products. For example, prior to an aqueous treatment step, if performed, the reaction mixture can be subjected to a distillation step. In embodiments in which the reaction mixture contains a temperature sensitive catalyst system, e.g. one including an organic ligand as a promoter, the distillation step is typically conducted under conditions to avoid deactivation of the catalyst, for example at a temperature of about 100° C. or lower, about 95° C. or lower, about 90° C. or lower, about 85° C. or lower or about 80° C. or lower, and/or at a pressure of about 1 to 10 kPa. Lower pressures can additionally or alternatively be used.

Additionally, it has been found that the inactivation of temperature sensitive catalyst systems can be avoided by not over-distilling the reaction mixture. Thus, in embodiments of the invention in which reaction mixture containing a catalyst system is distilled in step 1-b), distillation may not be permitted to result in the volume of the process liquid in the distillation apparatus being reduced such that the concentration of the catalyst system in that process liquid is about 2×, about 5× or about 10× higher than the level of that catalyst system present in the reaction mixture provided in the principal alkylation zone.

A distillation step conducted in step 1-b) prior to the aqueous treatment step (if performed) can be carried out using techniques and equipment known to those skilled in the art, for example, a distillation boiler (batch or continuous) in communication with a vacuum distillation column. In such an embodiment, the reaction mixture subjected to distillation may comprise greater than about 50% by weight of 1,1,1,3-tetrachloropropane, catalyst, and optionally carbon tetrachloride and/or impurities, for example organic oxygenated compounds, chlorinated alkane compounds (other than 1,1,1,3-tetrachloropropane) and or chlorinated ethylene compounds.

The distillation step typically results in the removal of chlorinated alkane distillate stream/s, for example stream/s of (and optionally rich in) unreacted carbon tetrachloride, 1,1,1,3-tetrachloropropane, and/or chlorinated organic impurities (i.e. chlorinated organic compounds other than 1,1,1,3-tetrachloropropane and carbon tetrachloride) from the reaction mixture. The carbon tetrachloride may be recycled back to the alkylation zone/s. The residue from such a step, which typically comprises quantities of 1,1,1, 3-tetrachloropropane, carbon tetrachloride and/or catalyst, may be subjected to further treatment steps, e.g. an aqueous treatment step and/or further distillation step/s.

In embodiments of the invention, where the reaction mixture is subjected to a distillation step as part of step 1-b) prior to the aqueous treatment step (if performed), at least about 30%, at least about 50%, at least about 60% or at least about 70% to at most about 95%, at most about 90%, at most about 85% or at most about 80% by weight of 1,1,1,3-tetrachloropropane of interest is removed from the reaction mixture in that distillation step.

One or more distillation steps may additionally or alternatively be performed in step 1-b) following the aqueous treatment step (if performed). For example, the 1,1,1,3-tetrachloropropane extracted from the reaction mixture fed into the aqueous treatment zone may be present in the form of a mixture comprising, as the major constituent, the 1,1,1,3-tetrachloropropane, a haloalkane extraction agent, as well as chlorinated organic impurities (i.e. chlorinated organic compounds other than 1,1,1,3-tetrachloropropane and carbon tetrachloride). That mixture may be subjected to one or more distillation steps, to remove chlorinated organic impurities, to obtain a stream rich in 1,1,1,3-tetrachloropropane and/or to remove the haloalkane extraction agent. Again, any equipment or conditions known to those skilled in the art may be employed in such a distillation step, for example a distillation boiler (batch or continuous) in communication with a vacuum distillation column.

In such a distillation step, 1,1,1,3-tetrachloropropane extracted from the reaction mixture provided in the aqueous treatment zone may be subjected to distillation to separate 1,1,1,3-tetrachloropropane of interest from chloroalkane impurities. For example, a distillation step to purify 1,1,1, 3-tetrachloropropane extracted from the reaction mixture provided in the aqueous treatment zone has been found to be particularly effective in removing chloropentane/chloropentene impurities.

Chlorinated organic impurities separated from mixtures comprising 1,1,1,3-tetrachloropropane in distillation steps performed at any stage in processes of the present invention may be retrieved and re-used in the production of carbon tetrachloride. This may be achieved by subjecting the chlorinated organic impurities to a high temperature chlorinolysis process. In such a process, any chlorinated organic compounds present are re-processed mainly back to pure tetrachloromethane in high yields. Thus the use of a chlorinolysis step in the processes of the present invention is useful to maximise the overall yield of the synthesis and purity of the target chloroalkane while minimising waste production.

In embodiments of the invention, a residue of 'heavies' may be formed in a distillation boiler if used following the aqueous treatment step. The 'heavies' residue is typically extracted from the system and treated, for example, to a high temperature chlorinolysis process preferably leading to the production of chloromethanes.

Step 1) of the process of the present invention is particularly advantageous as it enables highly pure 1,1,1,3-tetrachloropropane feedstock to be produced, using simple and straightforward techniques and equipment with which one skilled in the art would be familiar.

As is apparent, step 1) of the process of the present invention as outlined above can be employed to provide highly pure 1,1,1,3-tetrachloropropane feedstocks. In embodiments of the invention, the feedstock obtained in step 1-b) of the process of the present invention comprises:

about 99.0% or more, about 99.5% or more, about 99.7% or more, about 99.8% or more or about 99.9% or more of 1,1,1,3-tetrachloropropane, less than about 2000 ppm, less than about 1000 ppm, less than about 500 ppm, less than about 200 ppm or less than about 100 ppm chlorinated alkane impurities (i.e. chlorinated alkane compounds other than the chlorinated $C_{3-6}$ alkane of interest), less than about 2000 ppm, less than about 1000 ppm, less than about 500 ppm, less than about 200 ppm or less than about 100 ppm chlorinated alkene compounds, less than about 2000 ppm, less than about 1000 ppm, less than about 500 ppm, less than about 200 ppm or less than about 100 ppm oxygenated organic compounds, less than about 500 ppm, less than about 200 ppm, less than about 100 ppm, less than about 50 ppm or less than about 20 ppm metallic catalyst, less than about 500 ppm, less than about 200 ppm, less than about 100 ppm, less than about 50 ppm or less than about 20 ppm catalyst promoter, less than about 2000 ppm, less than about 1000 ppm, less than about 500 ppm, less than about 200 ppm or less than about 100 ppm bromides or brominated organic compounds, less than about 1000 ppm, less than about 500 ppm, less than about 200 ppm, less than about 100 ppm, less than about 50 ppm or less than about 20 ppm of water, and/or about 500 ppm or less, about 200 ppm or less, about 100 ppm or less, about 50 ppm or less, about 20 ppm or less or about 10 ppm or less of one or more of Trichloromethane, 1,2-Dichloroethane, 1-Chlorobutane, 1,1,1-Trichloropropane, Tetrachloroethene, 1,1,3-Trichloroprop-1-ene, 1,1,1,3,3-Pentachloropropane, 1,1,1,2,3-

Pentachloropropane, hexachloroethane, 1,1,1,5-Tetrachloropentane, 1,3,3,5-Tetrachloropentane, Tributylphosphate, chlorinated alkanol and chlorinated alkanoyl compounds.

Step 2—Dehydrochlorination of 1,1,1,3-Tetrachloropropane to Produce 1,1,3-Trichloropropene This step of the invention involves the dehydrochlorination of 1,1,1,3-tetrachloropropane to produce 1,1,3-trichloropropene which is conducted in a dehydrochlorination zone.

It has unexpectedly been found that by controlling the level of 1,1,3-trichloropropene such that the molar ratio of that product to the 1,1,1,3-tetrachloropropane starting material does not exceed 50:50 advantageously prevents the formation of unwanted and problematic impurities, such as chlorinated oligomers which can adversely affect catalyst performance. Doing so also improves yield and catalyst activity. Advantageously, the processes of the present invention are also highly selective. Thus, in embodiments, in step 2-a) of the process of the present invention, the concentration of 1,1,3-trichloropropene in the reaction mixture present in the dehydrochlorination zone may be controlled such that the molar ratio of 1,1,3-trichloropropene:1,1,1,3-tetrachloropropane is from 1:99 to 50:50.

The molar ratio of 1,1,3-trichloropropene:1,1,1,3-tetrachloropropane in the reaction mixture formed in step 2-a) of the process of the present invention is controlled within numerically defined limits. As those skilled in the art will appreciate, in such embodiments, while control over the process is characterised herein in terms of the molar ratio between 1,1,1,3-tetrachloropropane and 1,1,3-trichloropropene, it can also be considered as control over the conversion of starting material to product—thus a molar ratio of 1,1,3-trichloropropene:1,1,1,3-tetrachloropropane of 20:80 equates to a conversion of 20%. The inventors have found that limiting the conversion 1,1,1,3-tetrachloropropane as outlined above minimises the formation of undesirable impurities and allows better catalyst lifetime. Additionally, where reference is made to a molar ratio of 1,1,3-trichlorpropene:1,1,1,3-tetrachloropropane being greater than a given value, this means a greater degree of conversion of the 1,1,1,3-tetrachloropropane to 1,1,3-trichloropropene, i.e. such that the proportion of the 1,1,3-trichloropropene is increased while the proportion of 1,1,1,3-tetrachloropropane is decreased. Moreover, the inventors have surprisingly found out that the required molar ratio between the 1,1,1, 3-tetrachloropropane product and the 1,1,3-trichloropropene starting material in the reaction mixture can be controlled not only by significantly limiting the conversion of 1,1,1,3-tetrachloropropane but, advantageously, also by efficient immediate extraction of produced 1,1,3-trichloropropene from such reaction mixture.

In embodiments of the invention the process in step 2-a) is continuous.

Step 2-a) of the process of the present invention results in the formation of 1,1,3-trichloropropene. As those skilled in the art will recognize, 1,1,3-trichloropropane is reactive and the formation of oxygenated organic compounds, such as chlorinated alkanols, or chlorinated alkanoyl compounds in dehydrochlorination reactions of this type is possible. The importance of minimising such compounds in steps 2-a) and 2-b) of the process of the present invention has been recognised by the inventors of the present process. While the exclusion of air from the apparatus can reduce the formation of oxygenated compounds, doing so is typically more technically and economically demanding, especially where sub-atmospheric pressure environments are used.

The in situ formation of such side products can be prevented through use of step 2) of the process of the present invention, and this is especially advantageous in continuous processes. The reaction conditions described herein enable 1,1,3-trichloropropene to be produced selectively and be extracted from the reaction mixture, such that there is minimised risk of the production of undesired oxygenated compounds.

Additionally or alternatively, if oxygenated compounds are formed in the process of the present invention, e.g. alkanols or carbonyl compounds, then these can be removed through the use of an aqueous treatment step in step 2-b) of the process of the present invention, discussed below in more detail.

Advantageous results have also been achieved when the content of 1,1,3-trichloropropene in the reaction mixture in step 2-a) of the present invention is controlled such that the molar ratio of 1,1,3-trichloropropene:1,1,1,3-tetrachloropropane in the reaction mixture does not exceed 40:60, 30:70, 25:75, 20:80 or 15:85. Additionally or alternatively, in embodiments of the invention, the molar ratio of 1,1,3-trichloropropene:1,1,1,3-tetrachloropropane in the reaction mixture may be equal to or greater than 2:98, 5:95 or 10:90.

Any technique or equipment may be used by those skilled in the art to determine the composition of the reaction mixture in step 2-a). For example, a direct determination of the composition can be made e.g. by providing the reaction zone with a port through which samples of the reaction mixture can be extracted for analysis and/or taking samples of reaction mixture upon extraction of that reaction mixture from the dehydrochlorination zone, e.g. via a port located at or in the vicinity of the outlet of the reaction zone. Additionally or alternatively, an indirect determination of the composition can be made e.g. by temperature control as temperature is a function of composition at constant pressure.

The level of 1,1,3-trichloropropene in the reaction mixture in step 2-a) may be controlled in one or more of the following ways: i) by removing 1,1,3-trichloropropene from the dehydrochlorination zone (either directly, or by firstly extracting reaction mixture from the dehydrochlorination zone and then extracting 1,1,3-trichloropropene therefrom), ii) control of the operating conditions in the dehydrochlorination zone (e.g. temperature, pressure, agitation speed, etc) which do not favour higher levels of 1,1,3-trichloropropene formation, and/or iii) by controlling the amount of 1,1,1,3-tetrachloropropane and/or catalyst present in the dehydrochlorination zone.

1,1,3-trichloropropene may be extracted from the reaction mixture on a continuous or batch-wise basis.

In step 2-b), 1,1,3-trichloropropene may be extracted from the reaction mixture formed in step 2-a) of the present invention using any technique known to those in the art. In embodiments, step 2-b), 1,1,3-trichloropropene is extracted from the reaction mixture via distillation. Regardless of how extraction of 1,1,3-trichloropropene from the reaction mixture is carried out, 1,1,3-trichloropropene may be obtained as a stream rich in 1,1,3-trichloropropene. This stream can be used as the feedstock in step 3-a) of the process of the present invention.

As used throughout this specification, the term 'a stream rich in' a specific compound (or corresponding language) is used to mean that the stream comprises at least about 90%, about 95%, about 97%, about 98% or about 99% of the specific compound. Further, the term 'stream' should not be interpreted narrowly, but encompasses compositions (including fractions) extracted from a mixture via any means.

For the avoidance of doubt, where reference is made to 'continuous extraction' of the reaction mixture in the dehydrochlorination zone or to reaction mixture from the dehydrochlorination zone, a strict literal interpretation is not intended; one skilled in the art would recognise that the term is used to mean that extraction occurs on a substantially continuous basis, once the dehydrochlorination zone has attained the target operating conditions and the reaction mixture has attained a steady state.

1,1,3-trichloropropene can be extracted directly from the reaction mixture in the dehydrochlorination zone (e.g. via direct distillation as part of step 2-b)), or a portion of the reaction mixture formed in step 2-a) can be firstly extracted from the dehydrochlorination zone (on a continuous or batchwise basis) and 1,1,3-trichloropropene extracted from that mixture, remotely from the dehydrochlorination zone.

In embodiments of the invention, the reaction mixture may be subjected to additional treatment steps in step 2-b), for example one or more distillation steps and/or aqueous treatment steps (discussed below in more detail). Such additional treatment steps may be carried out before and/or after extraction of 1,1,3-trichloropropene from the reaction mixture. Those skilled in the art will recognise that where such additional treatment steps are conducted post-extraction of 1,1,3-trichloropropene, the 1,1,3-trichloropropene content of the mixture will be lower than that in the reaction mixture formed in the dehydrochlorination zone.

In embodiments of the invention, in step 2-b), 1,1,3-trichloropropene may be removed from the reaction mixture by distillation. Any technique and apparatus known to those skilled in the art may be employed to effect extraction of 1,1,3-trichloropropene from the reaction mixture in this way. In embodiments of the invention, a distillation column may be used, for example a rectification column. The reaction mixture may pass or be fed into the column bottom, with 1,1,3-trichloropropene being removed from the top of the column as a liquid distillate.

For example, in embodiments, in which the reaction mixture is totally or partially gaseous, for example due to the operating temperature in the dehydrochlorination zone, the apparatus may be configured such that the dehydrochlorination zone is in fluid communication with the apparatus for conducting the distillation. In such embodiments, the distillation apparatus may be coupled to the dehydrochlorination zone. Conveniently, this enables the gaseous 1,1,3-trichloropropene-containing mixture to pass (or be passed) directly from the dehydrochlorination zone in to the distillation apparatus. Alternatively, the distillation apparatus may be located remotely from the dehydrochlorination zone, meaning that the gaseous mixture must be extracted from the dehydrochlorination zone and passed to the distillation apparatus.

Additionally or alternatively, where the reaction mixture is present in the dehydrochlorination zone either partly or totally in liquid form, a portion of the liquid reaction mixture may be extracted from the dehydrochlorination zone and passed to distillation apparatus. In such embodiments, the reaction mixture may be subjected to one or more treatment steps in step 2-b) (e.g. an aqueous treatment step, discussed below) which may precede and/or follow distillation.

In embodiments where extraction of 1,1,3-trichloropropene from the reaction mixture in step 2-b) occurs in apparatus remote from the dehydrochlorination zone, the resulting mixture, comprising unreacted 1,1,1,3-tetrachloropropane starting material and depleted levels of 1,1,3-trichloropropene (if any) may be fed back into the dehydrochlorination zone.

In embodiments in which 1,1,3-trichloropropene is extracted from the reaction mixture formed in step 2-a), at least about 30%, at least about 40%, at least about 50%, at least about 60%, at least about 70%, at least about 80%, or at least about 90% by weight of 1,1,3-trichloropropene present in the reaction mixture is extracted from that mixture.

In step 2-b), distillation of 1,1,3-trichloropropene from the reaction mixture can be carried out continuously, semi-continuously or batch-wise.

An advantage of the present invention is that the dehydrochlorination reaction produces highly pure gaseous hydrogen chloride from the reaction mixture that may be recovered using routine techniques, for example by condensation of distillation apparatus overhead vapours.

Thus, in embodiments of the invention in which hydrogen chloride is produced during the dehydrochlorination reaction (step 2-a)), the hydrogen chloride may be extracted. This can be achieved using any equipment and/or techniques for doing so known to those skilled in the art. For example, if the reaction mixture is subjected to distillation, the distillation apparatus may be provided with a condenser (e.g. a partial condenser), or a condenser (e.g. a partial condenser) may be provided downstream of the distillation apparatus, to enable the removal of hydrogen chloride gas.

Cooling apparatus (e.g. a second condenser) may additionally be employed, e.g. downstream of the first condenser. Arranging the apparatus in this way is advantageous as the first condenser can be used to condense the bulk of the 1,1,3-trichloropropene present, with the second condenser being used to purify the gas by condensing traces of 1,1,3-trichloropropene. The recovered 1,1,3-trichloropropene is highly pure (and may be used as a feedstock in step 3-a) of the process of the present invention) as is the hydrogen chloride.

Additionally or alternatively, an absorption column may be employed to absorb hydrogen chloride gas to produce hydrochloric acid solution.

In embodiments of the present invention, in which hydrogen chloride gas is extracted from the dehydrochlorination zone or from reaction mixture extracted therefrom, this may be achieved through the use of deep cooling, i.e. by extracting the gas from the reaction mixture and then cooling it to a temperature of about 0° C. or lower, about −10° C. or lower or about −20° C. or lower. The resulting condensate may be recycled back to the dehydrochlorination zone or optionally used in other associated reaction zones, e.g. hydrochlorination of glycerol.

Advantageously, hydrogen chloride extracted in these ways is highly pure and thus can be used as a reactant in upstream or downstream reactions in the same industrial plant. An example of downstream use is for the hydrochlorination of glycerol to make monochlorohydrin or dichlorohydrin, and subsequently to lead to epichlorohydrin, glycidol and epoxies.

As mentioned above, in step 2-a) of the process of the present invention, the rate of the reaction (and thus the molar ratio of 1,1,1,3-tetrachloropropane:1,1,3-trichloropropene) can be controlled by modification of the operating temperature in the dehydrochlorination zone. In embodiments of the invention, the dehydrochlorination reaction is carried out in the liquid phase, i.e. the reaction mixture is in the liquid form. In such embodiments, the dehydrochlorination zone may be operated at a temperature of about 50° C., about 60° C., about 70° C., about 80° C., about 100° C., about 120° C. or about 130° C. to about 160° C., about 170° C., about 200° C., about 250° C. or about 300° C.

In step 2-a), the reaction mixture is maintained in the dehydrochlorination zone for a period sufficient to enable the reaction (the conversion of 1,1,1,3-tetrachloropropane to 1,1,3-trichloropropene) to proceed to the required degree of completion. In embodiments of the invention, in which dehydrochlorination occurs in the liquid phase, the residence time of the reaction mixture in the dehydrochlorination zone may range from about 0.1, about 0.2, about 0.5, about 1, about 1.5, about 2, about 2.5 or about 3 to about 5 hours, about 7 hours, about 9 hours or about 10 hours.

The dehydrochlorination zone may be operated in step 2-a) at subatmospheric pressure, atmospheric pressure or superatmospheric pressure. In embodiments of the invention, the dehydrochlorination zone is operated at atmospheric pressure or a pressure of about 10 kPa to about 400 kPa, about 40 kPa to about 200 kPa, or about 70 kPa to about 150 kPa.

Any catalyst which increases the rate of the dehydrochlorination reaction may be employed in step 2-a) of the process of the present invention. In embodiments, the catalyst comprises a metal. In such embodiments, the metal may be present in solid form (e.g. where the catalyst is iron, it may be present as particulate iron (e.g. iron filings or iron powder) iron mesh, iron wire, packing (structured or random), fixed bed, fluid bed, dispersions in liquid, etc. or in alloys containing iron formed in any such way, e.g. carbon steel), and/or as a salt (e.g. where the catalyst is iron, it may be present as ferric chloride, ferrous chloride, etc). Additionally or alternatively, the apparatus in which the process of the present invention is conducted may be provided with components formed either partially or totally of catalyst material, for example column internals.

In embodiments of the invention in which metal is present in the reaction mixture as a salt, it may be added to the reaction mixture in salt form and/or solid metal may be added to the reaction mixture, which then dissolves in the reaction mixture, forming the salt in situ. When present in the form of a salt, the catalyst may be added in amorphous form, crystalline form, anhydrous form and/or in hydrated form (e.g. ferric chloride hexahydrate). Liquid form catalysts may also be employed.

In alternative embodiments, the dehydrochlorination reaction in step 2-a) is carried out in the vapour phase, i.e. both the 1,1,1,3-tetrachloropropane and the 1,1,3-trichloropropene are in gaseous form. In such embodiments, the dehydrochlorination zone may be operated at a temperature of about 300° C. to about 500° C., about 325° to about 425° C. or about 350° C. to about 400° C.

In embodiments of the invention in which the dehydrochlorination reaction occurs in the vapour phase, the residence time of the reaction mixture in the dehydrochlorination zone may range from about 0.5 to about 10 seconds.

It has been surprisingly found that, in embodiments of the invention in which the dehydrochlorination reaction in step 2-a) is carried out in the vapour phase, the reaction must be properly catalysed in order to attain high yield and selectivity. Therefore, in processes of the invention, a metallic catalyst may be used, for example one containing iron at levels of 50% by weight or greater.

Thus, in embodiments of the present invention, there is provided a process for preparing 1,1,3-trichloropropene comprising in step 2-a), contacting 1,1,1,3-tetrachloropropane in the vapour phase with a catalyst having an iron content of 50% or greater in a dehydrochlorination zone to produce a vapour-phase reaction mixture comprising 1,1,1,3-tetrachloropropane and 1,1,3-trichloropropene.

Examples of catalysts which may be employed in step 2-a) of the process of the present invention include stainless steels, for example ferritic and/or austenic steels. Catalysts employed in processes of the present invention preferably have an iron content of at least about 50%, at least about 60%, at least about 70%, at least about 80%, at least about 90% or at least about 95% by weight. Pure iron may be employed as a catalyst.

Catalysts may be employed in step 2-a) in any form, for example fluid bed arrangements and/or fixed bed arrangements. Additionally or alternatively, components of the dehydrochlorination zone comprising the catalyst can be employed. For example, in embodiments in which the dehydrochlorination zone is in a tube reactor, the reactor tubes (or at least the surfaces of those tubes in contact with 1,1,1,3-tetrachloropropane) can be formed (partially or completely) of the catalyst, or be provided with catalytic zones formed of the catalyst.

During operation of the dehydrochlorination reaction (step 2-a)) in the vapour phase of the present invention, the catalyst may become deactivated. Thus, in such embodiments, the processes of the present invention include a catalyst recovery step. This step can be achieved using any techniques and/or equipment known to those skilled in the art, for example, by the injection of an oxidant such as oxygen-rich air and/or oxygen into the dehydrochlorination zone. Prior to such a step, the flow of reactants through the dehydrochlorination zone may be stopped and/or the dehydrochlorination zone may be purged (for example with nitrogen gas). If performed, once the catalyst recovery step is completed, the dehydrochlorination zone may again be purged (for example with nitrogen gas) and/or the flow of reactants into the dehydrochlorination zone can be re-started.

In embodiments in which the dehydrochlorination step (step 2-a)) is conducted in the vapour-phase, the reaction mixture extracted from the dehydrochlorination zone is typically in the vapour phase. Those hot product gases may be condensed using any technique and/or equipment known to those skilled in the art, to obtain chlorinated organic compounds in liquid form. For example, the hot reaction mixture can be cooled by indirect cooling methods, quenching (for example using spray nozzles), direct cooling methods, or the like.

Upon cooling the gases to condense the chlorinated organic compounds from the reaction mixture, hydrogen chloride gas may be extracted which can optionally be used in upstream or downstream processes. An example of downstream use is for the hydrochlorination of glycerol to make monochlorohydrin or dichlorohydrin, and subsequently to lead to epichlorohydrin and epoxies.

Regardless of whether the dehydrochlorination step 2-a) occurs in the gaseous or liquid phase, the mixture of chlorinated organics, including 1,1,3-trichloropropene and unreacted 1,1,1,3-tetrachloropropane, as well as impurities may then be subjected to one or more post dehydrochlorination treatment steps (2-b)) as discussed herein (including one or more distillation and/or aqueous treatment steps) to obtain pure 1,1,3-trichloropropene, which may be used as a feedstock in step 3-a) of the process of the present invention.

Any type of reactor known to those skilled in the art may be employed to provide a dehydrochlorination zone in step 2-a) of the process of the present invention. Specific examples of reactors that may be used to provide a dehydrochlorination zone are column reactors, tubular reactors, bubble column reactors, plug/flow reactors and continuously stirred tank reactors.

Step 2-a) of the process of the present invention may be carried out in a single dehydrochlorination zone or in a plurality of dehydrochlorination zones. Where a plurality of dehydrochlorination zones are employed, these may be operated in sequence (i.e. such that reaction mixture is passed along a number of dehydrochlorination zones) and/or in parallel.

In embodiments of the invention, where a plurality of dehydrochlorination zones are employed in step 2-a), optionally in cascade mode, these may be in the same or different reactors. For example, where a plurality of (e.g. 1, 2, 3, 4, 5 or more) dehydrochlorination zones are employed, these may be provided in a plurality (e.g. 1, 2, 3, 4, 5 or more) of reactors (e.g. continuously stirred tank reactors) which may each be optimised to have optimised operating conditions such as temperature, residence times, In an embodiment, a plurality of dehydrochlorination zones may be present in a distillation column that may be employed in step 2-a) of the process of the present invention. In such embodiments, dehydrochlorination may be achieved by reactive distillation, for example where the dehydrochlorination reaction is carried out on trays in a distillation column and/or on packing provided in the column. In embodiments in which reactive distillation is carried out, the distillation column preferably comprises a stripping zone in which 1,1,3-trichloropropene is separated from 1,1,1,3-tetrachloropropane. The stripping zone may be located below the liquid feed.

It has been found that the components of the reaction mixture (e.g. 1,1,3-trichloropropene, hydrogen chloride and/or the starting material) obtainable from the dehydrochlorination reaction which is conducted in step 2-a) of the process of the present invention, can unfavourably interact with certain materials. Thus, in embodiments of the invention, in step 2-a), those parts of the dehydrochlorination zone which, in use, come into contact with the reaction mixture may have an iron content of about 20% or less, about 10% or less or about 5% or less, and/or are formed from non-metallic materials, for example enamel, glass, impregnated graphite (e.g. impregnated with phenolic resin), silicium carbide and/or plastics materials such as polytetrafluoroethylene, perfluoroalkoxy and/or polyvinylidene fluoride. Additionally or alternatively, at least some parts of the dehydrochlorination zone which, in use, come into contact with the reaction mixture may be formed of a nickel-based alloy, such as Hastelloy.

In embodiments of the invention, the parts of all equipment employed in the processes of the present invention with which 1,1,3-trichloropropene will contact are formed from suitable materials such as those identified above. One possible exception is where one or more regions of the surfaces of the apparatus employed in the processes of the present invention are formed of metallic material which is selected to perform as a catalyst.

The inventors have also found that, under certain operating conditions, the exposure of the reactants used in the processes of the present invention as well as the compounds formed in those processes to sources of oxygen and/or moisture, including air, water vapour and/or water can lead to the formation of unwanted impurities. Thus, in embodiments of the present invention, dehydrochlorination and/or distillation may be conducted in an inert atmosphere, e.g. in the absence of oxygen.

In step 2-a) of the process of the present invention, 1,1,1,3-tetrachloropropane may be fed into the dehydrochlorination zone using any technique known to those skilled in the art.

The 1,1,1,3-tetrachloropropane feedstock employed in step 2-a) of the process of the present invention preferably has a purity level of at least about 95%, at least about 97%, at least about 98%, at least about 98.5%, at least about 99%, or at least about 99.5%.

In embodiments, the 1,1,1,3-tetrachloropropane feedstock contains less than or equal to about 1000 ppm, less than or equal to about 500 ppm, less than or equal to 250 ppm or less than or equal to about 100 ppm of chlorinated alkane impurities, for example alkanes having a boiling point which is equal to or greater than the boiling point 1,1,1,3-tetrachloropropane and/or 1,1,3-trichloropropene and/or which, in the reaction conditions are dehydrochlorinated to produce a chlorinated alkene impurity, for example alkenes which have a boiling point within 10° C. of 1,1,3-trichloropropene, which have a boiling point equal to or greater than 1,1,1,3-tetrachloropropane, and/or which are isomers of 1,1,3-trichloropropene.

In additional or alternative embodiments, the 1,1,1,3-tetrachloropropane feedstock contains less than or equal to about 1000 ppm, less than or equal to about 500 ppm, less than or equal to 250 ppm or less than or equal to about 100 ppm of chlorinated alkene impurities, for example alkenes which have a boiling point within 10° C. of 1,1,3-trichloropropene, which have a boiling point equal to or greater than 1,1,1,3-tetrachloropropane, or 1,1,3-trichloropropene, and/or which are isomers of 1,1,3-trichloropropene.

Additionally or alternatively, the 1,1,1,3-tetrachloropropane feedstock comprises less than or equal to about 1000 ppm, less than or equal to about 500 ppm, less than or equal to about 200 ppm, less than or equal to about 100 ppm, less than or equal to about 50 ppm, less than or equal to about 20 ppm or less than or equal to about 10 ppm of tetrachloroethene, hexachloroethane and/or tetrachloropentanes.

One of the advantages of step 2-a) of the process of the present invention is that it permits the production of 1,1,3-trichloropropene with high isomeric selectivity. Thus, in embodiments of the invention, 1,1,3-trichloropropene is produced in step 2-a) with isomeric selectivity of at least about 95%, at least about 97%, at least about 98%, at least about 99%, at least about 99.5%, at least about 99.7%, at least about 99.8% or at least about 99.9%.

The feed of 1,1,1,3-tetrachloropropane and/or catalyst into the dehydrochlorination zone may be continuous or intermittent, as may extraction of the reaction mixture.

A further advantage of step 2-a) of the process of the present invention is that desirous results are obtained whether the dehydrochlorination zone is operated in a continuous or batch process. The terms 'continuous process' and 'batch process' will be understood by those skilled in the art.

A still further advantage of step 2-a) of the process of the present invention is that it enables high purity 1,1,3-trichloropropene to be produced without the use of alkaline hydroxides. Thus, in embodiments or the present invention, no alkaline hydroxide is added to the dehydrochlorination zone in step 2-a) and/or the reaction medium present in the dehydrochlorination zone in step 2-a) is free of alkaline hydroxide.

As mentioned above, in embodiments of the invention, reaction mixture comprising 1,1,1,3-tetrachloropropane, 1,1,3-trichloropropene and catalyst may be extracted from the dehydrochlorination zone. This may be subjected to further treatment steps in step 2-b).

In such embodiments, such a treatment step may be an aqueous washing step in which the extracted mixture is optionally filtered and then fed into an aqueous treatment zone. This step may be carried out before or after extraction of 1,1,3-trichloropropene from the mixture.

The mixture is contacted with an aqueous medium in the aqueous treatment zone which serves to deactivate the catalyst. The mixture may be contacted with acid in the aqueous treatment zone, for example inorganic acid such as sulphuric acid, phosphoric acid and/or hydrochloric acid. The acid may be pure, or may be dilute. Where dilute acid is used, this may provide the aqueous medium. The pH value of the aqueous medium should be sufficiently low to enable effective separation of the biphasic mixture.

The aqueous treatment step comprised in step 2-b) has the advantageous effect of removing certain classes of otherwise problematic impurities from the mixture, especially oxygenated impurities.

In such embodiments, catalyst deactivation can be achieved with only a short contact time, e.g. about 5, about 10, about 20 or about 30 minutes, with water at low temperature being required. For hydrolysis and extraction of chlorinated, oxygenated impurities, the contact time with the water may be longer, e.g. up to about 1 hour, about 2 hours, about 5 hours or about 10 hours and/or at a temperature of about 50° C. or less, about 40° C. or less or about 30° C. or less.

Thus, in embodiments of the invention, step 2-b) of the inventive process may comprise the step of removing oxygenated organic impurities from a mixture comprising 1,1,3-trichloropropene, oxygenated organic impurities and optionally a catalyst and/or 1,1,1,3-tetrachloropropane, comprising contacting the mixture with an aqueous medium to form a biphasic mixture and extracting the organic phase from that biphasic mixture. In embodiments of the invention, the mixture of this aspect of the invention is or comprises the mixture extracted from the dehydrochlorination zone employed in step 2-a).

Where a dilute acid is employed in such a step, this may additionally provide the aqueous medium with which the mixture is contacted. Additionally, or alternatively, the aqueous medium may comprise water (in any form, e.g. including steam) which may be added separately into the aqueous treatment zone.

In embodiments in which acid is added into the aqueous treatment zone, this preferably reduces the pH of the mixture present therein to about 6 or lower, about 5 or lower, about 4 or lower, about 2 or lower or about 1 or lower.

A proportion (e.g. at least about 30%, at least about 40%, at least about 50%, at least about 60%, at least about 70%, or at least about 80%) of the unreacted 1,1,1,3-tetrachloropropane and/or 1,1,3-trichloropropene may be extracted from the mixture formed in the aqueous treatment zone using any techniques or equipment known to those skilled in the art.

For example, in embodiments in which the mixture is partly or totally in gaseous form, for example due to the operating temperature in the aqueous treatment zone and/or through the addition of steam as the aqueous medium, the gaseous mixture may be subjected to distillation in step 2-b). In such embodiments, the distillation device may be in fluid communication with the aqueous treatment zone (optionally coupled to that zone) or may be remote from the aqueous treatment zone.

Additionally or alternatively, where the mixture is partly or totally in liquid form, that mixture may be extracted from the aqueous treatment zone and subjected to distillation in step 2-b).

In embodiments where such a distillation step is conducted in step 2-b), a stream comprising (and optionally rich in) 1,1,1,3-tetrachloropropane and/or 1,1,3-trichloropropene may be obtained. The stream rich in 1,1,3-trichloropropene may be used as the feedstock in step 3-a) of the process of the present invention.

1,1,1,3-tetrachloropropane and/or 1,1,3-trichloropropene extracted from the mixture fed in to the aqueous treatment zone may be recycled back to the dehydrochlorination zone for use as a starting material.

A biphasic mixture, comprising an aqueous phase and an organic phase may be formed in the aqueous treatment zone (or in certain embodiments, remotely therefrom) in step 2-b), as a result of the presence of both the aqueous medium and also the predominantly organic mixture, In such embodiments where a biphasic mixture is formed in step 2-b) of the process of the present invention, the organic phase may be extracted from the biphasic mixture using phase separation techniques and/or equipment known to those skilled in the art. Where the biphasic mixture is formed in the aqueous treatment zone, the organic phase can be separated from the aqueous phase by the sequential extraction of the phases from the aqueous treatment zone. The aqueous phase, which contains impurities removed from the mixture can be further treated.

To maximise phase separation efficiency and thus facilitate extraction of that phase from the biphasic mixture, a haloalkane extraction agent and/or phase separation intensifier (for example, 1,1,1,3-tetrachloropropane and/or various alcohols and/or ketones) may be added to the aqueous treatment zone, either intermittently or continuously, using techniques and/or equipment known to those skilled in the art. The use of 1,1,1,3-tetrachloropropane is preferred as this compound is part of the process and thus does not require removal using specific separation steps.

Optionally, phase separation intensifiers such as polar alcohols and/or ketones with boiling points sufficiently different to 1,1,3-trichloropropene and 1,1,1,3-tetrachloropropane may be employed. The difference in boiling points should be at least 20° C., at least about 30° C., at least about 40° C., at least about 50° C. or at least about 60° C. Examples of phase separation intensifiers that may be employed include aliphatic ketones e.g. acetone and aliphatic alcohols e.g. methanol, ethanol, propanol/s, butanol/s.

In embodiments of the invention, the extracted organic phase may then be subjected to a distillation step in step 2-b) in which streams of (and optionally rich in) 1,1,3-trichloropropene and/or unreacted 1,1,1,3-tetrachloropropane are distilled off. Such a step may be performed regardless of whether extraction of 1,1,3-trichloropropene from the reaction mixture was carried out prior to aqueous treatment or not. The stream of unreacted 1,1,1,3-tetrachloropropane may be recycled back to the dehydrochlorination zone. The stream rich in 1,1,3-trichloropropene may be used as the feedstock in step 3-a) of the process of the present invention. A heavy ends residue may be extracted from the distillation apparatus, optionally filtered and incinerated and/or subjected to high temperature chlorinolysis.

The organic phase comprising 1,1,1,3-tetrachloropropane and/or 1,1,3-trichloropropene as well as haloalkane extraction agent and/or phase separation intensifier may be fed back in to the dehydrochlorination zone. In such embodiments, a distillation step to remove the phase separation intensifier (if used) or other components of the organic phase may be conducted.

Reducing the water content of the chlorinated alkene has been found to use such alkene in downstream applications such as chlorination. Thus, in embodiments of the present invention, the process conditions are controlled such that the obtained chlorinated alkene product/s comprise less than about 500 ppm, about 200 ppm or less, about 100 ppm or less or about 50 ppm or less of water.

Step 2) of the present invention is advantageous as it enables highly pure 1,1,3-trichloropropene to be produced using simple and straightforward techniques and equipment with which one skilled in the art would be familiar.

Step 2) of the process of the present invention results in the production of the 1,1,3-trichloropropene feedstock for use in step 3-a) of the process. That feedstock preferably comprises:
- about 95% or more, about 97% or more, about 99% or more, about 99.2% or more about 99.5% or more or about 99.7% or more of 1,1,3-trichloropropene,
- less than about 50000 ppm, less than about 20000 ppm, less than about 10000 ppm, less than about 5000 ppm, less than about 2000 ppm, less than about 1000 ppm, less than about 500 ppm, less than about 200 ppm, or less than about 100 ppm of 1,1,1,3-tetrachloropropane,
- less than about 1000 ppm, less than about 500 ppm, less than about 200 ppm, or less than about 100 ppm of chlorinated $C_{5-6}$ alkane impurities,
- less than about 1000 ppm, less than about 500 ppm, less than about 200 ppm, or less than about 100 ppm of chlorinated alkene impurities (i.e. chlorinated alkenes other than 1,1,3-trichloropropene),
- less than about 500 ppm, less than about 200 ppm, less than about 100 ppm, less than about 50 ppm, less than about 20 ppm, less than about 10 ppm or less than about 5 ppm metal,
- less than about 1000 ppm, less than about 500 ppm, less than about 250 ppm, or less than about 100 ppm of oxygenated organic compounds, and/or
- less than about 500 ppm, about 250 ppm or less, about 100 ppm or less or about 50 ppm or less of water.

Step 3—Chlorination of 1,1,3-Trichloropropene to Produce 1,1,1,2,3-Pentachloropropane The process of this step of the present invention involves the chlorination of an already chlorinated alkene (1,1,3-trichloropropene) to produce 1,1,1,2,3-pentachloropropane with a high level of purity. The process is highly selective.

It has been found that controlling the degree of conversion of the 1,1,3-trichloropropene starting material to the 1,1,1,2,3-pentachloropropane product advantageously minimises the formation of unwanted impurities. Thus, in embodiments of the invention, in step 3-a) of the process, the molar ratio of 1,1,1,2,3-pentachloropropane:1,1,3-trichloropropene in the reaction mixture extracted from the reaction zone does not exceed 95:5.

The molar ratio of 1,1,1,2,3-pentachloropropane:1,1,3-trichloropropene in the reaction mixture is controlled within numerically defined limits. As those skilled in the art will appreciate, in such embodiments, while control over the process is characterised herein in terms of the molar ratio between 1,1,1,2,3-pentachloropropane and 1,1,3-trichloropropene, it can also considered as control over the conversion of 1,1,3-trichloropropene to 1,1,1,2,3-pentachloropropane—thus a molar ratio of 1,1,1,2,3-pentachloropropane:1,1,3-trichloropropene of 95:5 equates to a conversion of 95%. The inventors have found that, in step 3-a) of the process of the present invention, limiting the conversion of the starting material as outlined above minimises the formation of undesirable impurities. Additionally, where reference is made to a molar ratio of 1,1,1,2,3-pentachloropropane:1,1,3-trichloropropene being greater than a given value, this means a greater degree of conversion of the 1,1,3-trichloropropene to 1,1,1,2,3-pentachloropropane, i.e. such that the proportion of 1,1,1,2,3-pentachloropropane is increased while the proportion of 1,1,3-trichloropropene is decreased.

In embodiments of the invention, the reaction zone may be a primary reaction zone.

One of the advantages of step 3-a) of the process of the present invention is that it permits the production of 1,1,1,2,3-pentachloropropane with high isomeric selectivity. Thus, in embodiments of the invention, 1,1,1,2,3-pentachloropropane is produced in step 3-a) with isomeric selectivity of at least about 95%, at least about 97%, at least about 98%, at least about 99%, at least about 99.5%, at least about 99.7%, at least about 99.8% or at least about 99.9%.

It has been found that highly pure 1,1,1,2,3-pentachloropropane is less susceptible to degradation during storage and transport. It is believed that this is due to the absence (or presence in only trace amounts) of impurities which would otherwise trigger decomposition of 1,1,1,2,3-pentachloropropane. Accordingly, the use of stabilising agents can advantageously be avoided.

A further advantage of step 3-a) of the process of the present invention is that, through control of the degree of conversion of the starting material to product, the formation of otherwise problematic serial products is minimised. Accordingly, in embodiments of the invention, reaction mixture extracted from the primary reaction zone, and/or 1,1,1,2,3-pentachloropropane rich material extracted from the principal reaction zone, comprises low levels of serial reaction products, i.e. compounds comprising a greater number of chlorine and/or carbon atoms 1,1,1,2,3-pentachloropropane, for example in amounts of less than about 5%, less than about 2%, less than about 1%, less than about 0.5%, less than about 0.2%, less than about 0.1%, less than about 0.05% or less than about 0.02%.

In embodiments of the invention, the process may be continuous.

It has unexpectedly been found that through the careful control of the level of 1,1,1,2,3-pentachloropropane in the reaction mixture formed in the primary reaction zone in step 3-a), the production of impurities is minimised, and/or high selectivity for 1,1,1,2,3-pentachloropropane, is achieved. The level of 1,1,1,2,3-pentachloropropane in the reaction mixture may be controlled by, for example, i) removing 1,1,1,2,3-pentachloropropane (either specifically, or by extracting reaction mixture) from the primary reaction zone/s, ii) by controlling the reaction conditions in the primary reaction zone (e.g. temperature, exposure to light, and/or pressure), and/or iii) by controlling the amount of 1,1,3-trichloropropene and/or chlorine present in the primary reaction zone.

For example, the amount of chlorine present in the reaction mixture formed in step 3-a) of the process of the present invention can be controlled such that there is no molar excess of chlorine present in the reaction mixture in the primary and/or principal reaction zone/s.

Any conditions which result in the formation of 1,1,1,2,3-pentachloropropane may be employed in the primary reaction zone used in step 3-a). However, in embodiments of the invention, the operating temperature in the primary reaction zone is maintained at a relatively low level, for example about 100° C. or lower, about 90° C. or lower or about 80° C. or lower. The operating temperature of the primary reaction zone may be about −30° C., about −20° C., about −10° C. or about 0° C. to about 20° C., about 40° C., or about 75° C. The use of such temperatures in the primary reaction zone has been found unexpectedly to be advantageous as this results in a reduction in the formation of isomers of 1,1,1,2,3-pentachloropropane and over-chlorinated compounds, yet gives the required product selectively in high yield. To increase the reaction rate at these temperatures, light (visible and/or ultra violet) may optionally be used to promote the addition of chlorine at these low temperatures.

In step 3-a), the operating temperature in the primary reaction zone may be controlled by any temperature control means known to those skilled in the art, for example heating/cooling jackets, heating/cooling loops either internal or external to the reactor, heat exchangers and the like. Additionally or alternatively, the temperature may be controlled by controlling the temperature of material/s added into the reaction mixture, thus, controlling the temperature of the reaction mixture. The reaction mixture is maintained in the primary reaction zone for a time and under conditions sufficient to achieve the required level of 1,1,1,2,3-pentachloropropane in the reaction mixture.

In embodiments of the invention, the primary reaction zone employed in step 3-a) may be exposed to light, for example visible light and/or ultra violet light. Exposure of the reaction mixture to light promotes the reaction when operated at low temperatures which is advantageous where the use of higher temperatures is to be avoided.

For the avoidance of doubt, in embodiments of the invention, the primary conversion step in step 3-a) may be carried out in a plurality of primary reaction zones (e.g. 1, 2, 3, 4, 5, 6, 7, 8, 9, 10 or more primary reaction zones), which may be operated at the same or different pressures, temperatures and/or light conditions.

In step 3-a) of the process of the present invention, the residence time of the reaction mixture in the primary reaction zone may range from about 30 to 300 minutes, from about 40 to about 120 minutes or from about 60 to about 90 minutes.

Optimal results have been observed when the level of 1,1,1,2,3-pentachloropropane in the reaction mixture present in the primary reaction zone is maintained at a level such that the molar ratio of 1,1,1,2,3-pentachloropropane:1,1,3-trichloropropene in reaction mixture extracted from the primary reaction zone does not exceed 50:50. In embodiments of the invention, the level of 1,1,1,2,3-pentachloropropane present in the reaction mixture in the primary reaction zone may be maintained at lower levels, for example such that the molar ratio of 1,1,1,2,3-pentachloropropane:1,1,3-trichloropropene in reaction mixture extracted from the primary reaction zone does not exceed 75:25, 50:50, 40:60 or 30:70. Additionally or alternatively, the level of 1,1,1,2,3-pentachloropropane in the reaction mixture present in the primary reaction zone/s is maintained at a level such that the molar ratio of 1,1,1,2,3-pentachloropropane:1,1,3-trichloropropene in reaction mixture extracted from the primary reaction zone is at least 5:95, 10:90, 15:85, 20:80, 30:70, 40:60 or 50:50.

The composition of reaction mixture, enabling a determination of the molar ratio of 1,1,1,2,3-pentachloropropane:1,1,3-trichloropropene, may be determined as soon as is practicable following extraction of the reaction mixture from the primary reaction zone. For example, a sample of reaction mixture may be extracted at a point adjacent to or slightly downstream of the outlet of the primary reaction zone. In embodiments of the invention, the outlet may be located at the upper end of the primary reaction zone.

Reaction mixture comprising 1,1,3-trichloropropene and 1,1,1,2,3-pentachloropropane formed in step 3-a) of the process of the present invention may be extracted from the primary and/or principal reaction zone. This may be done either continuously or intermittently.

One skilled in the art would recognise that, in embodiments where reaction mixture/1,1,1,2,3-pentachloropropane rich product is extracted from the respective reaction zone, that material may be removed on a substantially continuous basis while the zone in question is at operating conditions and, if its purpose is to set up a steady state reaction (e.g. a chlorination), once the reaction mixture therein has attained the required steady state.

In embodiments of the present invention, the reaction in step 3-a) conducted in the primary reaction zone is in the liquid phase, i.e., the reaction mixture present therein is predominantly or totally liquid. The reaction mixture may be analysed using any techniques known to those skilled in the art e.g. chromatography.

The 1,1,3-trichloropropene feedstock used in step 3-a) of the process of the present invention preferably has a high degree of purity. In embodiments of the invention, the 1,1,3-trichloropropene feedstock has a purity level of at least about 95%, at least about 97%, at least about 99%, or at least about 99.5%.

Additionally or alternatively, the 1,1,3-trichloropropene feedstock used in step 3-a) of the process of the present invention may include less than about 2%, less than about 1%, less than about 0.1%, less than about 0.01% or less than about 0.001% by weight of chlorinated alkene and/or chlorinated alkane impurities. For example, the 1,1,3-trichloropropene feedstock may comprise less than about 2%, less than about 1%, less than about 0.1%, less than about 0.01% or less than about 0.001% by weight of chlorinated alkene impurities such as perchlorethylene, tetrachloroethylene, hexachloroethylene, isomeric trichloropropene, tetrachloropropenes and/or chlorinated alkane impurities such as 1,1,1,3-tetrachloropropane.

The feed of chlorine and/or 1,1,3-trichloropropene into the primary reaction zone/s and/or principal reaction zone/s employed in step 3-a) of the process of the present invention may be continuous or intermittent.

Chlorine may be fed into reaction zone/s employed in step 3-a) of the process of the present invention in liquid and/or gaseous form, either continuously or intermittently. For example, the primary reaction zone may be fed with one or more chlorine feeds. Additionally or alternatively, reaction zone/s downstream of the primary reaction zone (e.g. the principal conversion zone) may be fed with one or more chlorine feeds. In embodiments of the invention, the only reaction zone supplied with chlorine is the primary reaction zone.

Where the reaction mixture in the reaction zone/s is liquid, the chlorine may be fed into the reaction zone/s as gas and dissolved in the reaction zone. In embodiments, the chlorine is fed into reaction zone/s via dispersing devices, for example, nozzles, porous plates, tubes, ejectors, etc. The chlorine, in embodiments of the invention, may be fed directly into the liquid reaction mixture. Additionally or alternatively, the chlorine may be fed into liquid feeds of other reactants upstream of the reaction zone/s.

Additional vigorous stirring may be used to ensure good mixing and/or dissolution of the chlorine into the liquid reaction mixture.

The chlorine used as a starting material in step 3-a) of the process of the present invention is preferably highly pure. In embodiments of the invention, the chlorine fed into the reaction zone/s employed at any stage in the present invention preferably has a purity of at least about 95%, at least about 97%, at least about 99%, at least about 99.5%, or at least about 99.9%

Additionally or alternatively, the chlorine used in step 3-a) of the process of the present invention may comprise bromine or bromide in an amount of about 200 ppm or less, about 100 ppm or less, about 50 ppm or less, about 20 ppm or less or about 10 ppm or less.

The use of chlorine gas comprising low amounts of oxygen (e.g. about 200 ppm or less, about 100 ppm or less, about 50 ppm or less, about 20 ppm or less or about 10 ppm or less) is also envisaged. However, in embodiments of the present invention, lower grade chlorine (including higher oxygen levels, e.g. of 1000 ppm or higher) can advantageously be employed in step 3-a) without the product of the processes of the present invention comprising unacceptably high levels of oxygenated impurities.

As mentioned above, it is envisaged that in embodiments of the invention, the reaction mixture produced in step 3-a) in the primary reaction zone will be liquid. However, alternative embodiments are envisaged in which the reaction mixture is gaseous. In such embodiments, the primary reaction zone may be operated at temperatures of about 150° C. to about 200° C. Gas phase reactors, for example, one or more tubular gas phase reactors, may be employed in such embodiments.

The term 'highly pure' as used in the context of step 3) of the process of the present invention means about 95% or higher purity, about 99.5% or higher purity, about 99.7% purity, about 99.8% or higher purity, about 99.9% or higher purity, or about 99.95% or higher purity. Unless otherwise specified, values presented herein as percentages are by weight.

Extraction of the reaction mixture from the primary reaction zone can be achieved using any technique known to those skilled in the art. Typically, reaction mixture extracted from the primary reaction zone will comprise unreacted 1,1,3-trichloropropene, unreacted chlorine and 1,1,1,2,3-pentachloropropane. Alternatively, where control of the formation of 1,1,1,2,3-pentachloropropane is achieved by controlling (i.e. limiting) the amount of chlorine fed into the primary reaction zone, the reaction mixture extracted from the primary reaction zone may comprise very low levels of chlorine, for example about 1% or less, about 0.5% or less, about 0.1% or less, about 0.05% or less or about 0.01% or less.

In embodiments of the invention, where reaction mixture comprising unreacted 1,1,3-trichloropropene is extracted from the primary reaction zone, a principal conversion step may be performed in step 3-a) in which majority significant proportion, but not all, of the unreacted 1,1,3-trichloropropene present in the reaction mixture extracted from the primary reaction zone is converted to 1,1,1,2,3-pentachloropropane, thus producing a 1,1,1,2,3-pentachloropropane rich product, which is then extracted from the principal reaction zone. The 1,1,1,2,3-pentachloropropane rich product may comprise unreacted 1,1,3-trichloropropene starting material and 1,1,1,2,3-pentachloropropane product.

In such embodiments, the reaction mixture may additionally comprise chlorine. Additionally or alternatively, chlorine may be fed into the principal reaction zone to enable the chlorination reaction to proceed.

The degree of conversion 1,1,3-trichloropropene to 1,1,1,2,3-pentachloropropane is controlled such that the molar ratio of 1,1,1,2,3-pentachloropropane:1,1,3-trichloropropene present in the 1,1,1,2,3-pentachloropropane rich product extracted from the principal reaction zone does not exceed about 95:5, about 93:7, about 91:9, about 90:10 or about 87.5:12.5.

Additionally or alternatively, the degree of conversion of 1,1,3-trichloropropene to 1,1,1,2,3-pentachloropropane is controlled such that the molar ratio of 1,1,1,2,3-pentachloropropane:1,1,3-trichloropropene present in the 1,1,1,2,3-pentachloropropane rich product extracted from the principal reaction zone is greater than about 70:30, about 75:25, about 80:20 or about 85:15.

In certain embodiments of step 3-a) of the process of the present invention in which a principal reaction step is carried out, the molar ratio of 1,1,1,2,3-pentachloropropane:1,1,3-trichloropropene present in the 1,1,1,2,3-pentachloropropane rich product extracted from the principal reaction zone is greater than that for reaction mixture extracted from the primary reaction zone. In other words, the degree of conversion of the starting material to product is higher for the product extracted from the principal reaction zone than for the reaction mixture extracted from the primary reaction zone.

In step 3-a) of the process of the present invention, where a 1,1,1,2,3-pentachloropropane rich product is employed or produced, it may have the 1,1,1,2,3-pentachloropropane:1,1,3-trichloropropene ratios outlined above.

It has unexpectedly been found that through the careful control of the degree of conversion of 1,1,3-trichloropropene in the principal reaction zone, the production of impurities is minimised in step 3-a) of the process of the present invention. The level of 1,1,1,2,3-pentachloropropane in the reaction mixture may be controlled by, for example, i) removing the 1,1,1,2,3-pentachloropropane (either specifically, or by extracting 1,1,1,2,3-pentachloropropane rich product) from the principal reaction zone, ii) by controlling the reaction conditions in the principal reaction zone (e.g. temperature, exposure to light, and/or pressure), and/or iii) by controlling the amount of 1,1,3-trichloropropene and/or chlorine present in the principal reaction zone.

In embodiments of the invention in which the degree of conversion of 1,1,3-trichloropropene to 1,1,1,2,3-pentachloropropane is controlled (i.e. limited) in step 3-a) by controlling the amount of chlorine present in the principal reaction zone (e.g. supplied directly thereto and/or present as a component of the reaction mixture), the chlorine content in the obtained 1,1,1,2,3-pentachloropropane rich product may be very low, for example about 1% or less, about 0.5% or less, about 0.1% or less, about 0.05% or less or about 0.01% or less.

This principal conversion step will typically take place in one or more principal reaction zones downstream of the primary reaction zone. Any number of principal reaction zones may be employed in the processes of the present invention, for example 1, 2, 3, 4, 5, 6, 7, 8, 9, 10 or more principal reaction zones.

Any conditions which result in the conversion of 1,1,3-trichloropropene to 1,1,1,2,3-pentachloropropane may be employed in the principal conversion step in step 3-a) of the process of the present invention. In embodiments of the invention, the principal conversion step may comprise a reduced temperature conversion step. When such a step is performed, the reduction in temperature of the extracted reaction mixture is preferably achieved by feeding the reaction mixture into a principal reaction zone operated at a reduced temperature (for example about −30 to about 30° C., about −25 to about 10° C., or more preferably about −20 to about −10° C.) and extracting a 1,1,1,2,3-pentachloropropane rich product from the principal conversion zone.

It has been unexpectedly found that in step 3-a), maintaining, at low temperature, a reaction mixture comprising 1,1,3-trichloropropene, chlorine and 1,1,1,2,3-pentachloropropane, results in the conversion of 1,1,3-trichloropropene to 1,1,1,2,3-pentachloropropane while minimising the production of unwanted impurities, improving selectivity and/or the yield.

Thus, in step 3-a) of the process of the present invention, a reduced temperature conversion step may be performed in which a reaction mixture comprising 1,1,3-trichloropropene, and 1,1,1,2,3-pentachloropropane is fed into a principal reaction zone, operated at a temperature of about −30° C. to about 30° C., about −25° C. to about 10° C., or more preferably about −20° C. to about −10° C., and a 1,1,1,2,3-pentachloropropane rich product may then be extracted from the principal reaction zone.

For certain embodiments of step 3-a), exposure of the reaction mixture in the principal reaction zone to light (for example ultra violet light) is useful in conducting the reaction successfully at low temperatures.

In aspects of the invention, in step 3-a), the ratio of 1,1,1,2,3-pentachloropropane:1,1,3-trichloropropene present in the reaction mixture fed in to the principal reaction zone may be 70:30 or lower, 60:40 or lower, 50:50 or lower, 40:60 or lower or 30:70 or lower and/or 5:95 or higher, 10:90 or higher, 20:80 or higher or 40:60 or higher.

In embodiments of the invention, in step 3-a), the operating temperature of the principal reaction zone may be achieved in a single cooling action, or a series of cooling actions in which the principal reaction zone/s are operated at successively lower temperatures. Operating the principal reaction zone/s at reduced temperature can be achieved using any technique known to those skilled in the art.

The reduced temperature conversion step in step 3-a) preferably takes place in one or more principal reaction zones downstream of the primary reaction zone. For example, where the reduced temperature conversion step requires a single cooling action, it may occur in a single principal reaction zone. Where the reduced temperature conversion step requires a series of cooling actions, this may be achieved in a single principal reaction zone, or in a plurality of principal reaction zones.

In embodiments of the present invention, in step 3-a), the reaction mixture is maintained in the principal reaction zone for a time and under conditions sufficient to achieve the required level of 1,1,1,2,3-pentachloropropane in the reaction mixture.

The principal reaction zone/s may be operated under subatmospheric, atmospheric or superatmospheric pressure. Additionally or alternatively, the primary and/or the principal reaction zone/s may be exposed to light, for example visible light and/or ultra violet light.

In embodiments of the present invention, in step 3-a), the residence time of the reaction mixture in the principal reaction zone may range from about 30 to 300 minutes, from about 40 to about 120 minutes or from about 60 to about 90 minutes.

In embodiments of the present invention, the reaction conducted in the principal reaction zone is in the liquid phase, i.e, the reaction mixture present therein is predominantly or totally liquid.

In embodiments of the invention, in step 3-a) reaction mixture extracted from the primary reaction zone is subjected directly to the principal conversion step. In alternative embodiments, the extracted reaction mixture is subjected to one or more pre-treatment steps prior to being subjected to the principal conversion step.

In embodiments of the invention, to attain the desired level of 1,1,1,2,3-pentachloropropane in the 1,1,1,2,3-pentachloropropane rich product, the principal conversion step may involve heating the 1,1,1,2,3-pentachloropropane rich product to elevated temperatures, for example to about 20° C. or higher, about 30° C. or higher, about 40° C. or higher, about 50° C. or higher or about 60° C. or higher.

Heating the 1,1,1,2,3-pentachloropropane rich product in this way may be achieved in a single heating step. Alternatively, the 1,1,1,2,3-pentachloropropane rich product may be subjected to a series of heating steps at successively higher temperatures.

As mentioned above, in step 3-a) of the process of the present invention, different reaction zones may be operated at different temperatures, pressure and/or to the exposure to differing types and/or intensity of light. For example, reaction mixture extracted from the primary reaction zone/s could be passed into a first principal reaction zone in which a reduced temperature conversion step is carried out. The obtained 1,1,1,2,3-pentachloropropane rich product could then be passed into a second principal reaction zone downstream of the first principal reaction zone in which a heat treatment or UV exposure step is performed, to convert the bulk of the remaining unreacted 1,1,3-trichloropropene present to 1,1,1,2,3-pentachloropropane. Alternatively, the reduced-temperature conversion step and heating and/or UV exposure steps could all take place in the principal reaction zone.

Thus, in step 3-a) of the process of the invention, a plurality of principal reaction zones may be employed in sequence. For ease of comprehension, these may be characterised as upstream principal reaction zones and downstream principal reaction zones, the upstream principal reaction zones being upstream of the downstream principal reaction zones when those zones are operated in sequence.

In such embodiments, there may be any number of upstream principal reaction zones and/or downstream principal reaction zones, for example 1, 2, 3, 4, 5, 6, 7, 8, 9 or 10 or more upstream principal reaction zones and/or downstream principal reaction zones.

Where such arrangements are employed, heat treatment and/or light (e.g. ultraviolet light) exposure may be conducted in some or all of the upstream and/or downstream principal reaction zones. The intensity of the light exposure may be higher in the downstream principal reaction zones. Additionally or alternatively, the wavelength of the light to which the reaction mixture is exposed in the downstream principal reaction zones may be lower than that in the upstream principal reaction zones.

In certain embodiments of the invention, heat treatment and/or light exposure steps may only be conducted in the downstream principal reaction zones.

One advantage of step 3-a) of the process of the present invention is that desirous results are obtained whether the primary and/or principal reaction zones are operated in a continuous or batch process. The terms 'continuous process' and 'batch process' will be understood by those skilled in the art.

Any type of reactor known to those skilled in the art may be employed in step 3-a) of the process of the present invention. Specific examples of reactors that may be used to provide primary reaction zone/s and/or principal reaction zone/s are column reactors (e.g. column gas-liquid reactors), tubular reactors (e.g. tubular gas phase reactors), bubble column reactions, plug/flow reactors and stirred tank reactors, for example continuously stirred tank reactors.

Reactors used in step 3-a) of the present invention may be divided into different zones each having different flow patterns and/or different operating temperatures/pressures. For example, the principal conversion step may be performed in a reactor including a plurality of principal reaction zones. Those zones may be operated at different temperatures and/or pressures. For example, in embodiments where the principal conversion step is a reduced temperature conversion step, the principal reaction zones may be operated at successively lower temperatures.

Additionally or alternatively, reactors used in step 3-a) of the process of the present invention may be provided with external circulation loops. The external circulation loops may optionally be provided with cooling and/or heating means.

As those skilled in the art will recognise, in step 3-1), reaction zones can be maintained at differing temperatures through use of cooling/heating elements such as cooling tubes, cooling jackets, cooling spirals, heat exchangers, heating fans, heating jackets or the like.

Some or all of the primary and/or principal reaction zones used in step 3-a) of the process of the present invention may be exposed to visible light (natural or artificially generated), ultra violet light and/or be operated in darkness.

Chlorine, either in liquid, in solution, and/or gaseous form, may be fed into the principal reaction zone/s. 1,1,3-trichloropropene may also or alternatively be fed into the principal reaction zone/s, if required.

Those skilled in art will recognise that, in certain embodiments, the reaction zones utilised at any stage in the processes of the present invention may require agitation means, e.g. stirrers, followers, flow channeling means or the like and the use of such means in the primary and/or principal reaction zones in the processes of the present invention is envisaged. The primary and/or principal reaction zones may be operated with differing flow types of reaction mixture.

The primary and/or principal reaction zones employed in step 3-a) of the process of the present invention may be located within a single or multiple reactors. Thus, for example, in embodiments of the invention, all of the primary reaction zones could be different reaction zones in a single reactor, for example, a column liquid-gas reactor.

Alternatively, the primary reaction zones could be in different reactors (e.g. a series of continuously stirred tank reactors) or even different types of reactors (e.g. one or more primary reaction zones could be in a continuously stirred tank reactor and additional primary reaction zone/s could be in a tube reactor).

The reaction zones employed in step 3-a) of the process of the present invention may be operated at differing pressures and/or temperatures and/or have differing flows (e.g. flows of differing intensity/direction) of reaction mixture therein.

The reaction zones employed in step 3-a) of the process of the present invention may be operated in sequence (e.g. where reaction mixture is passed from an initial upstream reaction zone to a terminal downstream reaction zone, optionally via intermediate reaction zones) and/or in parallel.

In embodiments where the reaction zones are operated in step 3-a) in sequence and at differing temperatures and/or pressures, the temperature and/or pressure in some or all of the reaction zones may increase or decrease successively.

One, some or all of the reaction zones employed in step 3-a) of the process of the present invention may be operated at subatmospheric, atmospheric or superatmospheric pressure.

It has unexpectedly been found that the formation of chlorinated alkane degradation products can be minimised if the apparatus employed to operate step 3) of the process of the present invention (or at least those parts of it which come into contact with the reaction mixture and/or product streams) does not comprise certain materials.

Thus, in step 3) of the process of the present invention, the apparatus for conducting the step is configured such that those parts of the apparatus which come into contact with 1,1,1,2,3-pentachloropropane and/or 1,1,3-trichloropropene, in use of the apparatus, comprise less than about 20%, about 10%, about 5%, about 2% or about 1% of iron.

In such embodiments of step 3) of the process of the present invention, the apparatus for conducting the process is configured such that those parts of the apparatus which come into contact with 1,1,1,2,3-pentachloropropane and/or 1,1,3-trichloropropene are produced from fluoropolymers, fluorochloropolymers, glass, enamel, phenolic resin impregnated graphite, silicium carbide and/or fluoropolymer impregnated graphite. The combination of glass, PVDF, ETFE and Hastelloy, may be used for achieving a combination of effects, for example to provide the necessary conditions for visible or ultraviolet light to be provided to the reaction mixture while also ensuring that other problems such as corrosion and temperature are controlled.

In step 3-a) of the process of the invention, the principal reaction zone is in a plug/flow reactor. An advantage of the use of such apparatus is that the reactor can be configured to minimise or prevent back flow mixing.

The process steps outlined above minimise the formation of impurities, especially those impurities which are difficult to remove from 1,1,1,2,3-pentachloropropane.

To maximise the purity of the reaction mixture extracted from the primary reaction zone or the 1,1,1,2,3-pentachloropropane rich product obtained from the principal reaction zone, additional purification steps may be carried out in step 3-b) of the process of the present invention. For example, one or more distillation steps may be conducted. Such distillation steps may be conducted under low temperature/reduced pressure conditions.

Additionally or alternatively, one or more hydrolysis steps may be performed in step 3-b) of the process of the present invention. In embodiments in which the reaction mixture/ 1,1,1,2,3-pentachloropropane rich product (either typically being a mixture comprising 1,1,3-trichloropropene, 1,1,1,2, 3-pentachloropropane and impurities including oxygenated organic compounds) is subjected to a hydrolysis step, this typically involves contacting the reaction mixture extracted from the primary reaction zone/1,1,1,2,3-pentachloropropane rich product with an aqueous medium in a hydrolysis zone. Examples of aqueous media which may be employed in the hydrolysis step include water, steam and aqueous acid.

Hydrolysis is conducted at appropriate conditions to allow hydrolysis reaction(s), if any, to proceed.

Performance of a hydrolysis step in step 3-b) is preferable as this reduces the content of oxygenated organic compounds present in the reaction mixture/1,1,1,2,3-pentachloropropane rich product. Examples of oxygenated organic compounds include chlorinated alkanols, chlorinated acid chlorides, chlorinated acids, or chlorinated ketones.

In embodiments of the invention in which a hydrolysis step is performed, the reaction mixture/1,1,1,2,3-pentachloropropane rich product subjected to such a step may have an oxygenated organic compound content of about 500 ppm or less, about 200 ppm or less, about 100 ppm or less, about 50 ppm or less, or about 10 ppm or less, Thus, in embodiments of the invention, step 3-b) comprises removing oxygenated organic compounds from a mixture (obtainable from any upstream process) comprising 1,1,1,2,3-pentachloropropane, 1,1,3-trichloropropene and oxygenated organic compounds, comprising feeding the 1,1,1,2,3-pentachloropropane rich product into an aqueous treatment zone, contacting the 1,1,1,2,3-pentachloropropane rich product with an aqueous medium to produce a mixture and extracting i) an organic phase from that mixture or ii) a 1,1,1,2,3-pentachloropropane stream from that mixture, the organic phase/1,1,1,2,3-pentachloropropane stream comprising reduced levels of oxygenated organic compounds as compared to the 1,1,1,2,3-pentachloropropane rich product fed into the aqueous treatment zone.

In processes of the present invention in which a hydrolysis step is performed in step 3-b), the reaction mixture/1,1,1,2,3-pentachloropropane rich product fed into the aqueous treatment zone may have a low chlorine content, for example about 0.8% or less, about 0.5% or less, about 0.1% or less, about 0.05% or less or about 0.01% or less. For the avoidance of doubt, where reference is made in this context to chlorine, this encompasses free chlorine, unreacted chlorine, and dissolved chlorine. Chlorine which is bonded to atoms other than chlorine should not be considered.

In embodiments of the invention, the hydrolysis zone is in a washing tank. In such embodiments, the reaction mixture/1,1,1,2,3-pentachloropropane rich product may be washed with water and/or steam In step 3-b), once the reaction mixture/1,1,1,2,3-pentachloropropane rich product has been contacted with the aqueous medium to form a mixture in the hydrolysis zone, that mixture may be subjected to one or more treatment steps. For example, components of reaction mixture/1,1,1,2,3-pentachloropropane rich product (e.g. 1,1,1,2,3-pentachloropropane and/or unreacted 1,1,3-trichloropropene) can be extracted from the mixture formed in the aqueous treatment zone, for example via distillation preferably under reduced pressure and/or low temperature. Such a step can be achieved while the mixture is present in the aqueous treatment zone. Additionally or alternatively, the mixture may firstly be extracted from the aqueous treatment zone and subjected to the extraction step remotely from that zone.

Additionally or alternatively, in embodiments of the invention, a biphasic mixture may be formed in the aqueous treatment zone in step 3-b). In such embodiments, a phase separation step may be performed in which the organic phase comprising at least 1,1,1,2,3-pentachloropropane from the reaction mixture/1,1,1,2,3-pentachloropropane rich product is separated from the aqueous waste phase. This may be achieved by the sequential extraction of the phases from the aqueous treatment zone. Alternatively, the biphasic mixture could be extracted from the aqueous treatment zone and subjected to a phase separation step remote from the aqueous treatment zone to extract the organic phase.

The organic phase may, after optional filtering, be subjected to distillation to obtain streams comprising purified 1,1,1,2,3-pentachloropropane and/or 1,1,3-trichloropropene. 1,1,3-trichloropropene may be recycled to the primary and/or principal reaction zone/s. The purified 1,1,1,2,3-pentachloropropane may be the highly pure 1,1,1,2,3-pentachloropropane product.

Additionally or alternatively, the organic phase can be subjected to additional hydrolysis steps as outlined above in step 3-b) of the process of the present invention. The hydrolysis steps can be repeated if required, for example, one, two, three or more times.

In embodiments of the invention, mixtures comprising 1,1,1,2,3-pentachloropropane (e.g. the reaction mixture obtained from the primary reaction zone, the 1,1,1,2,3-pentachloropropane rich product obtained from the principal reaction zone, the mixture formed in the aqueous treatment zone and/or the organic phase extracted from the biphasic mixture) can be subjected to a distillation step in step 3-b), preferably conducted at a temperature of about 100° C. or lower, about 90° C. or lower or about 80° C. or lower.

Such a distillation step may be conducted under vacuum. Where vacuum distillation is carried out, the vacuum conditions may be selected such that the distillation may be conducted at a low temperature and/or to facilitate the extraction of higher molecular weight chlorinated alkanes.

In embodiments of the invention, in step 3-b), any distillation steps conducted in the process of the present invention may result in streams comprising at least about 50%, at least about 80%, at least about 90%, at least about 95%, at least about 97%, at least about 98%, at least about 99%, at least about 99.5%, at least about 99.7%, at least about 99.8%, or at least about 99.9% of i) 1,1,3-trichloropropene and/or ii) 1,1,1,2,3-pentachloropropane. As used herein, the term 'streams' should be construed broadly to encompass a composition obtained from any distillation step, regardless of the apparatus used or the form of the composition obtained. Streams of highly pure 1,1,1,2,3-pentachloropropane may be the highly pure 1,1,1,2,3-pentachloropropane product of step 3-b).

Any distillation equipment known to those skilled in the art can be employed in step 3-b) of the process of the present invention, for example a distillation boiler/column arrangement. However, it has unexpectedly been found that the formation of chlorinated alkane degradation products can be minimised if distillation apparatus formed of certain materials are avoided.

Thus, in embodiments of the invention, step 3-b) comprises the step of distilling a 1,1,1,2,3-pentachloropropane rich product (regardless of the process from which it was obtained), in which distillation apparatus is employed, the distillation apparatus being free of components which, in use of the distillation apparatus, would come into contact with the process fluids (including the liquid or distillate) and comprise about 20% or more, about 10% or more, about 5% or more, about 2% or more or about 1% or more of iron.

In embodiments of the invention in which distillation step/s are carried out in step 3-b), the distillation apparatus may be configured such that all of its components which, in use of the distillation apparatus, would come into contact with the distillate or process fluid, are produced from fluoropolymers, fluorochloropolymers, glass, enamel, phenolic resin impregnated graphite, silicium carbide and/or fluoropolymer impregnated graphite.

Where distillation steps are performed as part of step 3-b) of the process of the present invention, streams obtained in such steps which comprise 1,1,3-trichloropropene may be recycled and fed into the primary and/or principal reaction zone/s.

The processes of the present invention are particularly advantageous as they enable highly pure 1,1,1,2,3-pentachloropropane to be produced using simple and straightforward techniques and equipment with which one skilled in the art would be familiar.

In embodiments of the invention, the process of step 3) of the present invention can be used to produce high purity 1,1,1,2,3-pentachloropropane which comprises:

1,1,1,2,3-pentachloropropane in amounts of at least about 95%, at least about 99.5%, at least about 99.7%, at least about 99.8%, at least about 99.9%, or at least about 99.95%, and one or more of the following:
- oxygenated organic compounds in amounts of less than about 500 ppm, about 250 ppm or less, about 100 ppm or less, about 50 ppm or less, or about 1 Oppm or less,
- isomers of 1,1,1,2,3-pentachloropropane in amounts of less than about 500 ppm or less, about 250 ppm or less, or about 100 ppm or less,
- non-isomeric alkane impurities in amounts of less than about 500 ppm, about 250 ppm or less, or about 100 ppm or less,
- chlorinated alkenes in amounts of less than about 500 ppm, about 250 ppm or less, about 100 ppm or less, or about 50 ppm or less,
- water in amounts of less than about 500 ppm, about 250 ppm or less, about 100 ppm or less, or about 50 ppm or less,
- inorganic compounds of chlorine in amounts of about 100 ppm or less, about 50 ppm or less, about 20 ppm or less, or about 10 ppm or less,
- brominated organic compounds in amounts of about 100 ppm or less, about 50 ppm or less, about 20 ppm or less, or about 10 ppm or less, and/or
- iron, in amounts of less than about 500 ppm, less than about 200 ppm, less than about 100 ppm, less than about 50 ppm, less than about 20 ppm, less than about 10 ppm or less than about 5 ppm.

For the avoidance of doubt, the term 'inorganic compounds of chlorine' encompasses non-organic compounds containing chlorine, including chlorine ($Cl_2$), hydrogen chloride and phosgene.

In embodiments of the present invention, the composition may comprise less than about 1000 ppm, less than about 500 ppm, less than about 200 ppm, or less than about 100 ppm of organic compounds other than 1,1,1,2,3-pentachloropropane. Additionally or alternatively, the composition may collectively comprise less than about 0.5%, less than about 0.3%, less than about 0.1% of organic compounds other than 1,1,1,2,3-pentachloropropane.

As can be seen from the disclosure provided herein, the inventive processes of steps 1), 2) and 3) of the present invention can be operated in an integrated process in a fully continuous mode, optionally in combination with other processes. The process steps of the present invention may employ starting compounds which are converted to highly pure intermediates which are themselves further processed to the required target chlorinated compounds. Those compounds have the requisite purity to be employed as feedstocks in a range of downstream processes, for example to produce other (high purity) chlorinated alkenes (eg tetrachloropropene), or for hydrofluorination conversions.

The prior art fails to disclose or teach processes for producing chlorinated alkanes having such a high degree of purity and in high yield, with selective reaction. Thus, according to further aspects of the present invention, there are provided high purity 1,1,1,2,3-pentachloropropane compositions as set out above.

Additionally, compositions having the impurity profiles corresponding to the products of step 3) of the process of the present invention are especially well suited to use as starting materials in the synthesis of fluoroalkanes or fluoroalkenes and/or chlorofluorinated alkenes. Thus, according to a further aspect of the present invention, there is provided the use of the high purity 1,1,1,2,3-pentachloropropane compositions outlined herein as feedstocks in the synthesis of the above-identified fluoroalkanes/fluoroalkenes and/or chlorofluoroalkenes. In one embodiment of this aspect of the present invention, the compositions may be used to produce 2,3,3,3-tetrafluoropropene (HFO-1234yf). In another embodiment of this aspect of the present invention, the compositions may be used to produce 2-chloro-3,3,3-trifluoropropene (HFO-1233xf).

Main advantages of preferred embodiments of the process of the present invention can be listed as:
- degree of control of the reaction processes, so that single high grade intermediates and final product are obtained with global impurities which are kept very low;
- all process reaction steps are extremely isomeric selective resulting in high starting material utilization and very pure both intermediates and final product;
- treatment processes to further refine the quality of the intermediates and final product, especially regarding problematical oxygenated compounds;
- the produced intermediates and final product are advantageously of high quality not requiring special stabilisation for storage or transportation;
- the processes are operable continuously, in an industrial setting;
- the overall yields of the high grade desired intermediates and product are high.

| | |
|---|---|
| 1 | ethene feed stream |
| 2 | particulate iron feed stream |
| 3 | continuously stirred tank reactor (primary alkylation zone) |
| 4 | plug/flow reactor (principal alkylation zone) |
| 5 | reaction mixture stream |
| 6 | flash evaporation vessel |
| 7 | 1,1,1,3-tetrachloropropane-rich mixture stream |
| 8 | evaporated ethene stream |
| 9 | condenser |
| 10 | ethene stream |
| 11 | absorption column |
| 12 | carbon tetrachloride and tributyl phosphate/ferric chloride catalyst feed stream |
| 13 | stream of recovered catalyst (tributyl phosphate/ferric chloride), fresh catalyst and carbon tetrachloride |
| 14 | cooler |
| 15 | cooled stream of recovered catalyst (tributyl phosphate/ferric chloride), fresh catalyst and carbon tetrachloride |
| 16 | off-gas |

Figure 2:
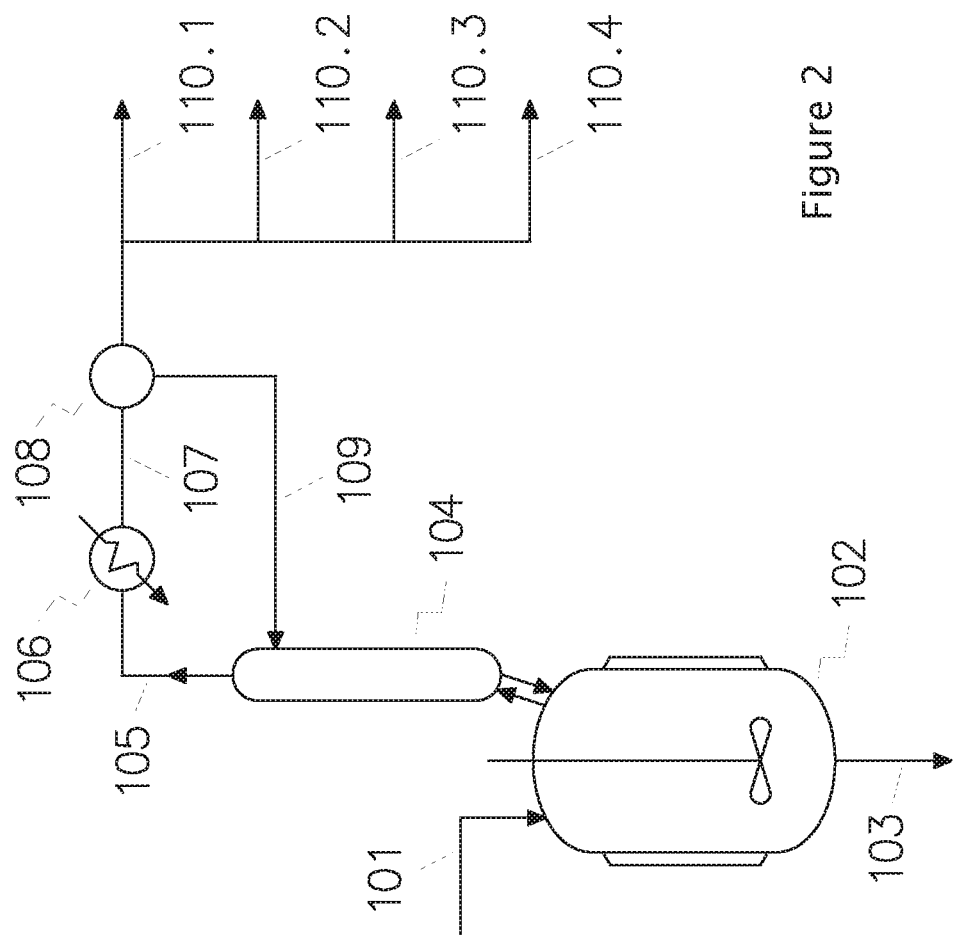

FIG. 2—First Distillation Step

| | |
|---|---|
| 101 | 1,1,1,3-tetrachloropropane-rich mixture stream (stream with reference numeral 7 in FIG. 1) |
| 102 | batch distillation boiler |
| 103 | stream of 1,1,1,3-tetrachloropropane-rich mixture comprising catalyst |
| 104 | vacuum distillation column |
| 105 | distillate stream |
| 106 | condenser |
| 107 | intermediate line |
| 108 | reflux divider |
| 109 | reflux stream |
| 110.1 | light ends stream |
| 110.2 | carbon tetrachloride stream |
| 110.3 | tetrachloroethene stream |
| 110.4 | purified 1,1,1,3-tetrachloropropane product stream |

Figure 3:
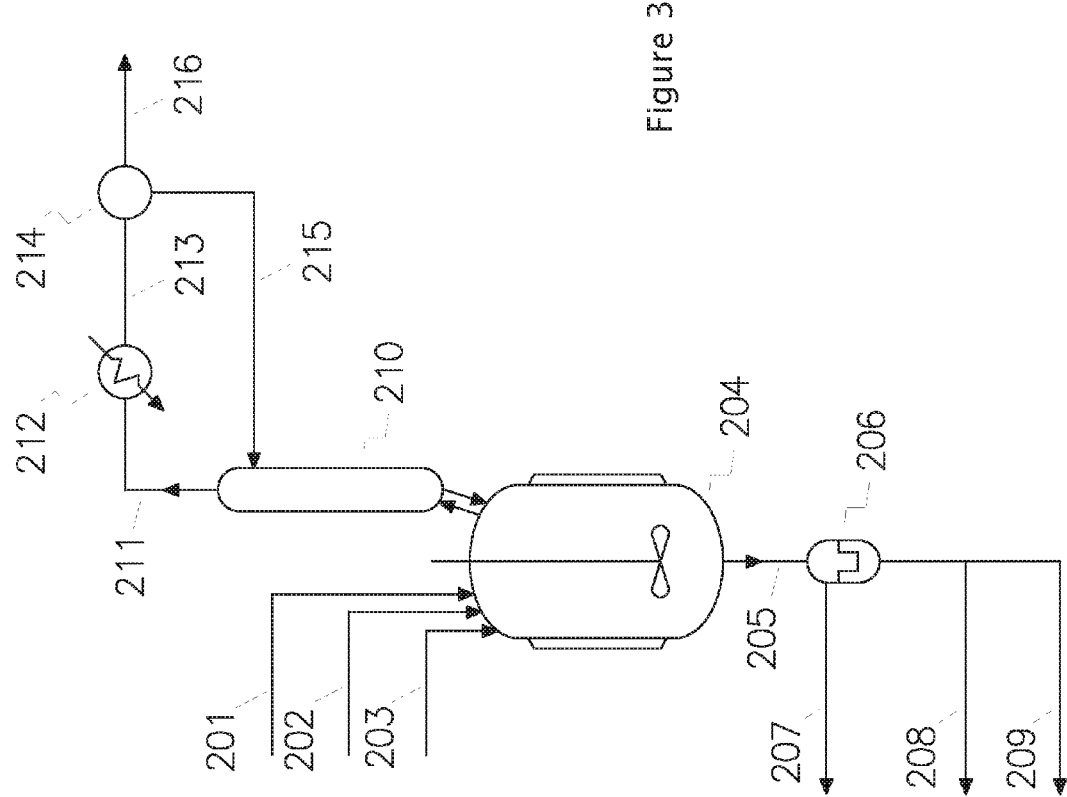

FIG. 3—Aqueous Catalyst Recovery Step

| | |
|---|---|
| 201 | weak hydrochloric acid solution stream |
| 202 | 1,1,1,3-tetrachloropropane-rich mixture feed stream comprising catalyst |

| 203 | haloalkane extraction agent feed stream (1,1,1,3-tetrachloropropane) |
| 204 | batch distillation boiler |
| 205 | batch distillation boiler outlet |
| 206 | filtration |
| 207 | filter cake removal |
| 208 | organic phase stream (part of feed stream 13 in FIG. 1) |
| 209 | aqueous phase stream |
| 210 | column for steam distillation of crude 1,1,1,3-tetrachloropropane |
| 211 | crude 1,1,1,3-tetrachloropropane stream |
| 212 | condenser |
| 213 | condensed crude 1,1,1,3-tetrachloropropane stream |
| 214 | reflux liquid-liquid separator |
| 215 | reflux stream |
| 216 | crude 1,1,1,3-tetrachloropropane stream for further distillation |

Figure 4:
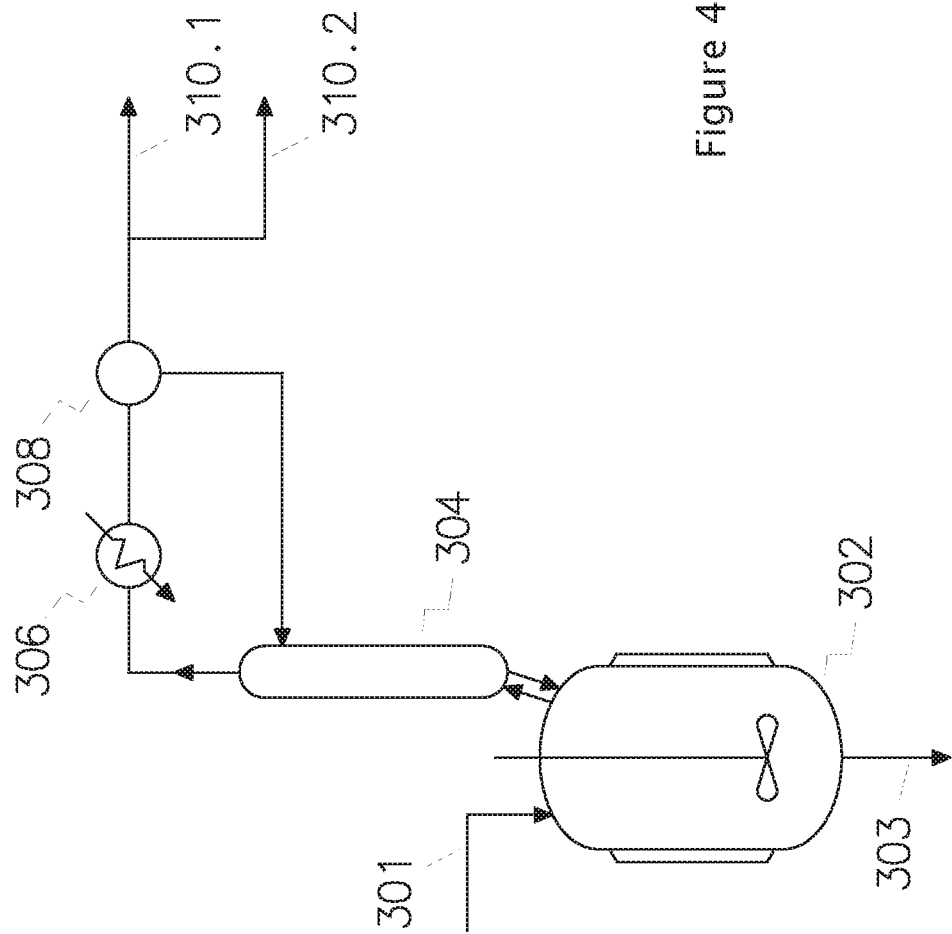

FIG. 4—Second Distillation Step

| 301 | crude 1,1,1,3-tetrachloropropane product feed stream |
| 302 | distillation boiler |
| 303 | heavy ends residue |
| 304 | distillation column |
| 306 | condenser |
| 308 | reflux divider |
| 310.1 | purified 1,1,1,3-tetrachloropropane product stream |
| 310.2 | chlorinated pentane/pentene stream |

Figure 5:
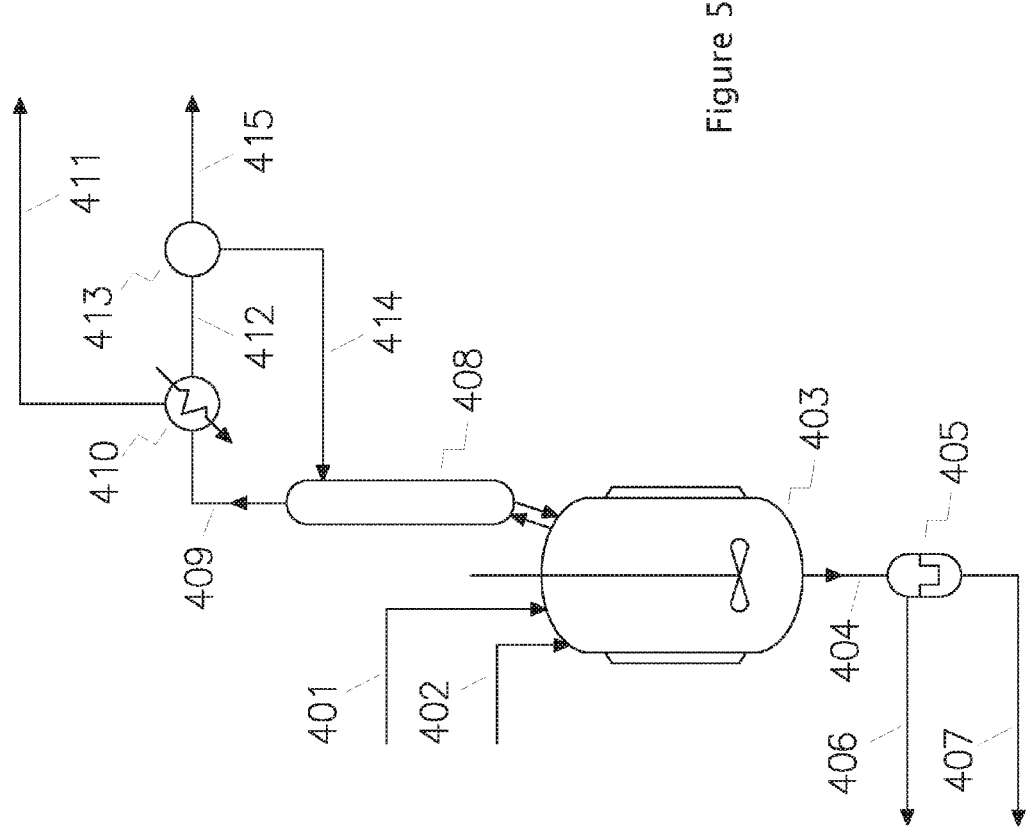

FIG. 5—Dehydrochlorination Step (1,1,1,3-tetrachloropropane Conversion to 1,1,3-trichloropropene)

| 401 | 1,1,1,3-tetrachloropropane feed stream |
| 402 | ferric chloride feed stream |
| 403 | continuously stirred tank reactor |
| 404 | reaction residue |
| 405 | filter |
| 406 | filter cake |
| 407 | filtrate |
| 408 | distillation column |
| 409 | 1,1,3-trichloropropene rich stream |
| 410 | partial condenser |
| 411 | gaseous hydrogen chloride stream |
| 412 | 1,1,3-trichloropropene rich stream |
| 413 | reflux divider |
| 414 | reflux stream |
| 415 | purified 1,1,3-trichloropropene product stream |

Figure 6:
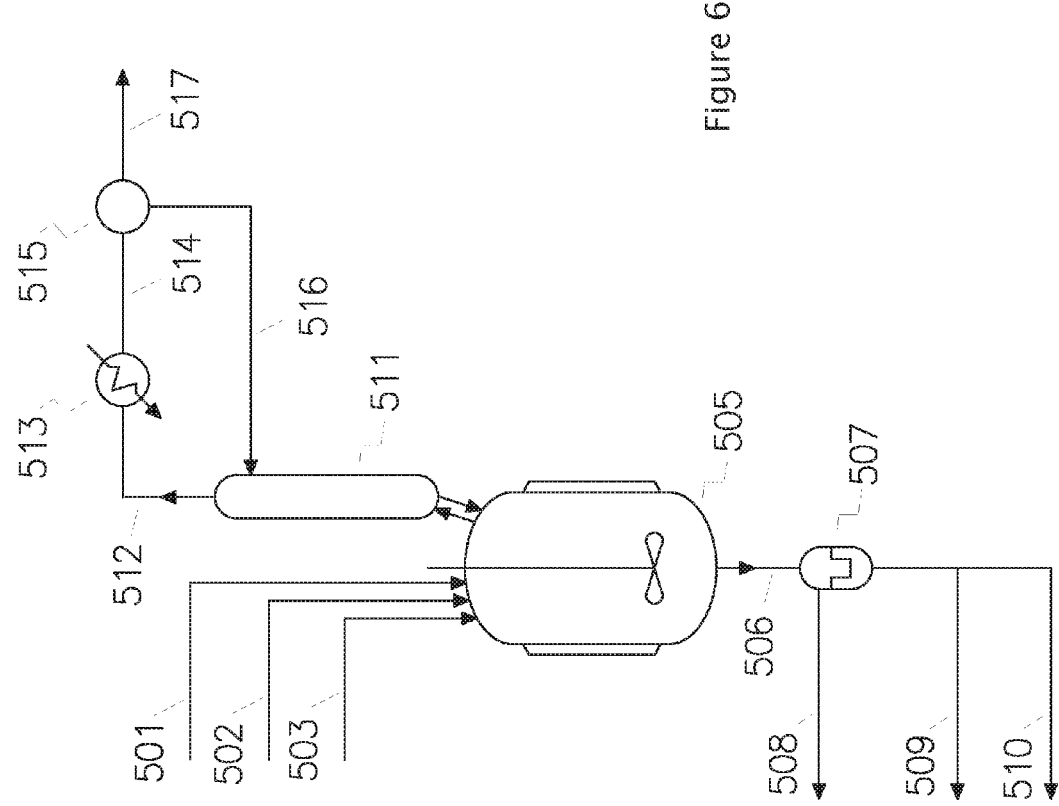

FIG. 6—Aqueous Treatment Step

| 501 | aqueous hydrochloric acid feed stream |
| 502 | residue feed stream (from the reactor in FIG. 1, stream 4) |
| 503 | haloalkane extraction agent feed stream |
| 504 | |
| 505 | washing tank |
| 506 | washing tank outlet |
| 507 | filter |
| 508 | filter cake |
| 509 | organic phase stream |
| 510 | aqueous phase stream |
| 511 | distillation column |
| 512 | chlorinated alkanes stream |
| 513 | condenser |
| 514 | intermediate line |
| 515 | reflux liquid-liquid separator |
| 516 | aqueous phase (reflux) stream |
| 517 | organic phase (1,1,1,3-tetrachloropropane) stream |

Figure 7:
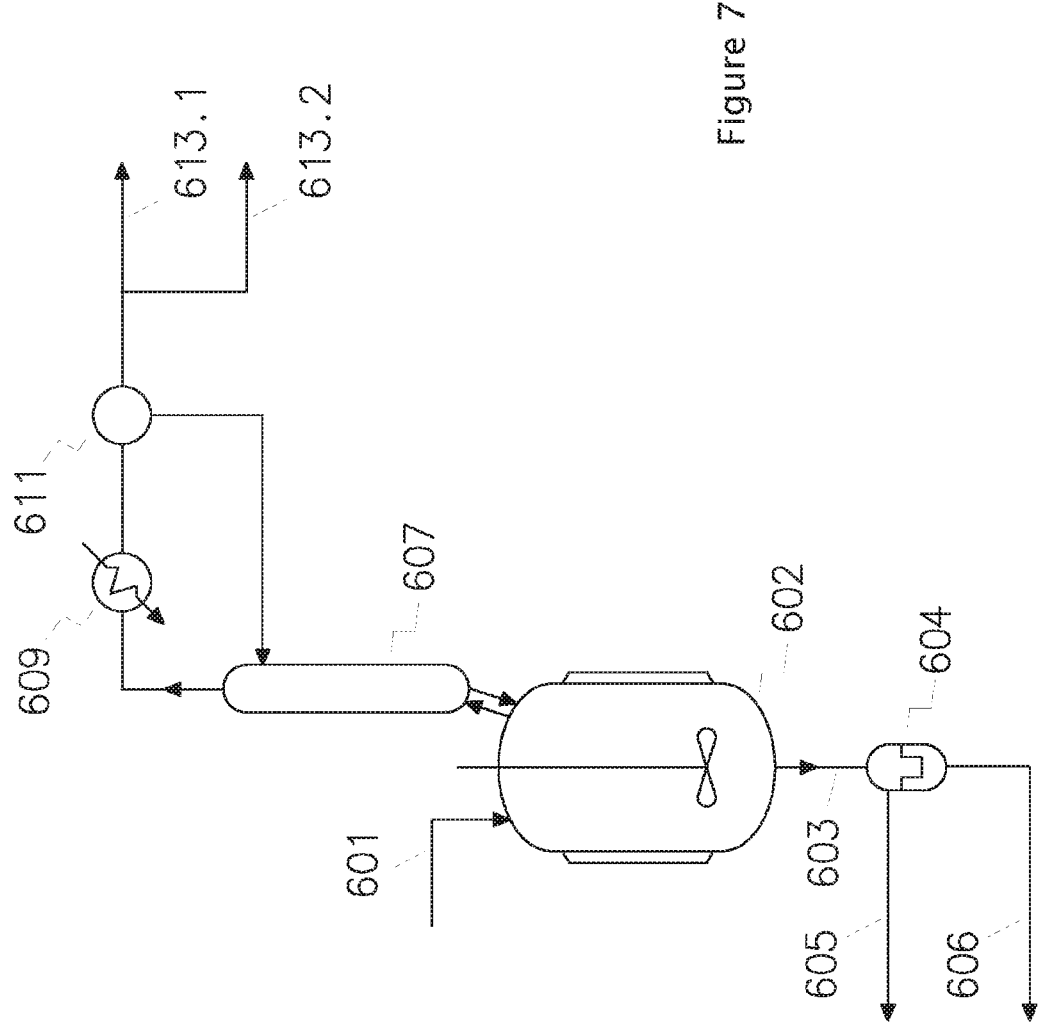

FIG. 7—Distillation Step

| 601 | organic phase (1,1,1,3-tetrachloropropane) feed stream |
| 602 | distillation boiler |
| 603 | heavy ends residue stream |
| 604 | filter |
| 605 | filter cake |
| 606 | liquid residue |
| 607 | distillation column |
| 609 | condenser |
| 611 | reflux divider |
| 613.1 | 1,1,3-trichloropropene product stream |
| 613.2 | 1,1,1,3-tetrachloropropane stream |

Figure 8:
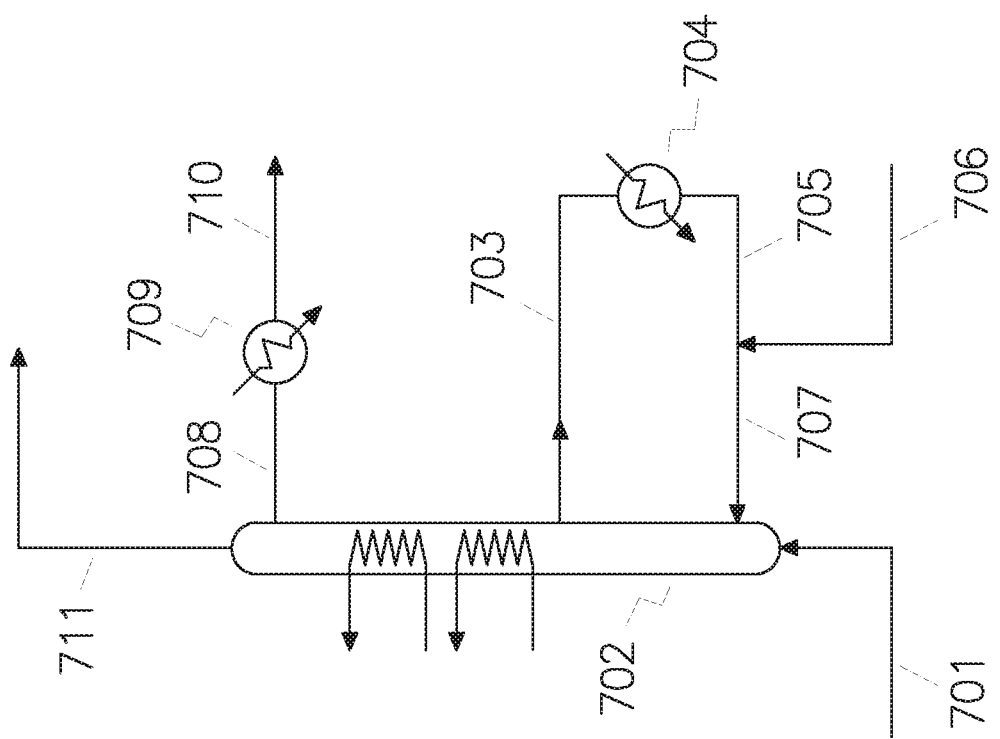

FIG. 8—Primary Conversion and Principal Conversion Steps (1,1,3-trichloropropene Conversion to 1,1,1,2,3-pentachloropropane)

| 701 | gaseous chlorine feed stream |
| 702 | gas-liquid reactor column |
| 703 | external circulation loop |
| 704 | external cooler |
| 705 | external circulation loop |
| 706 | 1,1,3-trichloropropene feed stream |
| 707 | external circulation loop |
| 708 | 1,1,1,2,3-pentachloropropane-rich stream |
| 709 | cooler |
| 710 | 1,1,1,2,3-pentachloropropane-rich stream (feed to hydrolysis step, FIG. 2) |
| 711 | off-gas |

Figure 9:
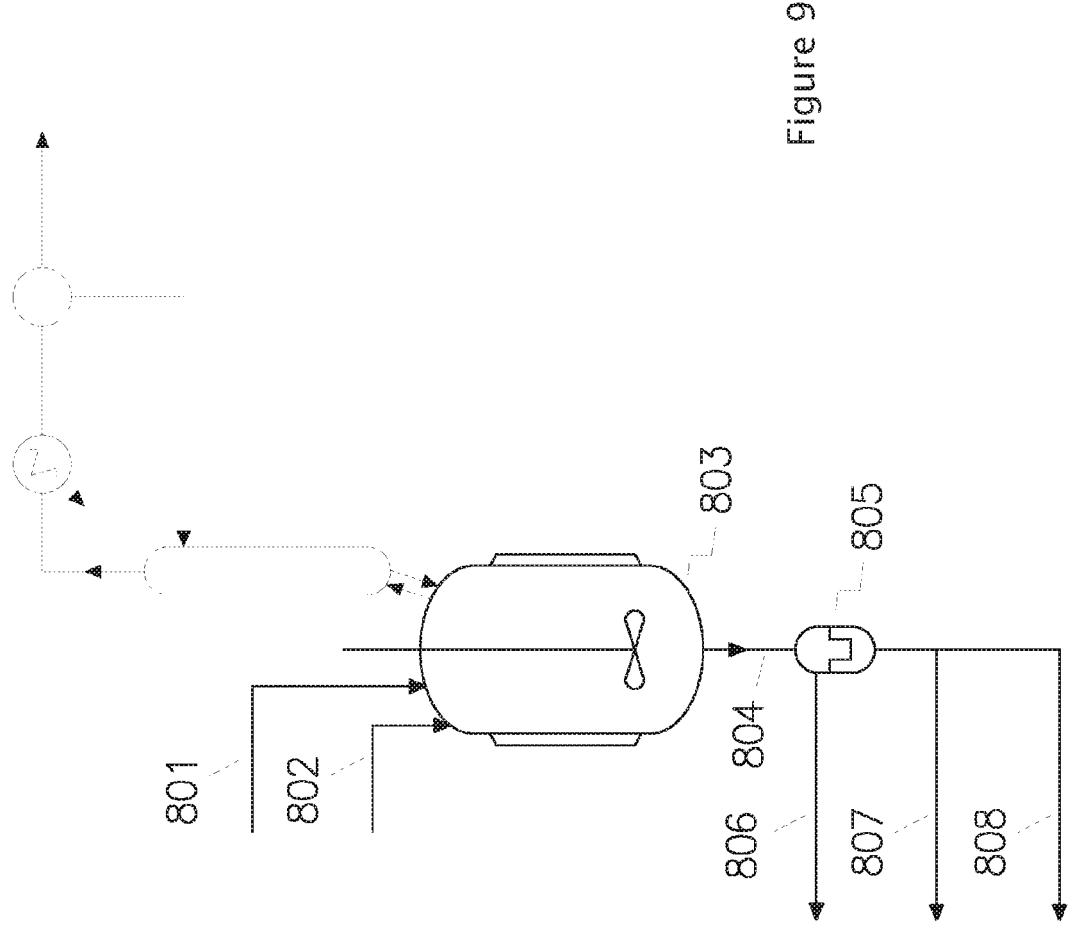

FIG. 9—Hydrolysis Step

| 801 | water stream |
| 802 | 1,1,1,2,3-pentachloropropane-rich feed stream |
| 803 | washing tank |
| 804 | washing tank outlet |
| 805 | filter |
| 806 | filter cake |
| 807 | 1,1,1,2,3-pentachloropropane-rich product stream |
| 808 | wastewater stream |

Figure 10:
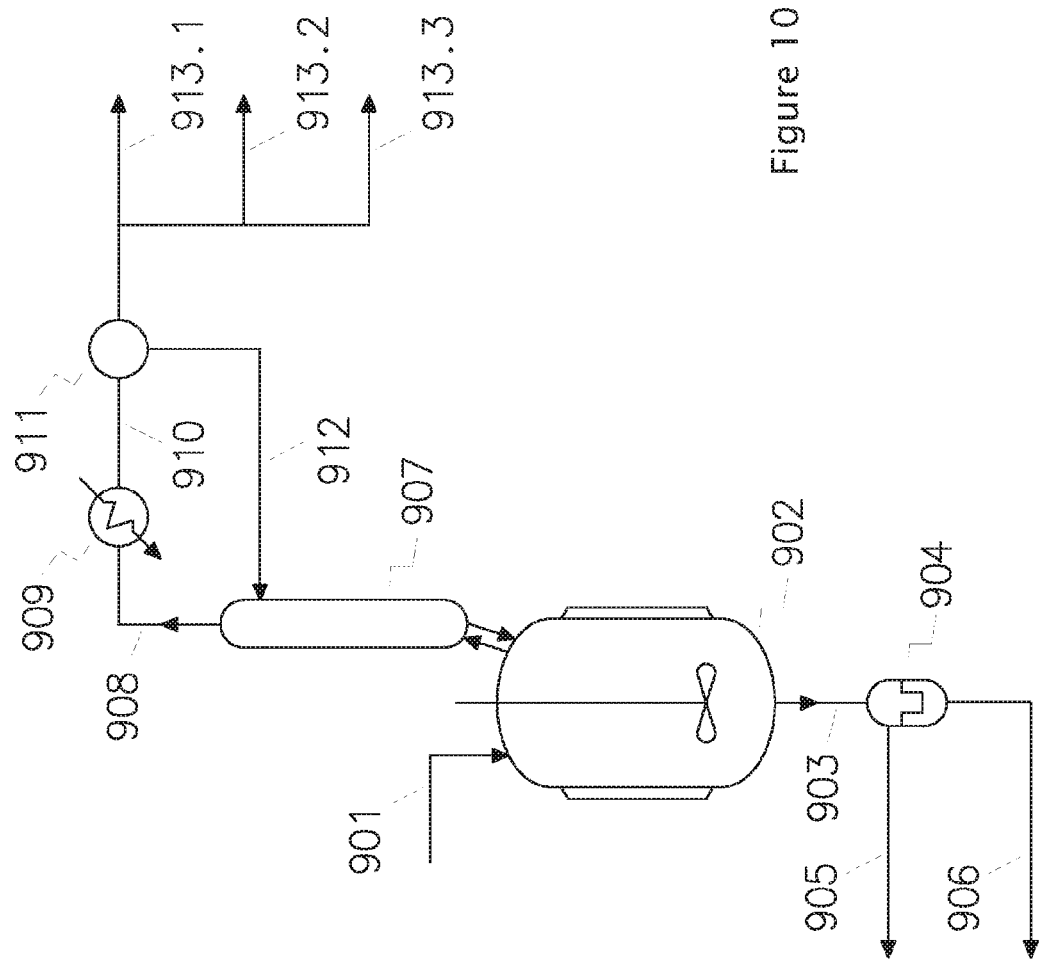

FIG. 10—Distillation Step

| 901 | 1,1,1,2,3-pentachloropropane-rich feed stream (product stream 107, FIG. 2) |
| 902 | distillation boiler |
| 903 | distillation residue stream |
| 904 | filter |
| 905 | filter cake |
| 906 | heavies stream |
| 907 | vacuum distillation column |
| 908 | distillate stream |
| 909 | condenser |
| 910 | intermediate line |
| 911 | liquid divider |
| 912 | reflux stream |
| 913.1 | 1,1,3-trichloropropene stream |
| 913.2 | 1,1,1,3-tetrachloropropane stream |
| 913.3 | purified 1,1,1,2,3-pentachloropropane stream |

EXAMPLES

The present invention is now further illustrated in the following examples. For the avoidance of doubt, where reference is made to units of pressure (kPa) herein it is the absolute value which is identified. Where values are presented as percentages herein, they are percentages by weight unless otherwise stated. Where the purity of a composition or material is presented by percentage or ppm herein, unless otherwise stated, this is a percentage/ppm by weight.

For clarity, Examples 1 to 7 exemplify or relate to the telomerisation reaction (and subsequent treatment steps) of step 1) of the process of the present invention. Examples 8 to 12 exemplify or relate to the dehydrochlorination reaction (and subsequent treatment steps) of step 2) of the process of the present invention. Examples 13 to 19 exemplify or relate to the chlorination reaction (and subsequent treatment steps) of step 3) of the process of the present invention.

Abbreviations used:
TeCPa=1,1,1,3-tetrachloropropane
TCPe=1,1,3-trichloropropene
PCPa=1,1,1,2,3-pentachloropropane
TeCM: tetrachloromethane
TeCPna: tetrachloropentane
HCE=hexachloroethane
DCPC=dichloropropanoylchloride
$Bu_3PO_4$: Tributylphosphate Example 1

Demonstration of Catalytic Ability of Recovered Catalyst Using an Aqueous Treatment Ethylene and carbon tetrachloride were reacted to produce 1,1,1,3-Tetrachloropropane in the presence of catalyst which was either i) recovered from a reaction mixture using conventional distillation techniques, or ii) recovered from a reaction mixture using the inventive aqueous treatment step for catalyst described herein. The reaction mixture additionally comprised 1,1,1,3-Tetrachloropropane (present in the recycle stream) and tetrachloropentane (a chlorinated alkane impurity commonly formed as a byproduct in the presence of telomerisation reactions between carbon tetrachloride and ethylene).

These test examples show that using the aqueous treatment step to recover catalyst, the performance of the catalyst is significantly higher as compared to catalyst recovered using conventional distillation techniques.

Gas chromatography was used to monitor the progress of the reaction.

Batchwise Arrangement

A stainless steel autoclave with a volume of 405 ml, equipped with a stirrer, a thermowell for temperature measurement and a sampling tube (with valve) was filled with the reaction mixture described below and closed. Heating was provided by means of an oil bath placed on a magnetic (heating) stirrer. Ethylene was fed by a copper capillary tube from 10 l cylinder placed on weighing scale. The gaseous atmosphere in the autoclave was replaced by ethylene flushing. After pressurizing with ethylene to 5 bar, the autoclave was heated up to 105° C., then the ethylene supply to the autoclave was opened. Ethylene supply was controlled manually for a first ten minutes (to maintain the reaction temperature to 112° C.), and later was maintained at a constant pressure of 9 bar. The reaction was allowed to react defined time period. Than the reactor was cooled and reaction mixture was withdrawn after opening of depressurised reactor.

Comparative Examples 1-1 and 1-3 and Examples 1-2, 1-4 and 1-5

In the first example, the distillation residue was directly used as a recycled catalyst (Comparative Example 1-1). In the second example, the distillation residue was extracted with 5% hydrochloric acid and a filtered organic fraction was used as a catalyst (Example 1-2).

Comparative Example 1-1

90.1 g of a distillation residue comprising 63.7% TeCPa, 22.8% TeCPna and 7.49% $Bu_3PO_4$ was mixed with 400 g of TeCM. The mixture was then introduced into the autoclave where 5.0 g of iron was added. After flushing with ethylene, the mixture was heated in the autoclave up to 110° C. At this temperature and at a pressure of 9 bar of ethylene, the reaction mixture was allowed to react for 4.5 hours. The first sample was taken after 3 hours. The concentration of residual TeCM at the end of the experiment was 19.7% (33.0% after 3 hours).

Example 1-2

90.1 g of a distillation residue comprising 63.7% TeCPa, 22.8% TeCPna and 7.49% $Bu_3PO_4$ was extracted with 370 g of 5% HCl. A bottom organic layer was filtered and mixed with 400 g TeCM. The mixture was then introduced into the autoclave where 5.0 g of iron was added. After flushing with ethylene, the mixture was heated in the autoclave up to 110° C. At this temperature and at a pressure of 9 bar of ethylene, the reaction mixture was allowed to react for 4.5 hours. The first sample was taken after 3 hours. The concentration of residual TeCM at the end of the experiment was 5.5% (24.6% after 3 hours).

Comparative Example 1-3

Comparative Example 1-3 was carried out using identical conditions as those employed in Comparative Example 1-1, except that differing concentrations of tetrachloromethane and tributylphosphate were used.

Example 1-4 and 1-5

Examples 1-4 and 1-5 were carried out using identical conditions as those employed in Example 1-2, except that differing concentrations of tetrachloromethane and tributylphosphate were used.

The results of Comparative Example 1-1 and Example 1-2, and Comparative Example 1-3 and Examples 1-4 and 1-5 are shown in the following table. As can be seen, the percentage of tetrachloromethane which was converted to 1,1,1,3-Tetrachloropropane is significantly higher in Examples 1-2, 1-4 and 1-5 than in Comparative Examples 1-1 and 1-3 demonstrating that the performance of an aqueous treatment step when recovering the catalyst has a profound positive effect on the system. This is due to the high viability of the catalyst recovered from the distillate residue and also potentially due to the removal of impurities (e.g. oxygenated impurities) from the reaction mixture which otherwise may retard the reaction.

| Example | % TeCM in $Bu_3PO_4$ | the feedstock | % of reacted TeCM 3 hrs. | 4.5 hrs. |
| --- | --- | --- | --- | --- |
| Comparative Example 1-1 | 1.37% | 84.7% | 57.4% | 73.8% |
| Example 1-2 | 1.35% | 83.7% | 67.3% | 92.4% |
| Comparative Example 1-3 | 1.77% | 78.7% | 60.0% | 78.1% |
| Example 1-4 | 1.64% | 81.2% | 87.7% | 99.4% |
| Example 1-5 | 1.64% | 70.6% | 78.7% | 99.4% |

Continuous Arrangement:

The same stainless steel autoclave as described above for the batch experiments was used as a stirred flow continuous reactor. The reactor was initially filled with approximately 455 g of reaction mixture. After pressurizing with ethene to 5 bar, the autoclave was heated up to 105° C., then the ethylene supply to the autoclave was opened, with continuous feed of the raw material and continuous withdrawal of the reaction mixture started.

Feedstock solution with dissolved catalyst was fed into the autoclave from a stainless steel tank. The tank was placed above the reactor, and thus, a pump was not used for feeding the reactor. Reactor and tank were under an atmosphere of ethene distributed by copper capillaries from the cylinder, with conditions in the cylinder selected to prevent commencement of the reaction. Sampling of the reaction mixture was carried out by sampling tube every five minutes. To monitor the course of the reaction, the container with the feedstock and dissolved catalyst, cylinder of ethene and the withdrawn reaction mixture were weighed. The reaction mixture was always collected for an hour and after that, the collecting vessel is replaced.

Comparative Example 1-6 and 1-8 and Examples 1-7 and 1-9

Continuous experiments comparing the activity of recycled catalyst (i.e. a distillation residue were conducted with and without performance of an aqueous treatment step. In the first case, the distillation residue was directly used as a recycled catalyst (Comparative Example 1-6). In the latter cases, the reaction mixture, after aqueous treatment of the distillation residue with 5% HCl, was used as a raw material containing recycled catalyst (Examples 1-4 and 1-5).

Comparative Example 1-6

587.5 g of the distillation residue comprising 63.7% TeCPa, 22.8% TeCPna and 7.49% Bu3PO4 was mixed with 2200 g of TeCM. This mixture comprised 78.7% TeCM, 11.8% TeCPa, 5.8% TeCPna and was used as a feed stream for the continuous arrangement. The reaction vessel constituted an autoclave was filled with reaction mixture and 8 g of fresh iron. The reaction was carried out at 110° C. with a pressure of ethylene of 9 bar. The residence time was 2.7 hours. During the reaction, the amount of reacted TeCM ranged between 75-76%.

Example 1-7

587.5 g of the distillation residue comprising 63.7% TeCPa, 22.8% TeCPna 7.49% Bu3PO4 was added dropwise over 1.5 hour into 1001.5 g of boiling 5% HCl. This mixture was then stripped. From the overhead product, an organic phase was collected and an aqueous phase was returned as a reflux. Distillation was terminated after an hour when all of the distillation residue was added. The residue, after stripping, was diluted with 200 g of TeCM and then separated in a separatory funnel. A bottom organic phase was filtered and together with distilled residue was mixed with 2000 g of TeCM. This mixture comprised 81.2% TeCM, 10.8% TeCPa and 5.3% TeCPna. It was used as a feed stream for the continuous arrangement of the experiment. The reaction vessel (autoclave) was filled with the older reaction mixture and 8 g of fresh iron. The reaction was carried out at 110° C. and a pressure of ethene of 9 bar. Residence time was 2.7 hours/flow rate. During the time of the reaction the amount of reacted TeCM ranged between 83-85%.

Comparative Example 1-8

Comparative Example 1-8 was carried out using identical conditions as those employed in Comparative Example 1-6, except that differing concentrations of tetrachloromethane and tributylphosphate were used.

Example 1-9

Example 1-9 was carried out using identical conditions as those employed in Example 1-7, except that differing concentrations of tetrachloromethane and tributylphosphate were used.

| Example (recycled catalyst) | Bu$_3$PO$_4$ | % TeCM in the feedstock | % reacted TeCM |
| --- | --- | --- | --- |
| Comparative Example 1-6 | 1.67% | 78.7% | 75.0% |
| Example 1-7 | 1.64% | 81.2% | 84% |
| Comparative Example 1-8 | 1.83% | 76.8% | 60% |
| Example 1-9 | 1.89% | 78.0% | 89% |

Example 2

Preparation of High Purity 1,1,1,3-tetrachloropropane

High purity 1,1,1,3-Tetrachloropropane may be obtained according to step 1) of the process of the present invention involving an alkylation step (FIG. 1), a first distillation step (FIG. 2), an aqueous catalyst recovery step (FIG. 3) and a second distillation step (FIG. 4). However, it will be appreciated that not all of these steps are necessary to obtain high purity $C_{3-6}$ alkane according to step 1) of the process of the present invention.

Figure 1:
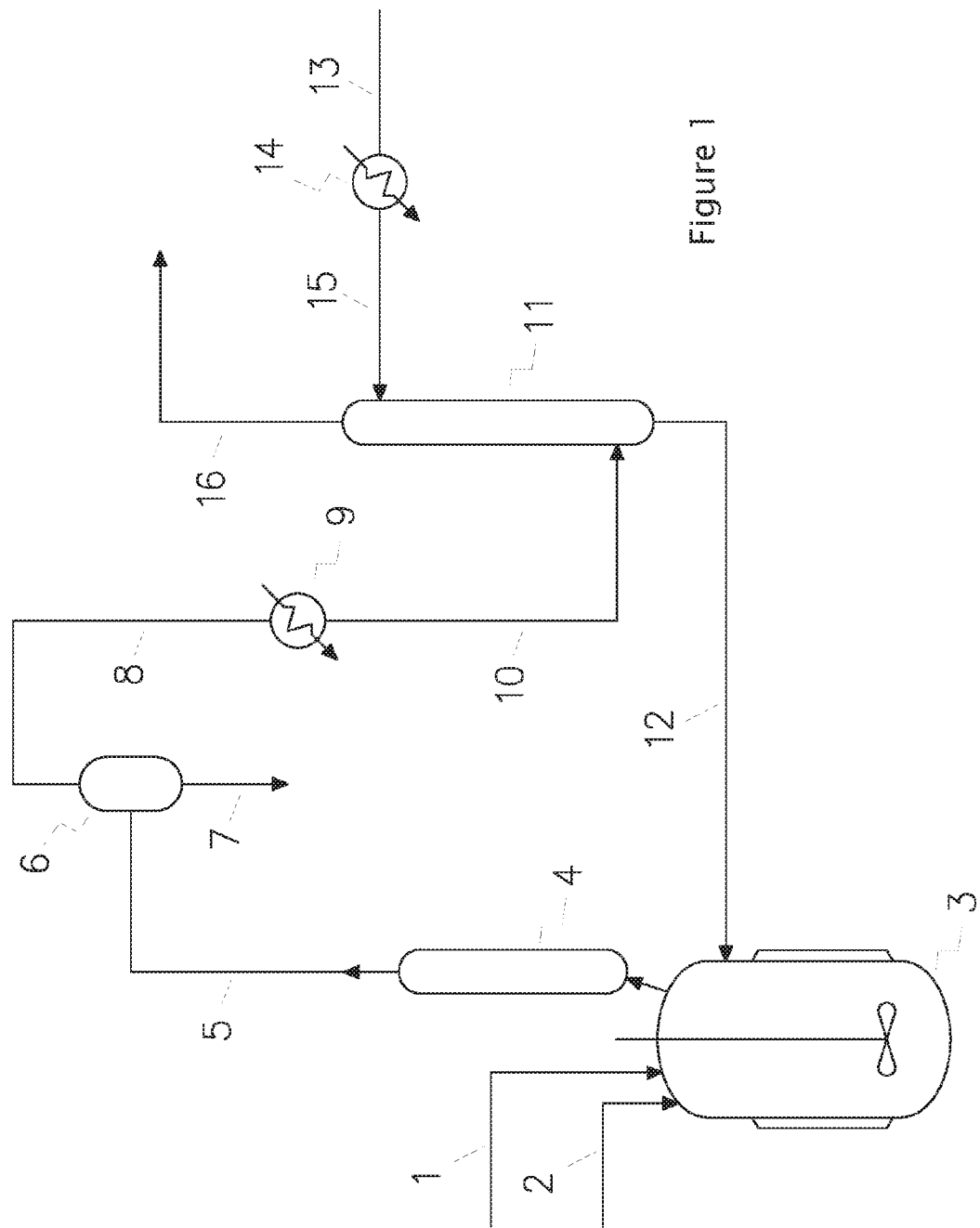
FIG. 1—Alkylation Step

In the alkylation step shown in FIG. 1, ethene and particulate iron are fed via lines 1 and 2 into a continuously stirred tank reactor 3. The ethene is introduced into the continuously stirred tank reactor 3 in gaseous form via a dip tube provided with a nozzle. A controlled feed of particulate iron is fed into the continuously stirred tank reactor 3.

Particulate iron is intermittently fed into the continuously stirred tank reactor 3 using a controlled feed. The ongoing addition of particulate iron is employed because, as the alkylation reaction proceeds, particulate iron dissolves into the reaction mixture. It has been found that optimal results are obtained by maintaining the presence of particulate iron in the reaction mixture, in this example with the addition of 1 to 2% by weight of the reaction mixture in the primary alkylation zone. This results in the reaction mixture extracted from the primary alkylation zone having a dissolved iron content of 0.2 to 0.3% by weight of the reaction mixture.

Carbon tetrachloride is fed into the continuously stirred tank reactor 3 via line 12 in liquid form. In the illustrated embodiment, the carbon tetrachloride stream is used to trap gaseous ethene extracted from the reaction mixture. However, the use of carbon tetrachloride in this way is not essential to the present invention; a feed of fresh carbon tetrachloride as the sole or main source of carbon tetrachloride could be fed into the reactor 3.

Tributyl phosphate/ferric chloride catalyst is also fed into the continuously stirred tank reactor 3 via line 12. The tributyl phosphate present in that stream is partly obtained from the aqueous treatment process illustrated in FIG. 3 (and discussed below in more detail), with the balance being provided as fresh tributyl phosphate added into the system. The stream in line 12 additionally comprises a haloalkane extraction agent.

In the illustrated embodiment, a single primary alkylation zone is employed, located in the continuously stirred tank reactor 3. Of course, if required, a plurality of primary alkylation zones could be employed, for example in one or more continuously stirred tank reactors, that could be operated in parallel and/or in series.

The primary alkylation zone is operated under superatmospheric pressure (5 to 8 bar gauge) and elevated temperature (105° C. to 110° C.) and for a residence time of 100-120 minutes. These conditions are selected to cause the carbon tetrachloride and ethene to form 1,1,1,3-Tetrachloropropane in an alkylation reaction. However, it has been found that the total conversion of carbon tetrachloride to 1,1,1,3-Tetrachloropropane is undesirable as this also results in the formation of unwanted impurities. Thus the level of conversion of the carbon tetrachloride to the chlorinated $C_{3-6}$ alkane of interest is controlled and, in this embodiment of the invention, is not permitted to proceed beyond 95% Control of the progress of the alkylation reaction is achieved partly through use of reaction conditions which do not favour the total conversion of carbon tetrachloride to 1,1,1, 3-Tetrachloropropane, through control of the residence time of the reaction mixture in the continuously stirred tank reactor.

Reaction mixture comprising i) unreacted carbon tetrachloride and ethene, ii) 1,1,1,3-Tetrachloropropane (the chlorinated $C_{3-6}$ alkane of interest in this embodiment) and iii) tributyl phosphate/iron chloride catalyst is extracted from the primary alkylation zone (the continuously stirred tank reactor 3) and fed into a plug/flow reactor 4 (in which the principal alkylation zone is located).

The reaction mixture is extracted such that particulate iron catalyst present in the primary alkylation zone 3 is not extracted and thus the reaction mixture is substantially free of particulate material. Further, in the illustrated embodiment, no additional catalyst is added into the plug/flow reactor 4, although the plug/flow reactor 4 may provided with a catalyst bed. Additionally, no further ethene is added into the plug/flow reactor 4.

In the illustrated embodiment, the operating pressure in the principal alkylation zone 4 is the same as that in the primary alkylation zone 3. The residence time of the reaction mixture is about 30 minutes, which in the illustrated embodiment was sufficient to result in substantially all of the ethene present being used up in the reaction. Of course, it will be understood that for different reactor types and operating conditions, different resident times may be optimal.

When the determined optimal residence time of the reaction mixture in the principal alkylation zone has been reached, reaction mixture is extracted therefrom via line 5, while being maintained at elevated pressure and temperature, and fed into flash evaporation vessel 6. In this vessel, the extracted reaction mixture is subjected to depressurisation, to atmospheric pressure. This pressure drop causes evaporation of the ethene present in the reaction mixture. The 1,1,1,3-Tetrachloropropane-rich mixture, now with substantially no ethene present, is extracted from the flash vessel via line 7 and subjected to the distillation step shown in FIG. 2, and discussed below in more detail.

The evaporated ethene is extracted from the flash vessel 6 via line 8 and fed through a condenser 9. The ethene is then fed via line 10 into absorption column 11 where it is contacted with a stream of carbon tetrachloride and tributyl phosphate/iron chloride catalyst, recovered from the reaction mixture in the aqueous treatment step shown in FIG. 3, and discussed below in more detail. The stream of recovered catalyst/carbon tetrachloride 13 is passed through a cooler 14 and then fed via line 15 into the absorption column 11.

The flow of cooled carbon tetrachloride/catalyst through the absorption column 11 has the effect of trapping the ethene therein. The obtained liquid flow of carbon tetrachloride/catalyst/ethene is then fed back into the continuously stirred tank reactor 3.

As is apparent from FIG. 1, the illustrated embodiment includes an ethene recycling loop which is advantageous for several reasons. First, almost total utilisation of the ethene is achieved and thus the amount of ethene lost from the system is very low. Additionally, the energy requirements of the components of the ethene recycling system are also low. Further, the amount of ethene lost from the system is also very low, meaning that the environmental burden is reduced.

Turning now to FIG. 2, the 1,1,1,3-Tetrachloropropane-rich mixture extracted from the flash vessel shown with reference numeral 7 in FIG. 1, is fed via line 101 into a batch distillation boiler 102 which is operated in communication with a vacuum distillation column 104. The distillation boiler is operated at a temperature of 90° C. to 95° C. Chloroalkanes present in the mixture fed into the boiler 102 are evaporated and separated using distillation column 104 (and the downstream condenser 106 and reflux divider 108) into light ends stream 110.1, carbon tetrachloride stream 110.2, tetrachloroethene stream 110.3 and purified 1,1,1,3-Tetrachloropropane product stream 110.4.

The light ends and tetrachloroethene streams 110.1, 110.3 may be used in the production of carbon tetrachloride, advantageously minimising the production of waste products. This can be achieved through use of a high temperature chlorinolysis process.

The carbon tetrachloride stream 110.2 is recycled back into the continuously stirred tank reactor shown with reference numeral 3 in FIG. 1. The purified 1,1,1,3-Tetrachloropropane product stream 110.4 is extracted from the system and may be stored for shipment or employed in downstream processes requiring pure 1,1,1,3-Tetrachloropropane as a starting material.

A 1,1,1,3-Tetrachloropropane-rich mixture which also comprises catalyst is extracted as a residue from boiler 102 via line 103 and is subjected to the catalyst recovery step shown in FIG. 3.

In that step, the 1,1,1,3-Tetrachloropropane-rich mixture is fed into a batch distillation boiler 204 via line 202, along with a weak (1-5%) hydrochloric acid solution via line 201.

Advantageously, the water present in the acid solution deactivates the catalyst system and protects it from thermal damage. This enables the catalyst system, to be recovered from the 1,1,1,3-Tetrachloropropane-rich mixture, and it can be easily reactivated, post-recovery, and reused in the alkylation process without any significant loss in catalytic activity.

The batch distillation boiler is operated at a temperature of about 100° C., to create a gaseous mixture comprising 1,1,1,3-Tetrachloropropane and water vapour.

The gaseous mixture produced in the boiler 204, is then subjected to steam distillation (or steam stripping) of crude 1,1,1,3-Tetrachloropropane in column 210, which is coupled to the boiler 204. The crude 1,1,1,3-Tetrachloropropane is extracted from the distillation column 210 via line 211, condensed with a condenser 212, fed via line 213 to a reflux liquid-liquid separator 214. Water from the gaseous mixture is fed back to the distillation column 210 via line 215, and a portion is taken off via line 216 for a further distillation step, shown in more detail in FIG. 4 and discussed below in more detail.

The operating temperature of the boiler 204 is then reduced to stop steam stripping, resulting in the condensation of the water vapour present therein. This results in the formation of a biphasic mixture containing an aqueous phase and an organic phase containing the catalyst system, which has not be subjected to steam stripping. To facilitate extraction of the organic phase, a haloalkane extraction agent (in this case, 1,1,1,3-Tetrachloropropane) is added to the boiler 204 via line 203 to increase the volume of that phase.

Extraction of the organic phase from the biphasic mixture is achieved by the sequential extraction of the phases from the boiler 204 via line 205. The organic phase is extracted from the boiler 204 via line 205 and is filtered 206. A filter cake is removed from the filter 206 via line 207. The organic phase is extracted via line 208 and, in this embodiment, fed back to the primary alkylation zone, as shown in FIG. 1, specifically via line 13 in FIG. 1. The aqueous phase is extracted via line 205, filtered 206 and disposed of via line 209.

The stripped crude 1,1,1,3-Tetrachloropropane product is subjected to a further distillation step shown in FIG. 4. In that step, the crude product is fed into a distillation boiler 302 via line 301. The boiler 302 is in communication with distillation column 304. Evaporated chlorinated organic compounds present in the crude 1,1,1,3-Tetrachloropropane are separated in the distillation column 304 (and related downstream apparatus, condenser 306 and reflux divider 308) into a purified 1,1,1,3-Tetrachloropropane product stream 310.1 and chlorinated pentane/pentene stream 310.2.

The chlorinated pentane/pentene stream 310.2 may be used in the production of carbon tetrachloride, advantageously minimising the production of waste products. This can be achieved through use of a high temperature chlorinolysis process.

The purified 1,1,1,3-Tetrachloropropane product stream 310.1 is extracted from the system and may be combined with the major product stream (identified with reference numeral 110.4 in FIG. 2. The product may be stored for shipment or employed in downstream processes requiring pure 1,1,1,3-Tetrachloropropane as a starting material.

The heavy ends residue extracted from the boiler 302 via line 303 is either disposed of or further processed.

Using the apparatus and process conditions outlined above, 2635 kg of carbon tetrachloride (CTC, 99.97% purity) was continuously processed with an average hourly loading 78.2 kg/h to produce 1,1,1,3-Tetrachlorpropene (1113TeCPa). Basic parameters of disclosed process carried out according to Example 2 are as following.

| Basic parameters | |
|---|---|
| First reactor mean residence time (min) | 118 |
| First reactor temperature range (° C.) | 100-110 |
| First reactor pressure (kPa) | 800 |
| Second reactor mean residence time (min) | 25 |
| Second reactor temperature range (° C.) | 100-110 |
| Second reactor pressure (kPa) | 800 |
| Overall reaction CTC conversion (%) | 91.0 |
| Overall 1113TeCpa reaction yield (mol TeCPa/mol CTC converted, in %) | 95.5 |
| Overall 1113TeCpa yield including the all process steps described in Example 2 | 94.0 |

The full impurity profile of the purified product of the above-described embodiment is presented in the following table. Please note that the figures are given as a weighted average of the profiles for the product obtained in line 110.4 in FIG. 2 and line 310.1 in FIG. 4.

| Compound | (% wt) |
|---|---|
| Trichloromethane | 0 |
| 1,2-Dichloroethane | 0 |
| 1-chlorobutane | 0.023 |
| Tetrachloromethane | 0.008 |
| 1,1,1-Trichloropropane | 0.001 |
| Tetrachloroethene | 0.006 |
| 1,1,3-Trichlororoprop-1-ene | 0.014 |
| 1,1,1,3-Tetrachloropropane | 99.925 |
| 1,1,1,3,3-Pentachloropropane | 0.004 |
| hexachloroethane | 0.012 |
| 1,1,1,2,3-Pentachloropropane | 0.005 |
| 1,1,1,5-Tetrachloropentane | 0 |
| 1,3,3,5-Tetrachloropentane | 0 |
| Tributylphosphate | 0 |
| Unknown | 0.007 |

Example 3

Effect on Selectivity of Molar Ratio of Starting Material:Product in Reaction Mixture These examples were carried out using the equipment and techniques outlined above in the 'Continuous Arrangement' in Example 1, except where otherwise stated. The molar ratio of the chlorinated $C_{3-6}$ alkane product (in this case, 1,1,1,3-Tetrachloropropane):carbon tetrachloride in the reaction mixture was controlled to differing levels, principally by the residence time of reaction mixture in the alkylation zone. Temperature was maintained at 110° C. and pressure was maintained at 9 Bar. The selectivities towards product of interest are reported in the following table:

| Trial No. | mol. ratio 1113TeCPa:Tetra-chloromethane | Selectivity of Tetrachloromethane towards 1113TeCPa |
|---|---|---|
| 3-1 | 79.0:21.0 | 96.6 |
| 3-2 | 84.4:15.6 | 95.2 |
| 3-3 | 89.8:10.2 | 95.5 |
| 3-4 | 93.9:6.1 | 94.1 |
| 3-5 | 98.0:2.0 | 90.3 |

As can be seen from this example, when the molar ratio of product:starting material exceeds 95:5 when the process is operated on a continuous basis, there is a notable reduction in selectivity towards the product of interest.

Example 4

Effect on Selectivity of Molar Ratio of Starting Material:Product in Reaction Mixture These examples were carried out using the equipment and techniques as illustrated in FIG. 1, with reference to the accompanying text in Example 2 above, except where otherwise stated. The molar ratio of the chlorinated $C_{3-6}$ alkane product (in this case, 1,1,1,3-Tetrachloropropane):carbon tetrachloride in the reaction mixture was controlled to differing levels, principally by control of the feed rate of the ethylene starting material. Temperature was constantly 110° C. The selectivities towards the product of interest are reported in the following table:

| Trial No. | mol. ratio 1113TeCPa:Tetra-chloromethane | Selectivity of Tetrachloromethane towards 1113TeCPa |
|---|---|---|
| 4-1 | 91.5:8.5 | 95.6 |
| 4-2 | 95.3:4.7 | 94.8 |
| 4-3 | 96.4:3.6 | 93.3 |
| 4-4 | 97.0:3.0 | 92.9 |

As can be seen from this example, when the molar ratio of product:starting material exceeds 95:5 when the process is operated on a continuous basis, there is a notable reduction in selectivity towards the product of interest.

Example 5

Effects of Feedstock Purity

These examples were carried out using the equipment and techniques as illustrated in FIG. 2, with reference to the accompanying text in Example 2 above, except where otherwise stated. Trial 5-1 is the stream obtained from stream 110.4 in FIG. 2. Trials 5-2-5-5 are alternative examples, obtained using the same apparatus and techniques, but employing feedstocks of differing purity. The data below demonstrates that although lower purity feedstock was used in trials 5-2 to 5-5, this advantageously does not significantly impact product purity when obtained from step 1) of the process of the present invention.

| Compounds | Trial No. | | | | |
|---|---|---|---|---|---|
| | 5-1 | 5-2 | 5-3 | 5-4 | 5-5 |
| 1-chlorobutane | 0.004 | 0.028 | 0.032 | 0.011 | 0.002 |
| TeCM | 0.0004 | 0.007 | 0.004 | 0.014 | 0.006 |
| 1,1,1-trichloropropane | 0 | 0 | 0.0005 | 0.004 | 0.009 |
| Tetrachloroethene | 0.002 | 0.001 | 0.002 | 0.02 | 0.052 |
| 1,1,3-trichloropropene | 0.01 | 0.025 | 0.017 | 0.013 | 0.065 |
| 1,1,1,3-tetrachloropropane | 99.96 | 99.81 | 99.92 | 99.89 | 99.836 |
| 1,1,1,3,3-pentachloropropane | 0.0002 | 0.017 | ND | ND | ND |
| Hexachlorethane | 0.002 | 0.079 | 0.002 | 0.013 | 0.001 |
| 1,1,1,2,3-pentachloropropane | 0.0004 | 0.003 | 0 | 0.004 | ND |
| Others | 0.023 | 0.033 | 0.022 | 0.031 | 0.028 |

Example 6

CSTR and Plug Flow Combination

These examples were carried out using the equipment and techniques as illustrated in FIG. 1, with reference to the accompanying text in Example 2 above, except where otherwise stated. The efficiency of reaction in the second plug-flow reactor (reference numeral 4 in FIG. 1) was evaluated. Two trials were conducted with differing amount of dissolved ethylene at the inlet of the plug-flow reactor which was operated at the same temperature, 110° C., as the main CSTR reactor (reference numeral 3 in FIG. 1). The results are shown in the following table:

| Trial No. | Ethylene content at plug-flow reactor inlet (%) | TeCM content at plug-flow reactor intlet (%) | Ethylene content at plug-flow reactor outlet (%) | TeCM content at plug-flow reactor outlet (%) |
|---|---|---|---|---|
| 6-1 | 1.19 | 12.5 | 0.087 | 6.58 |
| 6-2 | 0.36 | 9.17 | 0.089 | 6.99 |

As can be seen from this example, there is a conversion of ethylene between 75-93% in the plug-flow reactor. Thus if plug-flow reactor is employed there is more efficient ethylene utilization in the reaction section. The serial plug-flow reactor allows the CSTR reactor to be operated at an optimal pressure, without needing complex and uneconomical ethylene recovery processes. The serial plug reactor therefore controls the ethylene use in an efficient closed loop.

Example 7

Problematic Degradation of Catalyst Ligand During Conventional Distillation

Fractional distillation equipment consisting of a 2-litre glass distillation four-neck flask equipped with condenser, thermometer, heating bath and vacuum pump system was set up. The distillation flask was initially filled with 1976 grams of reaction mixture obtained using the apparatus and techniques illustrated in FIG. 1 and explained in the accompanying text in Example 2 above.

During distillation, pressure was gradually reduced from an initial pressure of 100 mmHg to a final pressure of 6 mmHg. During this period, 1792 grams of distillate (in different fractions) were extracted. During distillation, there was visible HCl gas formation and furthermore chlorobutane (the breakdown product from tributylphosphate ligand) was also formed in significant amounts namely between 1 to 19% for the distillate fractions. Upon these observations being made, the distillation was interrupted, distillation residue was weighed and analyzed and was found to have a Tetrachloropropane content of 16%. It was no longer possible to continue distillation without significant degradation of the Tributylphosphate ligand.

Example 8

Production of 1,1,3-trichloropropene from 1,1,1,3-tetrachloropropane

FIG. 5 shows a schematic drawing of a system which can be used to operate processes of step 2) of the present invention. 1,1,1,3-tetrachloropropane and ferric chloride are added into the continuously stirred tank reactor 403 via lines 401 and 402. The addition of ferric chloride is conducted using a controlled feed. The continuously stirred tank reactor is operated at a temperature of 140° C. to 145° C. and at atmospheric pressure.

The 1,1,1,3-tetrachloropropane is converted to 1,1,3-trichloropropene in the continuously stirred tank reactor 403, which fulfils the role of the dehydrochlorination zone. The residence time of the reaction mixture in the reactor 403 is limited to prevent the excessive conversion of 1,1,1,3-tetrachloropropane to 1,1,3-trichloropropene and thus, the molar ratio of 1,1,3-trichloropropene:1,1,1,3-tetrachloropropane does not exceed 50:50.

A proportion of 1,1,3-trichloropropene is extracted from the reaction mixture through the use of distillation column 408. Reaction mixture is fed into the bottom of the distillation column 408 and a 1,1,3-trichloropropene rich stream is withdrawn as overhead vapours via line 409. A partial condenser 410 functions to extract gaseous hydrogen chloride from the 1,1,3-trichloropropene rich stream via line 411. The 1,1,3-trichloropropene rich stream is then fed via line 412 to a reflux divider 413, and a stream of purified 1,1,3-trichloropropene is taken off via line 415. A proportion of the 1,1,3-trichloropropene rich stream is fed back as a reflux to distillation column 408 via line 414.

A mixture comprising catalyst, unreacted 1,1,1,3-tetrachloropropane and a limited amount of 1,1,3-trichloropropene is extracted via line 404 from the reactor 403 to a filter 405. The obtained filter cake is extracted via line 406 and the filtrate is passed via line 407 for aqueous treatment, as shown in FIG. 6.

In FIG. 6, the mixture from the reactor in FIG. 5 is fed via line 502 into a washing tank 505 including a stripping boiler. For better liquid phase separation efficiency, 1,1,1,3 tetrachloropropane or another haloalkane extraction agent is fed into the washing tank via line 503. Aqueous hydrochloric acid is fed into the washing tank 505 via line 501.

A biphasic mixture is formed in the tank 505 and the organic phase is extracted from the tank 505 via line 506, filtered 507 and taken via line 509 for further treatment, as shown in FIG. 7. The remaining aqueous phase is extracted via line 510 for further treatment. The filter cake is extracted (508) 1,1,1,3-tetrachloropropane and 1,1,3-trichloropropene dissolved in the aqueous layer present in the washing tank 505 are extracted therefrom by means of a steam distillation column 511. Stripped chlorinated alkanes are passed via line 512 from the distillation column 511 to a condenser 513 and then via line 514 to a reflux liquid-liquid separator 515 where two layers are formed. The stripped 1,1,1,3-tetrachloropropane is then taken off as an organic phase via line 517 and an aqueous phase is refluxed back to the distillation column via line 516.

Turning to FIG. 7, the organic phase is fed via line 601 into distillation boiler 602. 1,1,1,3-tetrachloropropane and 1,1,3-trichloropropene are extracted from the formed mixture using distillation column 607, condenser 609 and reflux divider 611 to produce fractions of 1,1,3-trichloropropene 613.1 and 1,1,1,3-tetrachloropropane 613.2. The fraction of 1,1,1,3-tetrachloropropane is recycled back to the dehydrochlorination zone while the fraction of 1,1,3-trichloropropene is stored or transported for use in downstream reactions employing that chlorinated alkene as a starting material.

A heavy ends residue is extracted from boiler 602 via line 603 and filtered 604. The obtained filter cake and liquid residue are extracted via lines 605 and 606 respectively and recycled or treated.

Using the apparatus and process conditions outlined above, 3563 kg of 1,1,1,3-Tetrachloropropane (1113TeCPa, 99.925% purity) was continuously processed with an average hourly loading 63.1 kg/h to produce 1,1,3-Trichloropropene (113TCPe). Basic parameters of disclosed process carried out according to Example 8 are as following.

| Basic parameters | |
|---|---|
| Reactor mean residence time (min) | 174 |
| Reactor temperature (° C.) | 141 |
| Reactor pressure (kPa) | 101 |
| Overall reaction 1113TeCPa conversion (%) | 91.7 |

| Basic parameters | |
|---|---|
| Overall 113TCpe reaction yield (mol TCPe/mol TeCPa converted, in %) | 97.4 |
| Overall 113TCpe yield including the all process steps described in Example 8 | 96.5 |

The full impurity profile of the purified product of the above-described embodiment is presented in the following table. The figures are given as a weighted average of the profiles for the product obtained in line 415 in FIG. 5 and line 613.1 in FIG. 7.

| Pilot plant | Wt % |
|---|---|
| Perchloroethylene | 0.011 |
| 1,1,3-Trichloropropene | 97.093 |
| 2,3-dichloropropanoyl chloride | 0.028 |
| 1,1,3,3-Tetrachloropropene | 0.019 |
| 1,1,1,3-Tetrachloropropane | 2.573 |
| unknown | 0.276 |

As can be seen, step 2) of the process of the present invention can be operated to produce highly pure chlorinated alkene material.

Example 9

Production of 1,1,3-trichloropropane from 1,1,1,3-tetrachloropropane

This example was conducted using the apparatus and techniques employed in Example 8 above, except where otherwise stated. The continuously stirred tank reactor was operated at a temperature of 149° C. and at atmospheric pressure. The molar ratio of 1,1,3-trichloropropene:1,1,1,3-tetrachloropropane in the reactor was controlled such that it did not exceed 30:70. Using the apparatus and process conditions outlined in Example 8 above, 1543.8 kg of 1,1,1,3-Tetrachloropropane (1113TeCPa, 99.901% purity) was continuously processed with an average hourly loading 47.5 kg/h to produce 1,1,3-Trichloropropene (113TCPe). Catalyst was added in the form of $FeCl_3$ aqueous solution to provide a catalyst content of 66 ppm, based on feedstock 1113TeCPa. Basic parameters of disclosed process carried out according to Example 8 are as following.

| Basic parameters | |
|---|---|
| Reactor mean residence time (min) | 287 |
| Reactor temperature (° C.) | 149 |
| Reactor pressure (kPa) | 101 |
| Overall reaction 1113TeCPa conversion (%) | 91.4 |
| Overall 113TCPe reaction yield (mol TCPe/mol TeCPa converted, in %) | 98.7 |
| Overall 113TCPe yield in % including the all process steps described in Example 9 | 97.8 |

The full impurity profile of the product of the above-described embodiment is presented in the following table. The figures are given as a weighted average of the profiles for the product obtained in line 415 in FIG. 5 and line 613.1 in FIG. 7.

| Compound | Wt % |
|---|---|
| Perchloroethylene | 0.006 |
| 3,3,3-Trichloropropene | 0.038 |
| 1,1,3-Trichloropropene | 99.347 |
| 2,3-dichloropropanoyl chloride | 0.045 |
| 1,1,3,3-Tetrachloropropene | 0.004 |
| 1,1,1,3-Tetrachloropropane | 0.322 |
| unknown | 0.238 |

As can be seen, when the dehydrochlorination reaction is controlled such that the molar ratio of 1,1,3-trichloropropene:1,1,1,3-tetrachloropropane does not exceed 30:70, the process of step 2) the present invention can be operated to produce highly pure chlorinated alkene material with the very high selectivity and in high yield. Of note is that 3,3,3-trichloropropene is only formed in trace amounts. This is particularly advantageous as 3,3,3-trichloropropene is a very reactive olefin contaminant with a free induced (activated) double bond and can be a precursor of highly problematic oxygenated impurities.

Example 10

Alkene:Alkane Ratio in Reaction Mixture

These examples were conducted using the apparatus and techniques employed in Example 8 above, except where otherwise stated. In each of these trials, the reaction progress was controlled such that there was a different ratio between 1,1,3-Trichloropropene:1,1,1,3-Tetrachloropropane in the reaction mixture present in the reactor (403, FIG. 5) reaction mixture (407, FIG. 5) in each trial. The amount of dosed catalyst $FeCl_3$ was controlled to maintain the reaction conversion rate at about 90%. The influence of different levels of 113TCPe in reaction mixture on the heavy oligomers formation and catalyst deactivation is shown in the following tables:

| Heavy Oligomer Formation | | | | | | |
|---|---|---|---|---|---|---|
| | 10-1 | 10-2 | 10-3 | 10-4 | 10-5 | 10-6 |
| Calculated TCPe:TeCPa molar ratio in reac. mix | 23:77 | 22:78 | 34:66 | 43:57 | 46:54 | 43:57 |
| TCPe (%) in reaction mixture | 18.95 | 18.25 | 27.6 | 34.54 | 32.01 | 34.31 |
| Heavy oligomers/TCPe | 0.36% | 0.40% | 1.05% | 1.57% | 2.87% | 2.54% |
| | 10-7 | 10-8 | 10-9 | 10-10 | 10-11 | 10-12 |
| Calculated TCPe:TeCPa molar ratio in reac. mix | 39:61 | 37:63 | 40:60 | 39:61 | 38:62 | 39:31 |
| TCPe (%) in reaction mixture | 32.1 | 29.94 | 32.84 | 31.46 | 30.56 | 31.83 |
| Heavy oligomers/TCPe | 1.56% | 1.79% | 1.65% | 1.01% | 1.47% | 1.55% |

| Catalyst Deactivation | | | | | | |
|---|---|---|---|---|---|---|
| | 10-1 | 10-2 | 10-3 | 10-4 | 10-5 | 10-6 |
| TCPe (%) in reaction mixture | 18.95 | 22.36 | 27.6 | 34.54 | 32.01 | 34,313 – 1 |
| Calculated TCPe:TeCPa molar ratio in reac. mix | 23:77 | 22:78 | 34:66 | 43:57 | 46:54 | 43:57 |
| Required conc. of FeCl3 in feedstock | 26.5 | 26.5 | 66 | 101 | 116 | 78 |
| | 10-7 | 10-8 | 10-9 | 10-10 | 10-11 | 10-12 |
| TCPe (%) in reaction mixture | 32.1 | 29.94 | 32.84 | 31.46 | 30.56 | 31.83 |
| Calculated TCPe:TeCPa molar ratio in reac. mix | 39:61 | 37:63 | 40:60 | 39:61 | 38:62 | 39:61 |
| Required conc. of FeCl3 in feedstock | 132 | 132 | 105 | 177 | 106 | 74 |

As can be seen from this example, when the specific apparatus and techniques employed, an increase in the molar ratio of the product to starting material (increased amount of the product in the reaction mixture) in step 2) of the process of the present invention, this corresponds to an increase in the formation of heavy oligomers. Further, if the 1,1,3-Trichloropropene concentration is high, catalyst deactivation was also observed.

Example 11

Compatibility of the Product Fluid with Various Materials

An Erlenmeyer glass flask was filled with pure distilled 1,1,3-Trichloropropene with purity of >99%. The test construction material sample was immersed in the liquid and the system was closed with a plastic plug.

Samples of the Trichloropropene were regularly taken from the flask. The construction material samples were weighed before and after trail. The temperature of the liquid was ambient laboratory conditions, around 25° C.

The major changes in the quality of the Trichloropropene are shown in the following table, as a % change in purity:

|  | Feedstock | 11-1 | 11-2 | 11-3 | 11-4 |
|---|---|---|---|---|---|
| Trial duration | 0 day | 29 days | 29 days | 30 days | 30 days |
| Construction Material |  | CS | SS 1.4541 | Ti | C-276 |
| 1,1,3-Trichloropropene - relative change (%) | 0 | −53.75 | −3.70 | −3.27 | −0.67 |
| Sum of oligomers (%) | 0 | 42.68 | 0.20 | 0.32 | 0.01 |

CS=carbon steel, SS=stainless steel, Ti=Titanium, C-276=Hastelloy C-276

In a second set of trials, an Erlenmeyer glass flask equipped with a back cooler and oil heating bath with controlled temperature was filled with pure distilled 1,1,3-Trichlorpropene with a purity of >99%. The test material sample was immersed in the liquid and the system was partially closed using a plastic plug. Samples of Trichloropropene were regularly taken from the flask. The material samples were weighed before and after trail. The temperature of the liquid was controlled at 100° C. The major changes in the liquid Trichloropropene are shown in the following table:

|  | feedstock | 11-5 | 11-6 | 11-7 | 11-8 |
|---|---|---|---|---|---|
| Trial duration | 0 day | 5 hours | 48 hours | 5 hours | 48 hours |
| Construction Material |  | Glass as material of flask |  | Impregnated graphite |  |
| 1,1,3-Trichloropropene - relative change (%) | 0 | −0.32 | −2.31 | −0.30 | −2.00 |
| Sum of oligomers (%) | 0 | 0.05 | 0.28 | 0.05 | 0.34 |

|  | feedstock | 11-9 | 11-10 | 11-11 | 11-12 |
|---|---|---|---|---|---|
| Trial duration | 0 hours | 5 hours | 48 hours | 5 hours | 48 hours |
| Construction Material |  | SS 1.4341 |  | SS 1.4541 |  |
| 1,1,3-Trichloropropene - relative change (%) | 0 | −0.54 | −3.08 | −0.51 | −2.80 |
| Sum of oligomers (%) | 0 | 0.27 | 1.01 | 0.29 | 1.29 |

As can be seen from this example, the use of carbon steel appears to be challenging as it is not compatible with the process fluid consisting of 1,1,3-Trichloropropene. Stainless steel and titanium have also poor performance, resulting in the formation of significant amounts of oligomers are formed. From the tested metal materials, the Ni-alloy Hastelloy C-276 has excellent results. It can be seen also that glass (or enamel) and other non-metallic material, such as phenolic resin impregnated graphite, are also more suitable.

Example 12

Problematic Chlorinated Alkene Impurities

In many downstream reactions in which chlorinated alkenes are used as starting materials, the presence of oxygenated organic impurities is problematic. This example demonstrates that certain impurities have a surprising propensity to form such compounds.

A four neck glass flask equipped with a stirrer, thermometer, back cooler, feed and discharge neck and cooling bath was filled with water and chlorine gas was bubbled into the water to produce a weak solution of hypochlorous acid. When an appropriate amount of chlorine had been introduced into the water, a feedstock consisting obtained from the process of Example 8 comprising 1,1,3-Trichloropropene with a purity of 98.9% was slowly dropped into the prepared solution of hypochlorous acid for a period of 90 min and cooled. The pressure was atmospheric and the operating temperature was close to 20° C. The same procedure was repeated with 3,3,3-Trichloropropene having a purity of 68.1%. After reaction completion the systems formed bi-phasic mixtures. The organic phase (product) was extracted and then analyzed by gas chromatography. The results are shown in the following table:

|  | 12-1 | | 12-2 | |
|---|---|---|---|---|
| Hypochlorination of Trichloropropenes | Feedstock (%) | Product (%) | Feedstock (%) | Product (%) |
| 3,3,3-Trichloropropene | 68.063 | 33.544 | 0.024 | 0.023 |
| 1,1,3-Trichloropropene | 21.772 | 16.651 | 98.922 | 91.374 |
| 1,1,1,2,3-Pentachloropropane |  | 20.942 |  | 6.800 |
| 1,1,1,3-Tetrachloropropan-2-ol |  | 12.792 |  | 0.018 |

As can be seen from this example, 1,1,3-Trichlorpropene reacts with chlorine in water to produce 1,1,1,2,3-Pentachloropropane, while 3,3,3-Trichloropropene reacts significantly to produce corresponding tetrachlorohydrines, especially 1,1,1,3-Tetrachloropropan-2-ol.

In other words, 1,1,3-Trichlorpropene reacts to produce a product of commercial interest, while 3,3,3-Trichloropropene reacts to the produce an oxygenated impurity which cannot be easily removed from the 1,1,1,2,3-Pentachloropropane. As is apparent from Examples 8 and 9 above, the processes of step 2) of the present invention can be advantageously employed to produce 1,1,3-trichloropropene resulting in the formation of only trace amounts of 3,3,3-trichloropropene.

Example 13

Continuous Production of 1,1,1,2,3-pentachloropropane

A schematic diagram of the equipment used to perform the primary conversion step and principal conversion step in step 3-a) of the process of the present invention is provided as FIG. 8. A liquid stream of 1,1,3-trichloropropene is fed via line 706 into an external circulation loop 703, 705, 707 connected to a column gas-liquid reactor 702. Gaseous chlorine is fed in the reactor 702 via line 701. The reactor 702 is includes a single primary reaction zone, namely circulation loop 703, 705, 707 and lower part of the reactor 702. The circulation loop 703, 705, 707 is provided with an external cooler 704 to control the temperature of the reaction mixture. Thorough mixing of 1,1,3-trichloropropene and chlorine is achieved within the primary reaction zone. The primary conversion step could equally be conducted in one or more other types of reactor, such as continuously stirred tank reactor/s.

The operating temperature within the primary reaction zone is 0° C. to 20° C. Operating the reactor within this range was found to minimise the formation of pentachloropropane isomers, which are difficult to separate from the target product, 1,1,1,2,3-pentachloropropane. Thorough mixing of the reaction mixture and mild temperatures, but also controlling the proportion of 1,1,1,2,3-pentachloropropane present in the reaction mixture, was found to minimise serial reactions of 1,1,3-trichloropropene and the formation of 1,1,1,3,3-pentachloropropane (which is difficult to separate from 1,1,1,2,3-pentachloropropane). To increase the rate of reaction at the low temperatures, the reaction mixture is exposed to visible light.

The reaction mixture is then passed up through the reactor 702 for the principal conversion step, which is performed as a reduced temperature conversion step. Cooling of the reaction mixture is achieved using cooling tubes, and the reaction mixture is passed through a series of upstream and downstream principal reaction zones (not shown), resulting in zonal chlorination of 1,1,3-trichloropropene. To drive the reaction towards completion, the reaction mixture in the downstream principal reaction zone is exposed to ultraviolet light. Advantageously, this fully utilizes the chlorine starting material such that the obtained reaction mixture which is extracted from the downstream-most principal reaction zone has very low levels of dissolved chlorine.

Operating the principal reaction zones at such temperatures has been found to minimise the serial reactions of 1,1,3-trichloropropene, which result in the formation of unwanted and problematic impurities, such as hexachloropropane.

A 1,1,1,2,3-pentachloropropane rich stream is extracted from reactor 702 via line 708. Off-gas is extracted from the reactor 702 via line 711. The 1,1,1,2,3-pentachloropropane rich stream is subjected to cooling using a product cooler 709 and passed via line 710 for a hydrolysis step. A schematic diagram illustrating the equipment used to conduct this step is presented as FIG. 9.

In that equipment, the 1,1,1,2,3-pentachloropropane rich stream is fed into washing tank 803 via line 802. Water is fed into the washing tank via line 801 to form a biphasic mixture. The organic phase (containing the 1,1,1,2,3-pentachloropropane rich product) can easily be separated from the aqueous phase by the sequential removal of those phases via line 804. The extracted phases are filtered 805 with the filter cake being removed 806. The 1,1,1,2,3-pentachloropropane rich product is then fed via line 807 for further processing while wastewater is removed via line 808.

The hydrolysis step is especially effective at removing oxygenated organic compounds, such as chlorinated propionyl chloride and their corresponding acids and alcohols, which may be formed during upstream steps in the process of the present invention. While the formation of such compounds can be avoided by excluding the presence of oxygen from the upstream stages of the synthesis, doing so increases the cost of production. Thus, the hydrolysis step assists with the economic and straightforward removal of such otherwise problematic (owing to the difficulty of removing them, e.g. by distillation) impurities.

To maximise the purity of the obtained 1,1,1,2,3-pentachloropropane, a vacuum distillation step was performed, using the apparatus shown in FIG. 10, namely a distillation boiler 902 and vacuum distillation column 907. Advantageously, the components of the distillation apparatus which come into contact with the process liquid and distillate are formed of non-metallic materials which prevents the formation of degradation products of the 1,1,1,2,3-pentachloropropane.

The vacuum distillation column 907 is provided with a liquid side stream withdrawal which can be used to prevent contamination of the product stream with light molecular weight compounds which may be formed in the boiler.

The 1,1,1,2,3-pentachloropropane rich product from the apparatus shown in FIG. 9 is fed into boiler 902 via line 901. A residue is extracted from the distillation boiler 902 via line 903, subjected to filtering using a filter 904. The filter cake is extracted from the system 905 and a heavies stream is extracted via line 906 and subjected to further processing.

Distillate is taken from the distillation column 907 via line 908, fed via condenser 909, intermediate line 910 and liquid divider 911 to yield a streams of i) 1,1,3-trichloropropene via line 913.1 which is recycled to the primary reaction zone, ii) 1,1,1,3-tetrachloropropane via line 913.2 and purified 1,1,1,2,3-pentachloropropane via line 913.3. A reflux stream 912 from divider 911 is fed back into the vacuum distillation column 907.

Using the apparatus and process conditions outlined above, 3062 kg of 1,1,3-Trichloropropene (113TCPe, purity 97.577%) was continuously processed with an average hourly loading 44.9 kg/h to produce 1,1,1,2,3-Pentachloropropane (11123PCPa). Basic parameters of the process are as follows:

| Basic parameters | |
| --- | --- |
| Reactor overall mean residence time (min) | 375 |
| Reactor temperature range (° C.) | 1-30 |
| Reactor pressure (kPa) | 101 |
| Overall reaction 113TCPe conversion (%) | 91.3 |
| Overall 11123PCPa reaction yield (mol PCPa/mol TCPe converted, in %) | 97.9 |
| Overall 11123PCPa yield including the all process steps described in Example 13 | 97.4 |

The full impurity profile of the purified product obtained in line 913.3. in FIG. 10 of the above-described embodiment is presented in the following table

| Compound | (% wt) |
| --- | --- |
| Phosgene | ND |
| 1,1,3-Trichloroprop-1-ene | 0.007 |
| 2,3-Dichloropropanoylchloride | ND |
| 1,2.3-Trichloropropane | ND |
| 2,3,3,3-Tetrachloroprop-1-ene | 0.001 |
| 1,1,3,3-Tetrachloroprop-1-ene | 0.003 |
| 1,1,1,3-Tetrachloropropane | 0.002 |
| 1,1,2,3-Tetrachloroprop-1-ene | 0.003 |
| 1,1,3,3,3-Pentachloroprop-1-ene | 0.001 |
| 1,1,1,3,3-Pentachloropropane | 0.004 |
| hexachloroethane | ND |
| 2,3-Dichloropropanoic acid | ND |
| 1,1,1,2,3-Pentachloropropane | 99.967 |
| 1,1,2,2,3-Pentachloropropane | 0.001 |
| 1,1,1,3-Tetrachloropropane-2-ol | 0.001 |
| 1-Bromo-1,1,2,3-Tetrachloropropane | ND |
| 2-Bromo-1,1,1,3-Tetrachloropropane | ND |
| 1,1,1,3,3,3-Hexachloropropane | ND |
| 1,1,1,2,3,3-Hexachloropropane | 0.002 |
| 1,1,1,2,2,3-Hexachloropropane | 0.001 |
| 1,2-Dibromo-1,1,3-Trichloropropane | ND |
| HCl as Cl— | ND |
| $H_2O$ | 0.005 |

ND means below 0.001% wt.

Example 14

Ultra Pure Composition
1,1,1,2,3-pentachloropropane (PCPA)

The process of Example 13 was repeated four times and samples of 1,1,1,2,3-pentachloropropane were obtained following distillation using the apparatus illustrated in FIG. 10. Distillation was conducted at a pressure of around 15 mBar and at a maximum boiler temperature of 105° C. As can be seen in the following table, the process of step 3) of the present invention enables highly pure PCPA, including very low levels of impurities, particularly 1,1,2,2,3-pentachloropropane which is very difficult to separate from 1,1,1,2,3-pentachloropropane using distillation. Note that the figures in this table are provided as percentages by weight of the composition.

| Compound | Trial Number | | | |
|---|---|---|---|---|
| | 14-1 | 14-2 | 14-3 | 14-4 |
| Phosgene | ND | ND | ND | ND |
| 1,1,3-Trichloroprop-1-ene | 0.0014 | 0.0012 | 0.0006 | 0.0014 |
| 2,3-Dichloropropanoyl chloride | ND | ND | ND | ND |
| 1,2.3-Trichloropropane | ND | ND | ND | ND |
| 2,3,3,3-Tetrachloroprop-1-ene | 0.0005 | 0.0002 | <0.0001 | 0.0002 |
| 1,1,3,3-Tetrachloroprop-1-ene | 0.0017 | 0.0021 | 0.0008 | 0.0015 |
| 1,1,1,3-Tetrachloropropane | 0.0023 | 0.0013 | 0.0007 | 0.0013 |
| 1,1,2,3-Tetrachloroprop-1-ene | 0.0018 | 0.0021 | 0.0008 | 0.0011 |
| 1,1,3,3,3-Pentachloroprop-1-ene | ND | ND | ND | ND |
| 1,1,1,3,3-Pentachloropropane | 0.002 | 0.0022 | 0.0009 | 0.0016 |
| hexachloroethane | ND | ND | ND | <0.0001 |
| 2,3-Dichloropropanoic acid | ND | ND | ND | ND |
| 1,1,1,2,3-Pentachloropropane | 99.984 | 99.985 | 99.993 | 99.989 |
| 1,1,2,2,3-Pentachloropropane | 0.0006 | 0.0009 | 0.0008 | 0.0009 |
| 1,1,1,3-Tetrachlororopropane-2-ol | 0.001 | 0.0008 | 0.0006 | 0.0005 |
| 1-Bromo-1,1,2,3-Tetrachloropropane | ND | ND | ND | ND |
| 2-Bromo-1,1,1,3-Tetrachloropropane | ND | ND | ND | ND |
| 1,1,1,3,3-Hexachloropropane | ND | ND | ND | ND |
| 1,1,1,2,3-Hexachloropropane | 0.0006 | 0.0004 | ND | 0.0005 |
| 1,1,1,2,2,3-Hexachloropropane | ND | 0.0003 | ND | ND |
| 1,2-Dibromo-1,1,3-Trichloropropane | ND | ND | ND | ND |
| Moisture (mg/kg) | 44 | 23 | NP | NP |
| Iron (mg/kg) | <0.05 | 0.05 | NP | NP |
| HCl as Chlorides (mg/kg) | 0.51 | 0.53 | NP | NP |

ND = below 1 ppm,
NP = not performed

Example 15

Effect of Water Treatment

Crude 1,1,1,2,3-Pentachloropropane compositions were obtained using the apparatus depicted in FIG. 8 and described in Example 13 above, e.g. the compositions were obtained from line 710 in FIG. 8. One stream (Trial 15-1) was not subjected to a hydrolysis step, while the other was (Trial 15-2), using the apparatus shown in FIG. 9 and described in Example 13 above. The resulting crude compositions were then subjected to distillation. The purity of and oxygenated compound contents of the samples, pre- and post-distillation, are shown in the following table:

| Trial Number | 15-1 | 15-2 |
|---|---|---|
| Pre-distillation | | |
| 1,1,1,2,3-Pentachloropropane | 89.038 | 91.402 |
| Sum of oxygenated as propanoyl chlorides and their acids | 0.006 | 0.001 |
| Post-distillation | | |
| 1,1,1,2,3-Pentachloropropane | 99.948 | 99.930 |
| Sum of oxygenated as propanoyl chlorides and their acids | 0.006 | <0.001 |

As is apparent, the washing step can be successfully employed to minimise the content of oxygenated organic impurities in compositions rich in chlorinated alkanes of interest.

Example 16

Influence of Molar Ratio of Chlorinated Alkene:Chlorinated Alkane on Impurity Formation A batch operated reactor consisting of a four neck glass flask equipped with a stirrer, thermometer, back cooler, feed and discharge neck and cooling bath was set up. The feedstock consisted of 1,1,3-Trichloropropene comprising perchlorethylene and oxygenated impurities in amounts observed in commercially sourced supplies.

Minor amounts of HCl gas were formed and these together with traces of chlorine were cooled down by means of a back cooler/condenser and then absorbed in a caustic soda scrubber. Chlorine was introduced into the liquid reaction mixture via dip pipe in various amounts for a period of 90 minutes. The temperature of reaction was maintained at 26 to 31° C. Pressure was atmospheric. The chlorine was totally consumed during the reaction. The reaction mixture was sampled and analyzed by gas chromatography and the results of this analysis are shown in the following table:

| Trial No. | 16-1 | 16-2 | 16-3 | 16-4 | 16-5 |
|---|---|---|---|---|---|
| chlorine dosed (mol % of stoichiometry) | 20% | 40% | 60% | 80% | 100% |
| TCPe:PCPa ratio in reaction mixture (mol %) | 90:10 | 72:28 | 53:47 | 33:67 | 14:86 |
| HCE (w %) | 0.015 | 0.025 | 0.040 | 0.064 | 0.099 |
| DCPC (w %) | 0.089 | 0.067 | 0.172 | 0.228 | 0.322 |
| Other oxygenated (w %) | | 0.009 | 0.017 | 0.030 | 0.058 |

As can be seen, increasing the conversion of the chlorinated alkene starting material to the chlorinated alkane product of interest results in an increase in the formation of impurities in the reaction mixture. These disadvantageous results arise as conversion of the starting material to product approaches total conversion.

Example 17

Influence of Molar Ratio of Chlorinated Alkene:Chlorinated Alkane on Isomeric Selectivity This example was carried out in as described in Example 16 above. 1,1,3-Trichloropropene (purity 94.6% containing 5% of 1,1,1,3-Tetrachloropropane as an impurity) was used as the feedstock.

4 trials at different reaction temperature were conducted. The samples of reaction mixture were taken at 80%, 90%, 95% and 100% of stoichiometric quantity of chlorine dosed (based on 113TCPe in the feedstock) and then analyzed by gas chromatography. The results of this analysis are shown in the following table:

| Chlorine dosed (mol % of 113TCPe in feedstock) | | 80% | 90% | 95% | 100% |
|---|---|---|---|---|---|
| Trial No. | Reaction temp. | 11133PCPA content in reaction mixture in % | | | |
| 17-1 | 6° C. | 0.028 | 0.040 | 0.053 | 0.075 |
| 17-2 | 25° C. | 0.040 | 0.055 | 0.071 | 0.099 |
| 17-3 | 45° C. | 0.049 | 0.064 | 0.076 | 0.095 |
| 17-4 | 63° C. | 0.056 | 0.071 | 0.086 | 0.112 |

These results demonstrate that increasing the conversion of the chlorinated alkene starting material to the chlorinated alkane product of interest results in a decrease in the selectivity of the reaction towards the chlorinated alkane isomer of interest. These disadvantageous results arise as conversion of the starting material to product approaches total conversion.

Example 18

Influence of Molar Ratio of Chlorinated Alkene:Chlorinated Alkane on Impurity Formation This chlorination step was carried out as described in Example 16 above. 1,1,3-Trichloropropene (purity 99.4%) was used as a feedstock.

Chlorine was introduced into the liquid reaction mixture at 120% of the stoichiometric quantity towards feedstock 1,1,3-Trichloropropene for a period of 90 minutes and was totally consumed during the reaction. The reaction temperature was 80° C. and reactor pressure was atmospheric. The samples of reaction mixture were taken by 80%, 95%, 110% and 120% of stoichiometric quantity of the chlorine dosed was analyzed by gas chromatography. Reaction selectivity is expressed in the table below as a ratio between sum of major impurities (1,1,3,3-Tetrachloropropene, 1,1,1,2,3,3-Hexachloropropane, 1,1,1,2.2.3-Hexachloropropane) to the product 1,1,1,2,3-Pentachloropropane:

| Trial Number | 18-1 | 18-2 | 18-3 | 18-4 |
|---|---|---|---|---|
| chlorine dosed (mol % of stoichiometry) | 80 | 95 | 110 | 120 |
| TCPe:PCPa ratio in reaction mixture (mol %) | 22:78 | 11:89 | 0.6:99.4 | 0.2:99.8 |
| Sum of byproducts/ 11123PCPa (%) | 3.51 | 3.59 | 4.28 | 6.34 |

These results demonstrate that increasing the conversion of the chlorinated alkene starting material to the chlorinated alkane product of interest results in an increase in the formation of unwanted impurities. These disadvantageous results arise as conversion of the starting material to product approaches total conversion. As can be seen, the degree of conversion (and thus the formation of impurities) can advantageously and conveniently be achieved by controlling the amount of chlorine into the reaction zone, such that there is no molar excess of chlorine: chlorinated alkene starting material.

Example 19

Removal of Oxygenated Impurities by Hydrolysis

To demonstrate the effectiveness of the hydrolysis step of step 3-b) of the present invention at removing oxygenated compounds from the chlorinated alkane product of interest, samples of crude reaction mixture were obtained using the apparatus depicted in FIG. 8 and described in Example 13 above, e.g. the composition was obtained from line 710 in FIG. 8. The content of a specific oxygenated compound known to be problematic in downstream reactions was analysed (Feed). The sample was then subjected to a hydrolysis step using the apparatus depicted in FIG. 9 and described above in Example 13, and the organic phase, e.g. the composition obtained from line 807 in FIG. 9 was analysed (After treatment). The results are shown in the following table:

| Trial Number | Content of specific oxygenated compound (ppm) | |
|---|---|---|
| 19-1 | Feed | After treatment |
| 2,3-Dichloropropanoyl chloride | 937 | 23 |

As can be seen from this example there is about 97.5% efficiency in the removal of this specific oxygenated impurity.

The invention claimed is:

1. A process for preparing a highly pure 1,1,1,2,3-pentachloropropane product comprising:
   1-a) providing a reaction mixture comprising ethylene, carbon tetrachloride and a catalyst in a principal alkylation zone to produce 1,1,1,3-tetrachloropropane in the reaction mixture, and,
   1-b) treating the reaction mixture obtained in step 1-a) to obtain a 1,1,1,3-tetrachloropropane feedstock;
   2-a) contacting the 1,1,1,3-tetrachloropropane feedstock with a catalyst in a dehydrochlorination zone to produce a reaction mixture comprising 1,1,1,3-tetrachloropropane and 1,1,3-trichloropropene, and
   2-b) treating the reaction mixture obtained in step 2-a) to obtain a 1,1,3-trichloropropene feedstock;
   3-a) contacting the 1,1,3-trichloropropene feedstock with chlorine in a reaction zone to produce a reaction mixture containing 1,1,1,2,3-pentachloropropane and 1,1,3-trichloropropene, the reaction zone being different from the dehydrochlorination zone, and
   3-b) treating the reaction mixture obtained in step 3-a) to obtain the highly pure 1,1,1,2,3-pentachloropropane product wherein, in step 1-a), the concentration of the 1,1,1,3-tetrachloropropane in the reaction mixture in the principal alkylation zone is maintained at a level such that the molar ratio of 1,1,1,3-tetrachloropropane:carbon tetrachloride in the reaction mixture does not exceed:
   95:5 where the principal alkylation zone is in continuous operation, or
   99:1 where the principal alkylation zone is in batchwise operation.

2. The process of claim 1, wherein treatment steps 1-b), 2-b) and/or 3-b) comprise a distillation step.

3. The process of claim 1, wherein treatment steps 1-b), 2-b) and/or 3-b) comprise contacting compositions comprising 1,1,1,3-tetrachloropropane (in the case of step 1-b), 1,1,3-trichloropropene (in the case of step 2-b), and/or 1,1,1,2,3-pentachloropropane (in the case of step 3-b) with an aqueous medium.

4. The process of claim 1, wherein the reaction mixture produced in step 1-a) is extracted from the principal alkylation zone and is subjected to an aqueous treatment step in step 1-b), in which the reaction mixture is contacted with an aqueous medium in an aqueous treatment zone, a biphasic mixture is formed and an organic phase comprising catalyst is extracted from the biphasic mixture.

5. The process of claim 1, wherein the catalyst used in step 1-a) is a metallic catalyst, optionally further comprising an organic ligand.

6. The process of claim 5, wherein the organic ligand is an alkylphosphate.

7. The process of claim 1, wherein the reaction mixture produced in step 1-a) is extracted from a primary alkylation zone and fed into the principal alkylation zone, wherein the ratio of 1,1,1,3-tetrachloropropane:carbon tetrachloride present in the reaction mixture extracted from the principal alkylation zone is greater than the ratio of 1,1,1,3-tetrachloropropane:carbon tetrachloride present in the reaction mixture taken from the primary alkylation zone.

8. The process of claim 1, wherein the amount of unreacted ethylene in the reaction mixture leaving the principal alkylation zone is less than 0.6%.

9. The process of claim 1, wherein any unreacted gaseous ethylene is directly recycled back to the alkylation reaction zone/s operating at elevated pressure.

10. The process of claim 1, wherein any unreacted gaseous ethylene is recycled back to the reaction zone/s operating at elevated pressure by absorbing ethylene into the cold liquid carbon tetrachloride feedstock.

11. The process of claim 1, wherein step 2-b) comprises contacting a mixture comprising 1,1,3-trichloropropene, catalyst and 1,1,1,3-tetrachloropropane with an aqueous medium in an aqueous treatment zone.

12. The process of claim 11, wherein a biphasic mixture is formed in the aqueous treatment zone and an organic phase comprising 1,1,1,3-tetrachloropropane and 1,1,3-trichloropropene is extracted from the biphasic mixture.

13. The process of claim 1, wherein all parts of the dehydrochlorination zone which come into contact with the reaction mixture in step 2-a) have an iron content of about 20% or less and/or are formed from non-metallic materials.

14. The process according to claim 13, wherein the non-metallic materials are selected from the group consisting of enamel, glass, impregnated graphite, silicium carbide, plastics materials and any combination thereof.

15. The process according to claim 14, wherein the impregnated graphite is impregnated with phenolic resin.

16. The process according to claim 14, wherein the plastic materials are selected from the group consisting of polytetrafluoroethylene, perfluoroalkoxy, polyvinylidene fluoride, and any combination thereof.

17. The process of claim 1, wherein at least some parts of the dehydrochlorination zone which come into contact with the reaction mixture in step 2-a) are formed of a nickel-based alloy.

18. The process according to claim 17, wherein the nickel-based alloy comprises nickel, chromium, molybdenum, iron, and tungsten.

19. The process of claim 1, wherein reaction mixture produced in step 3-a) is extracted from the primary reaction zone and is then subjected to a principal conversion step in a principal reaction zone to produce a 1,1,1,2,3-pentachloropropane rich product, which is extracted from the principal reaction zone.

20. The process of claim 19, wherein, in step 3-a), the principal conversion step comprises a reduced temperature conversion step in which the reaction mixture extracted from the primary reaction zone is fed into a principal reaction zone operated at a reduced temperature and the 1,1,1,2,3-pentachloropropane rich product is extracted from the principal reaction zone.

21. The process of claim 19, wherein the primary and/or the principal reaction zone is exposed to visible light and/or ultraviolet light.

22. The process according to claim 19, wherein the 1,1,1,2,3-pentachloropropane rich product produced in step 3-a) is subjected to an aqueous treatment and/or hydrolysis step.

23. The process according to claim 22, wherein the aqueous treatment and/or hydrolysis step comprises contacting the 1,1,1,2,3-pentachloropropane rich product with an aqueous medium in an aqueous treatment zone.

24. The process according to claim 19, wherein step 3-b) comprises one or more distillation steps, carried out on the 1,1,1,2,3-pentachloropropane rich product produced in step 3-a).

25. The process according to claim 19, wherein step 3-b) comprises one or more distillation steps, carried out on an organic phase extracted from the mixture formed in an aqueous treatment zone.

26. The process of claim 1, wherein step 3-b) comprises one or more distillation steps, carried out on the reaction mixture produced in step 3-a).

27. A process for preparing a highly pure 1,1,1,2,3-pentachloropropane product comprising:
 1-a) providing a reaction mixture comprising ethylene, carbon tetrachloride and a catalyst in a principal alkylation zone to produce 1,1,1,3-tetrachloropropane in the reaction mixture, and
 1-b) treating the reaction mixture obtained in step 1-a) to obtain a 1,1,1,3-tetrachloropropane feedstock;
 2-a) contacting the 1,1,1,3-tetrachloropropane feedstock with a metal catalyst, a metal salt catalyst or any combination thereof, in a dehydrochlorination zone to produce a reaction mixture comprising 1,1,1,3-tetrachloropropane and 1,1,3-trichloropropene, and
 2-b) treating the reaction mixture obtained in step 2-a) to obtain a 1,1,3-trichloropropene feedstock;
 3-a) contacting the 1,1,3-trichloropropene feedstock with chlorine in a reaction zone to produce a reaction mixture containing 1,1,1,2,3-pentachloropropane and 1,1,3-trichloropropene, the reaction zone being different from the dehydrochlorination zone, and
 3-b) treating the reaction mixture obtained in step 3-a) to obtain the highly pure 1,1,1,2,3-pentachloropropane product,
wherein the concentration of the 1,1,3-trichloropropene in the reaction mixture produced in step 2-a) in the dehydrochlorination zone is controlled such that the molar ratio of 1,1,3-trichloropropene:1,1,1,3-tetrachloropropane is from 1:99 to 50:50.

28. A process for preparing a highly pure 1,1,1,2,3-pentachloropropane product comprising:
 1-a) providing a reaction mixture comprising ethylene, carbon tetrachloride and a catalyst in a principal alkylation zone to produce 1,1,1,3-tetrachloropropane in the reaction mixture, and
 1-b) treating the reaction mixture obtained in step 1-a) to obtain a 1,1,1,3-tetrachloropropane feedstock;
 2-a) contacting the 1,1,1,3-tetrachloropropane feedstock with a metal catalyst, a metal salt catalyst or any combination thereof, in a dehydrochlorination zone to produce a reaction mixture comprising 1,1,1,3-tetrachloropropane and 1,1,3-trichloropropene, and 2-b) treating the reaction mixture obtained in step 2-a) to obtain a 1,1,3-trichloropropene feedstock;

3-a) contacting the 1,1,3-trichloropropene feedstock with chlorine in a reaction zone to produce a reaction mixture containing 1,1,1,2,3-pentachloropropane and 1,1,3-trichloropropene, the reaction zone being different from the dehydrochlorination zone, and 3-b) treating the reaction mixture obtained in step 3-a) to obtain the highly pure 1,1,1,2,3-pentachloropropane product, wherein, in step 3-a), the degree of conversion of the 1,1,3-trichloropropene starting material to the 1,1,1,2,3-pentachlorpropane product is controlled such that the molar ratio of 1,1,1,2,3-pentachloropropane:1,1,3-trichloropropene in the reaction mixture produced in step 3-a) does not exceed 95:5.

29. A process for preparing a highly pure 1,1,1,2,3-pentachloropropane product comprising:

1-a) providing a reaction mixture comprising ethylene, carbon tetrachloride and a catalyst in a principal alkylation zone to produce 1,1,1,3-tetrachloropropane in the reaction mixture, and 1-b) treating the reaction mixture obtained in step 1-a) to obtain a 1,1,1,3-tetrachloropropane feedstock;

2-a) contacting the 1,1,1,3-tetrachloropropane feedstock with a metal catalyst, a metal salt catalyst or any combination thereof, in a dehydrochlorination zone to produce a reaction mixture comprising 1,1,1,3-tetrachloropropane and 1,1,3-trichloropropene, and 2-b) treating the reaction mixture obtained in step 2-a) to obtain a 1,1,3-trichloropropene feedstock;

3-a) contacting the 1,1,3-trichloropropene feedstock with chlorine in a reaction zone to produce a reaction mixture containing 1,1,1,2,3-pentachloropropane and 1,1,3-trichloropropene, the reaction zone being different from the dehydrochlorination zone, and 3-b) treating the reaction mixture obtained in step 3-a) to obtain the highly pure 1,1,1,2,3-pentachloropropane product, wherein the reaction mixture produced in step 3-a) is subjected to an aqueous treatment and/or hydrolysis step.

30. The process according to claim 29, wherein the aqueous treatment and/or hydrolysis step comprises contacting the reaction mixture with an aqueous medium in an aqueous treatment zone.

\* \* \* \* \*